(12) United States Patent
Mozdzierz et al.

(10) Patent No.: US 11,596,400 B2
(45) Date of Patent: Mar. 7, 2023

(54) HANDHELD ELECTROMECHANICAL SURGICAL SYSTEM

(71) Applicant: Covidien LP, Mansfield, MA (US)

(72) Inventors: Patrick Mozdzierz, Glastonbury, CT (US); Anthony Sgroi, Jr., Wallingford, CT (US); James P. Delbo, Danville, PA (US); Charles R. Kollar, Washington, DC (US); John J. Hryb, IV, Southington, CT (US); Scott G. Firth, Guilford, CT (US); David E. Valentine, Jr., Hamden, CT (US); Paul D. Richard, Shelton, CT (US); Stephen R. Paul, Burlington, CT (US); Steven H. Joyce, Durham, CT (US); Haley E. Strassner, Hamden, CT (US); Alexander J. Hart, Tolland, CT (US); Joseph Eisinger, Northford, CT (US)

(73) Assignee: COVIDIEN LP, Mansfield, MA (US)

( * ) Notice: Subject to any disclaimer, the term of this patent is extended or adjusted under 35 U.S.C. 154(b) by 234 days.

(21) Appl. No.: 17/019,721

(22) Filed: Sep. 14, 2020

(65) Prior Publication Data

US 2020/0405304 A1 Dec. 31, 2020

Related U.S. Application Data

(63) Continuation-in-part of application No. 15/972,641, filed on May 7, 2018, now Pat. No. 11,045,199.
(Continued)

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 90/90* (2016.02);
(Continued)

(58) Field of Classification Search
CPC ............ A61B 17/068; A61B 17/072; A61B 17/07207; A61B 17/115; A61B 17/1155;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

Japanese Office Action dated Apr. 13, 2022 corresponding to counterpart Patent Application JP 2015-231525.
(Continued)

*Primary Examiner* — Scott A Smith
(74) *Attorney, Agent, or Firm* — Carter, DeLuca & Farrell, LLP

(57) ABSTRACT

A handheld electromechanical surgical device, capable of effectuating a surgical procedure, includes a handle assembly having a power source; at least one motor coupled to the power source; and a controller configured to control the motor. The surgical device includes an adapter assembly having an electrical assembly having a proximal end in communication with the controller of the handle assembly. The surgical device includes a reload configured to selectively connect to a distal end of the adapter assembly. The reload includes an annular array of staples; an annular staple
(Continued)

pusher for ejecting the staples; and a data storage device selectively connectable to a distal end of the electrical assembly. The data storage device receives and stores performance data of the surgical device from the controller of the handle assembly.

22 Claims, 74 Drawing Sheets

Related U.S. Application Data

(60) Provisional application No. 62/517,276, filed on Jun. 9, 2017, provisional application No. 62/517,297, filed on Jun. 9, 2017.

(51) Int. Cl.
    *A61B 17/29* (2006.01)
    *A61B 90/90* (2016.01)

(52) U.S. Cl.
    CPC ............ *A61B 2017/0046* (2013.01); *A61B 2017/00084* (2013.01); *A61B 2017/00221* (2013.01); *A61B 2017/00477* (2013.01); *A61B 2017/07214* (2013.01); *A61B 2017/07271* (2013.01); *A61B 2017/07285* (2013.01); *A61B 2017/2927* (2013.01); *A61B 2560/02* (2013.01)

(58) Field of Classification Search
    CPC .... A61B 17/00234; A61B 2017/00017; A61B 2017/00398; A61B 2017/00473; A61B 2017/00477; A61B 2017/07214; A61B 2017/29; A61B 2017/2927; A61B 2017/2948; A61B 90/90; A61B 90/98
    USPC .............. 227/19, 175.2, 176.1, 180.1, 175.1; 606/1, 139, 219
    See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Mien et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |

(56) References Cited

U.S. PATENT DOCUMENTS

| | | |
|---|---|---|
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,017,354 A | 1/2000 | Culp et al. |
| 6,024,748 A | 2/2000 | Manzo et al. |
| 6,025,683 A | 2/2000 | Philipp |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,090,123 A | 7/2000 | Culp et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,237,604 B1 | 5/2001 | Burnside et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,556,778 B2 | 4/2003 | Zhang et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,940,255 B2 | 9/2005 | Loch |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,126,310 B1 | 10/2006 | Barron |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,193,519 B2 | 3/2007 | Root et al. |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,117 B2 | 10/2007 | Krueger et al. |
| 7,285,125 B2 | 10/2007 | Viola |
| 7,285,177 B2 | 10/2007 | Bushoff et al. |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,362,062 B2 | 4/2008 | Schneider et al. |
| 7,364,060 B2 | 4/2008 | Milliman |
| 7,398,908 B2 | 7/2008 | Holsten et al. |
| 7,399,305 B2 | 7/2008 | Csiky et al. |

(56) References Cited

U.S. PATENT DOCUMENTS

| | | |
|---|---|---|
| 7,400,107 B2 | 7/2008 | Schneider et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,514,890 B2 | 4/2009 | Schneider et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,638,958 B2 | 12/2009 | Philipp et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,784,663 B2 | 8/2010 | Shelton, IV |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,063 B2 * | 4/2011 | Zemlok ............ A61B 17/115 227/176.1 |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 7,998,157 B2 | 8/2011 | Culp et al. |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,154,239 B2 | 4/2012 | Katsuki et al. |
| 8,157,153 B2 | 4/2012 | Shelton, IV et al. |
| 8,161,977 B2 | 4/2012 | Shelton, IV et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,210,411 B2 | 7/2012 | Yates et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,375,808 B2 | 2/2013 | Blumenkranz et al. |
| 8,399,822 B2 | 3/2013 | Al-Ali |
| 8,400,108 B2 | 3/2013 | Powell et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,473,502 B2 | 6/2013 | Ledford et al. |
| 8,485,414 B2 | 7/2013 | Criscuolo et al. |

(56) References Cited

U.S. PATENT DOCUMENTS

| | | |
|---|---|---|
| 8,490,853 B2 | 7/2013 | Criscuolo et al. |
| 8,500,769 B2 | 8/2013 | Deng |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,657,174 B2 | 2/2014 | Yates et al. |
| 8,662,370 B2 | 3/2014 | Takei |
| 8,663,258 B2 | 3/2014 | Bettuchi et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,708,211 B2 * | 4/2014 | Zemlok ............ A61B 17/07207 227/176.1 |
| 8,708,213 B2 | 4/2014 | Shelton, IV et al. |
| 8,733,611 B2 | 5/2014 | Milliman |
| 8,746,532 B2 | 6/2014 | Nalagatla et al. |
| 8,800,837 B2 * | 8/2014 | Zemlok ............ A61B 17/07207 227/176.1 |
| 8,806,973 B2 | 8/2014 | Ross et al. |
| 8,808,311 B2 | 8/2014 | Heinrich et al. |
| 8,893,946 B2 | 11/2014 | Boudreaux et al. |
| 8,959,617 B2 | 2/2015 | Newlin et al. |
| 8,989,903 B2 | 3/2015 | Weir et al. |
| 9,017,851 B2 | 4/2015 | Felder et al. |
| 9,084,601 B2 | 7/2015 | Moore et al. |
| 9,089,338 B2 | 7/2015 | Smith et al. |
| 9,095,339 B2 | 8/2015 | Moore et al. |
| 9,113,874 B2 | 8/2015 | Shelton, IV et al. |
| 9,142,992 B2 | 9/2015 | Malackowski et al. |
| 9,226,750 B2 | 1/2016 | Weir et al. |
| 9,326,769 B2 | 5/2016 | Shelton, IV et al. |
| 9,326,770 B2 | 5/2016 | Shelton, IV et al. |
| 9,364,249 B2 | 6/2016 | Kimball et al. |
| 9,393,017 B2 | 7/2016 | Flanagan et al. |
| 9,398,911 B2 | 7/2016 | Auld |
| 9,439,651 B2 | 9/2016 | Smith et al. |
| 9,498,219 B2 | 11/2016 | Moore et al. |
| 10,271,851 B2 | 4/2019 | Shelton, IV et al. |
| 10,292,704 B2 | 5/2019 | Harris et al. |
| 11,045,199 B2 * | 6/2021 | Mozdzierz ............ A61B 17/072 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0102472 A1 | 5/2007 | Shelton |
| 2008/0255413 A1 * | 10/2008 | Zemlok ............... A61B 17/1155 600/106 |
| 2009/0090763 A1 * | 4/2009 | Zemlok ............ A61B 17/07207 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0257636 A1 | 10/2011 | Whitman et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0110455 A1 * | 4/2014 | Ingmanson .......... A61B 17/072 227/176.1 |
| 2015/0342601 A1 * | 12/2015 | Williams ............. A61B 17/068 227/175.1 |
| 2015/0351765 A1 * | 12/2015 | Valentine ............... A61B 90/90 227/176.1 |
| 2015/0374371 A1 | 12/2015 | Richard et al. |
| 2016/0095585 A1 | 4/2016 | Zergiebel et al. |
| 2016/0106406 A1 | 4/2016 | Cabrera |
| 2016/0132026 A1 * | 5/2016 | Wingardner ............. G05B 9/02 700/275 |

(56) References Cited

U.S. PATENT DOCUMENTS

| | | | |
|---|---|---|---|
| 2016/0143641 A1 | 5/2016 | Sapienza et al. | |
| 2016/0157856 A1 | 6/2016 | Williams et al. | |
| 2016/0174988 A1 | 6/2016 | D'Agostino et al. | |
| 2016/0249915 A1* | 9/2016 | Beckman | H01M 50/572 227/175.1 |
| 2016/0249945 A1 | 9/2016 | Shelton, IV et al. | |
| 2016/0256184 A1 | 9/2016 | Shelton, IV et al. | |
| 2016/0302792 A1 | 10/2016 | Motai | |
| 2016/0310134 A1 | 10/2016 | Contini et al. | |
| 2017/0181745 A1 | 6/2017 | Penna et al. | |
| 2018/0353186 A1 | 12/2018 | Mozdzierz et al. | |

FOREIGN PATENT DOCUMENTS

| | | |
|---|---|---|
| CN | 103 622 727 A | 3/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2684529 A2 | 1/2014 |
| EP | 2954854 A2 | 12/2015 |
| EP | 3064153 A2 | 9/2016 |
| EP | 3231374 A1 | 10/2017 |
| EP | 3412225 A1 | 12/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| JP | 2015231525 A | 12/2015 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2016171947 A1 | 10/2016 |

OTHER PUBLICATIONS

Extended European Search Report dated Mahy 25, 2022 corresponding to counterpart Patent Application EP 21196476.2.

Extended European Search Report from Appl. No. 14181908.6 dated May 26, 2015.

European Examination Report from Appl. No.: 14181908.6 dated May 3, 2016.

Extended European Search Report dated Nov. 6, 2018 issued in corresponding EP Appln. No. EP18176772.4.

European Examination Report dated Oct. 4, 2019 issued in corresponding EP Appln. No. 18176772.4.

Partial European Search Report dated May 8, 2020 issued in corresponding EP Appln. No. 20154026.7.

Extended European Search Report dated May 8, 2020 issued in corresponding EP Appln. No. 20154027.5.

European Examination Report dated Apr. 22, 2020 issued in corresponding EP Appln. No. 18176772.4.

Extended European Search Report dated Jul. 29, 2020 issued in corresponding EP Appln. No. 20154026.7.

First Chinese Office Action dated Aug. 2, 2022 issued in CN Appln. No. 201810569363.5.

Extended European Search Report dated May 25, 2022 corresponding to counterpart Patent Application EP 21196476.2.

Chinese Office Action dated Aug. 2, 2022 issued in corresponding CN Appln. No. 201810576680.X.

* cited by examiner

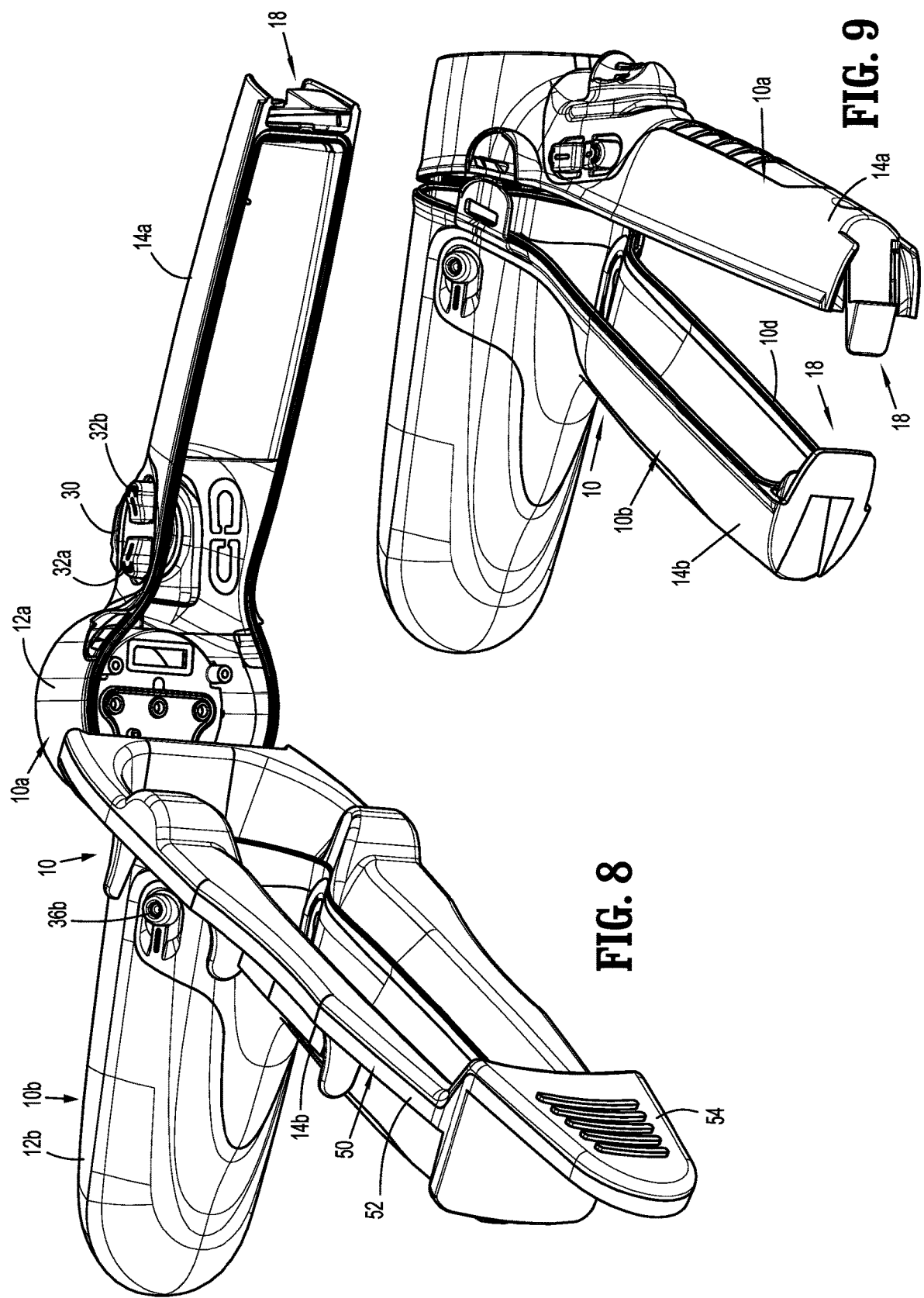

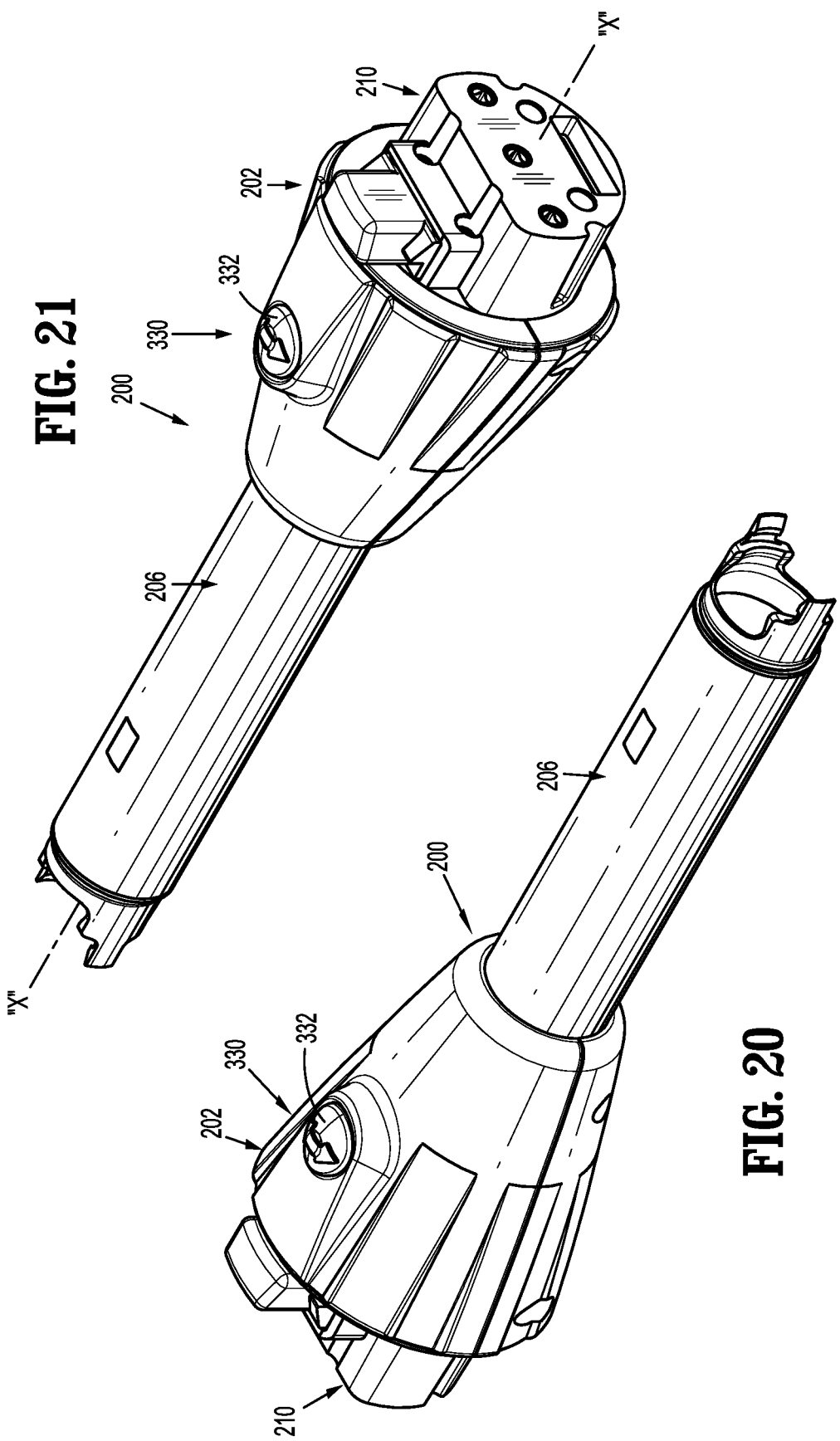

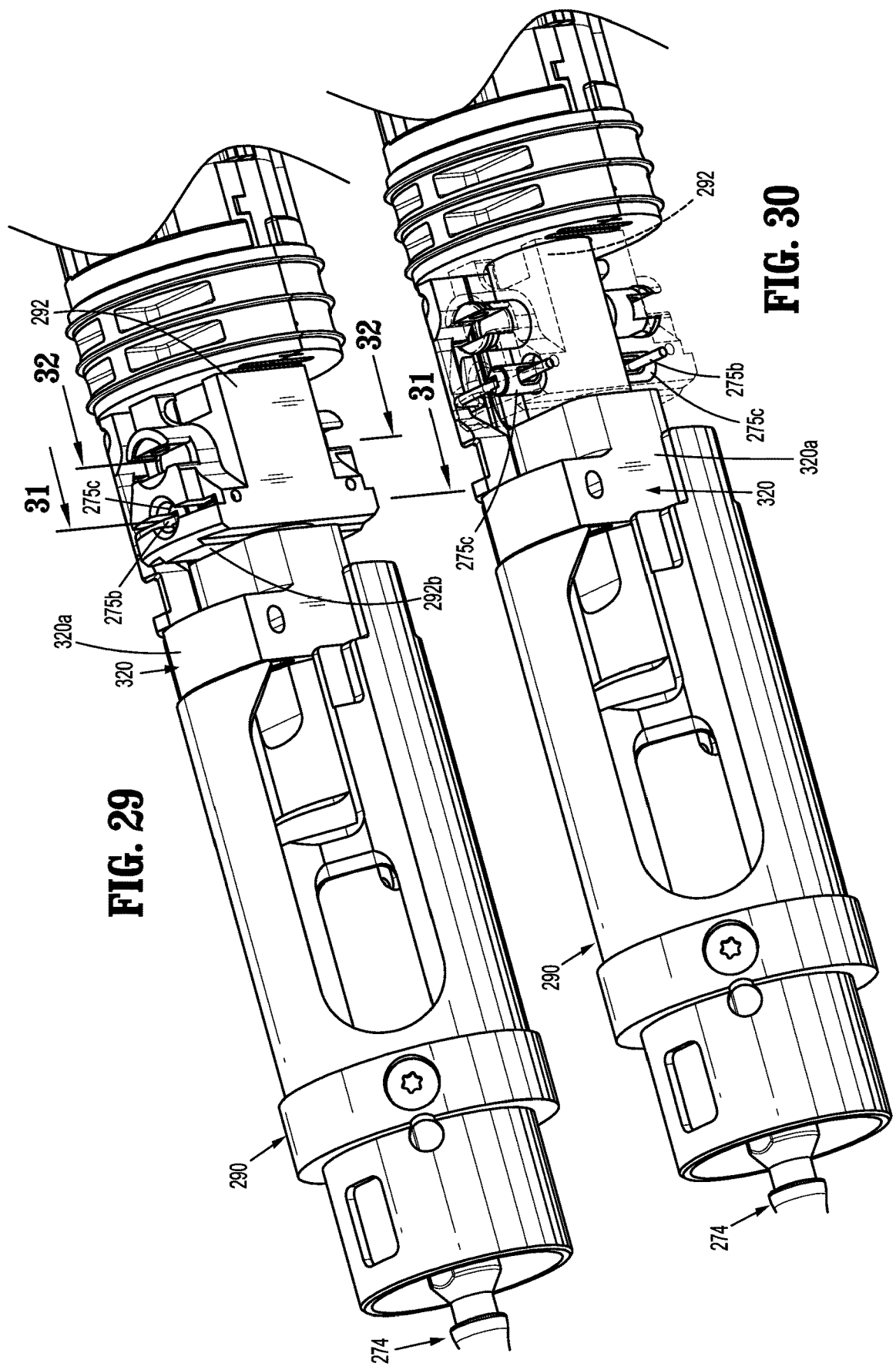

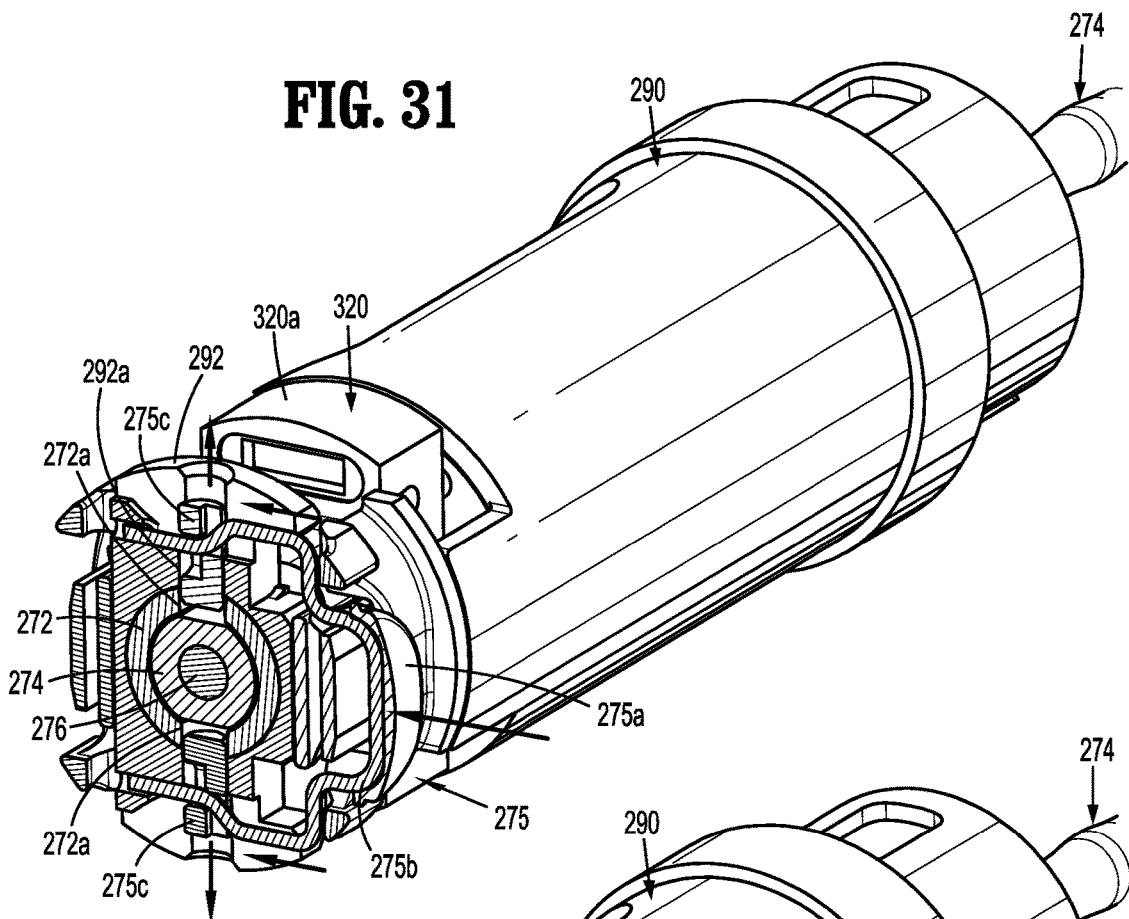

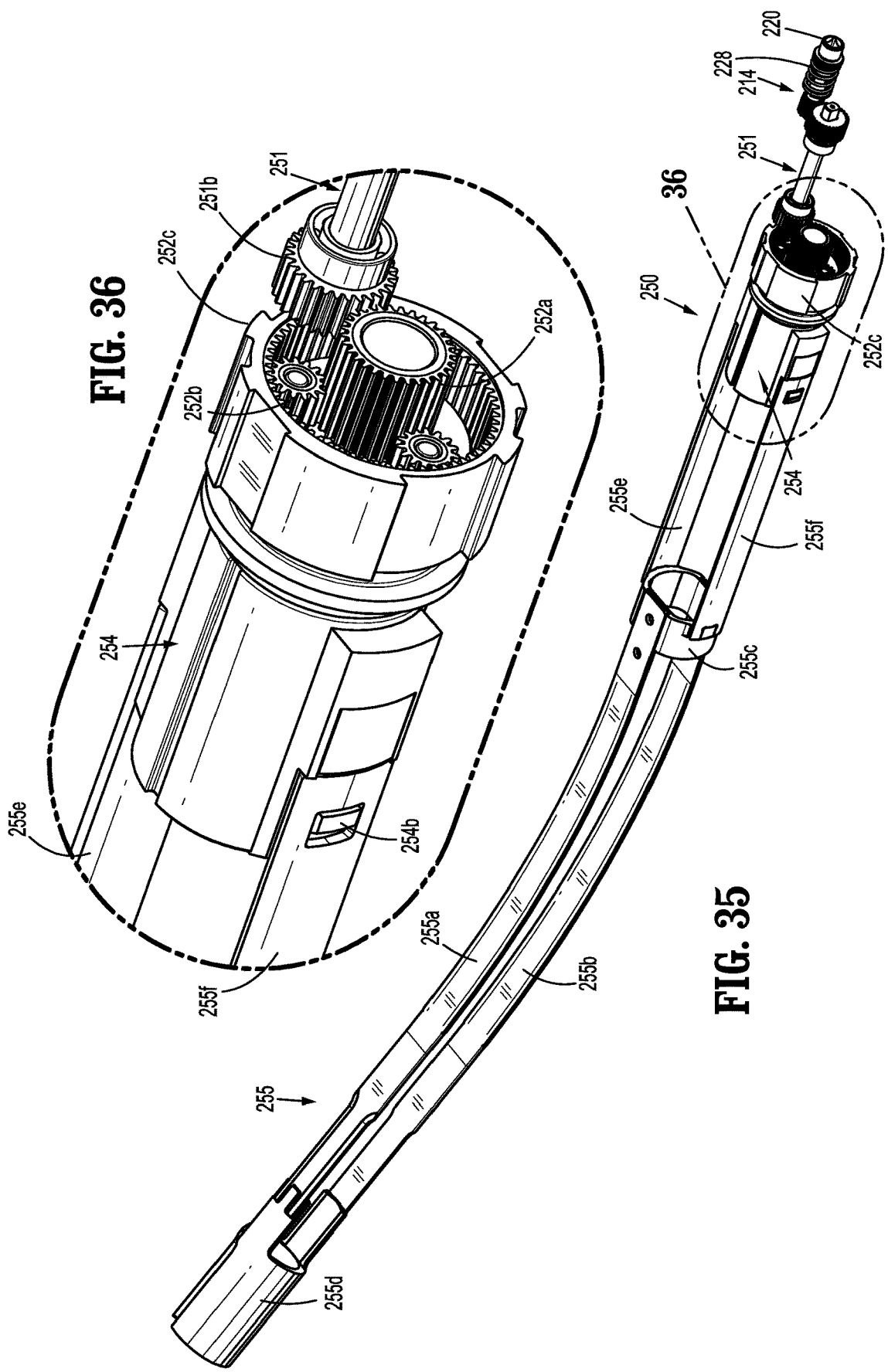

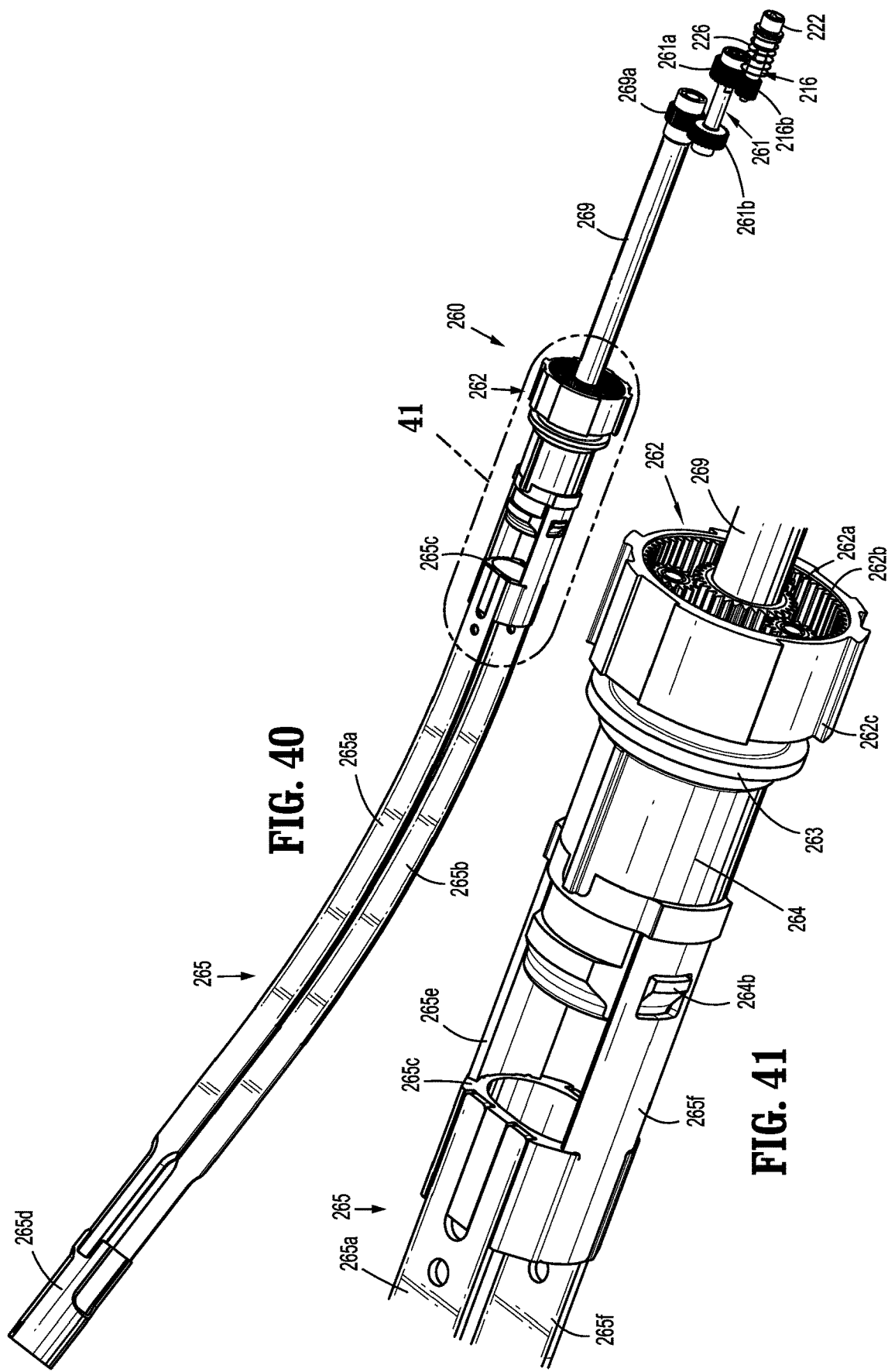

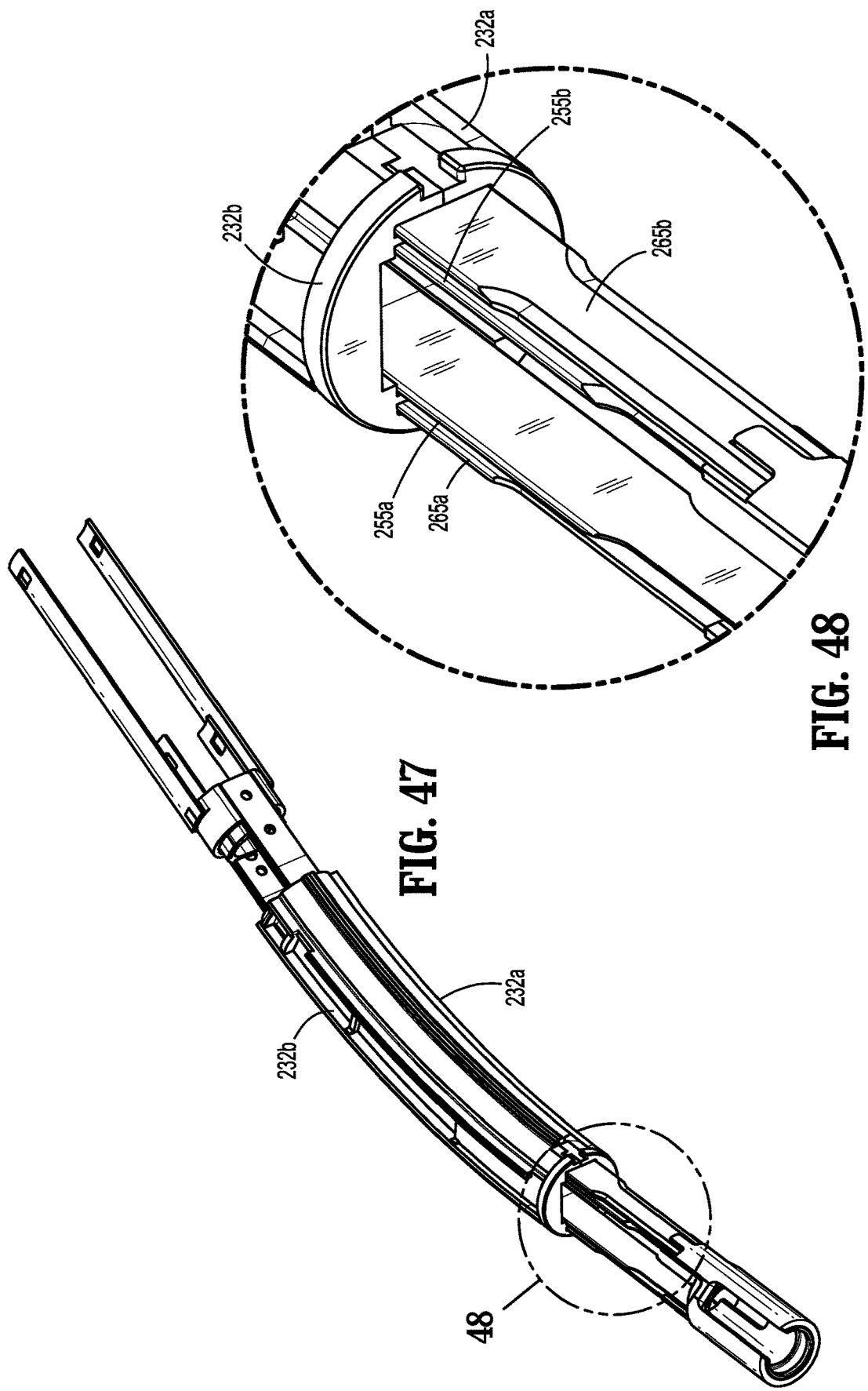

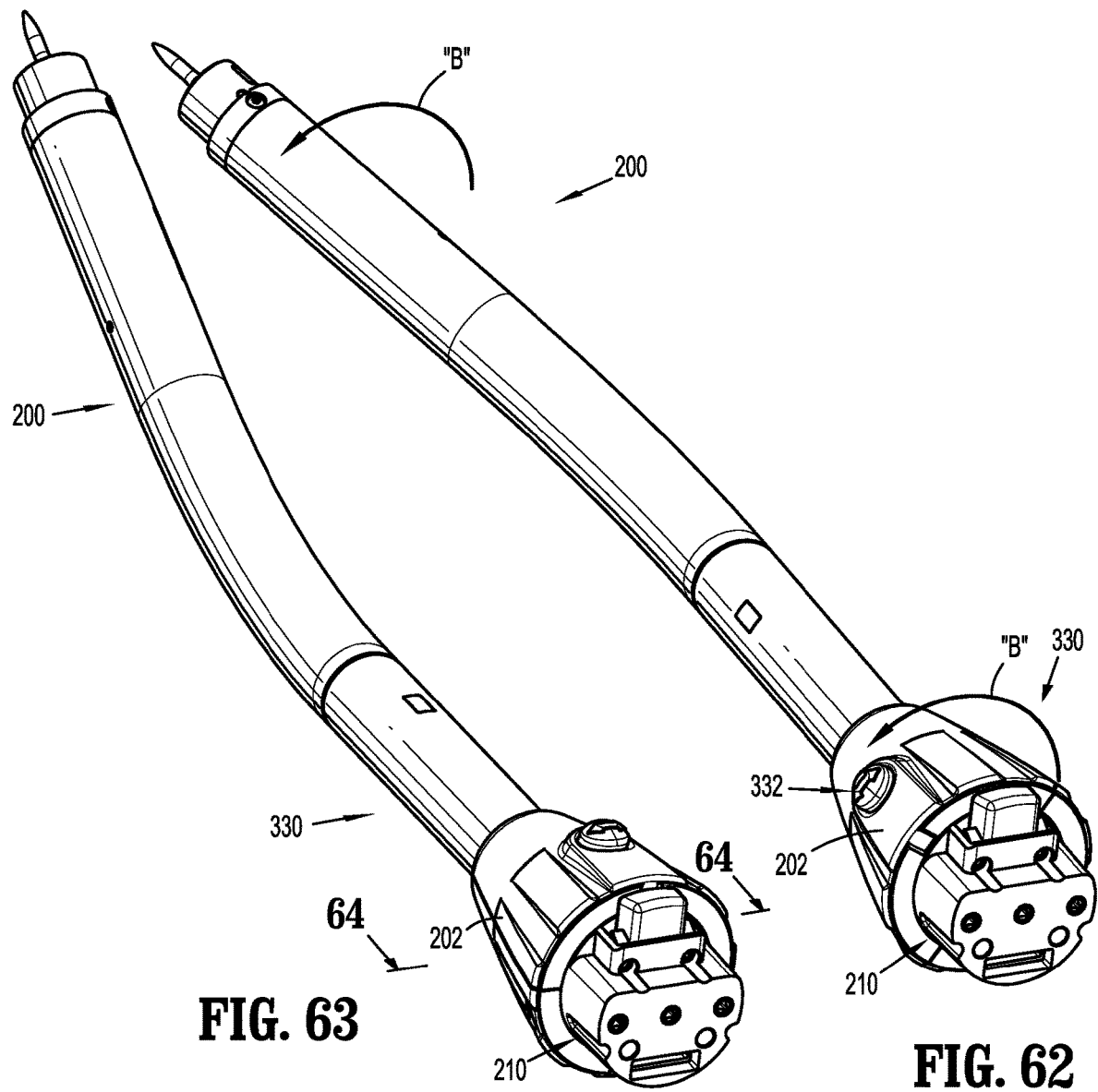

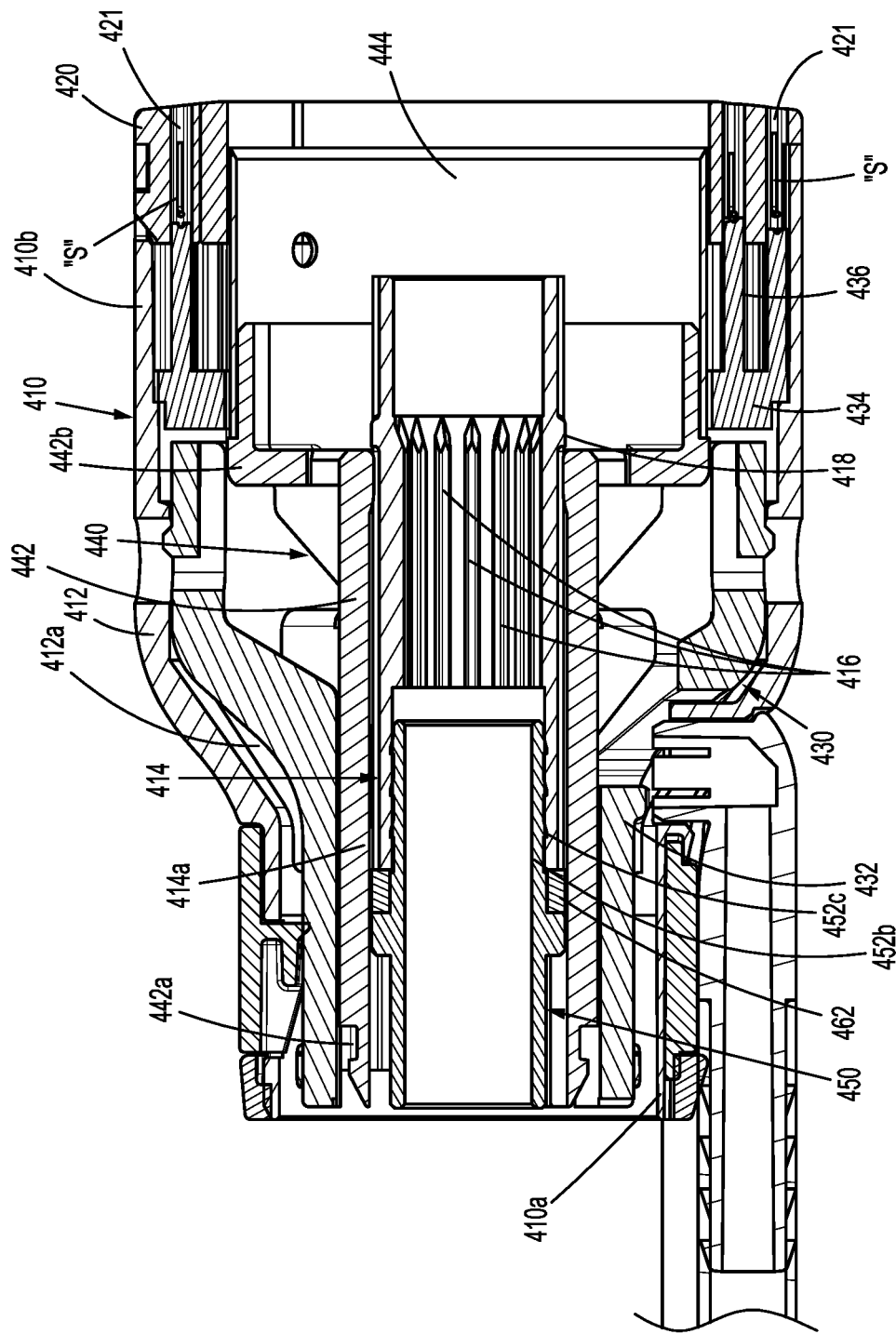

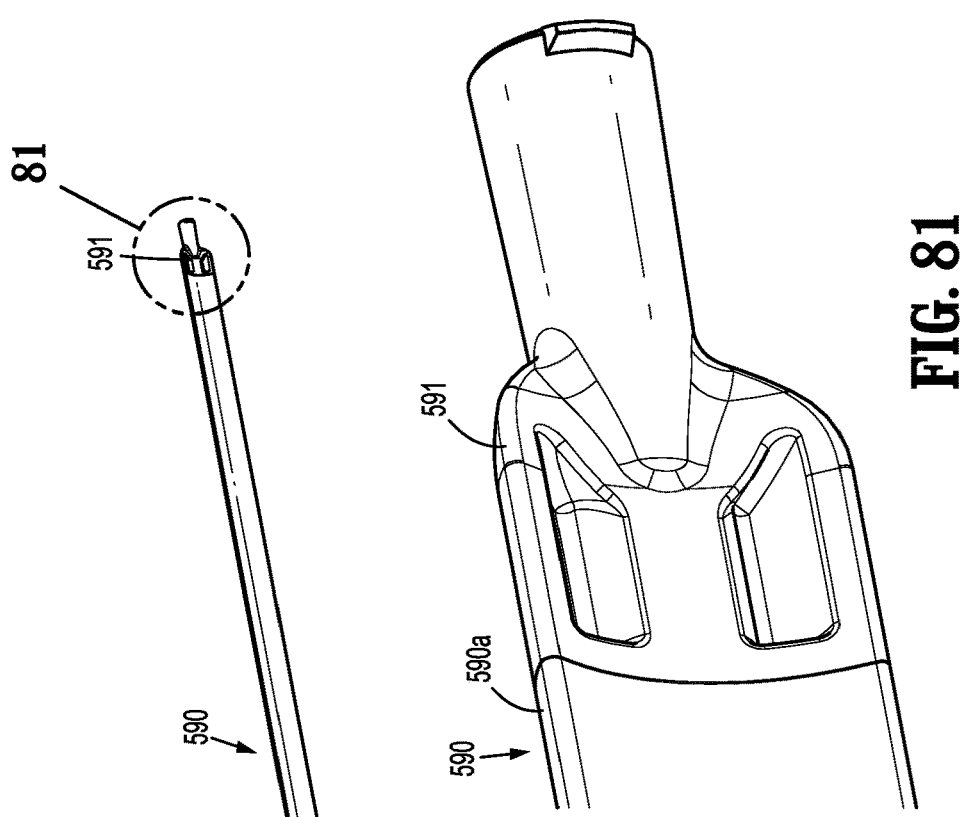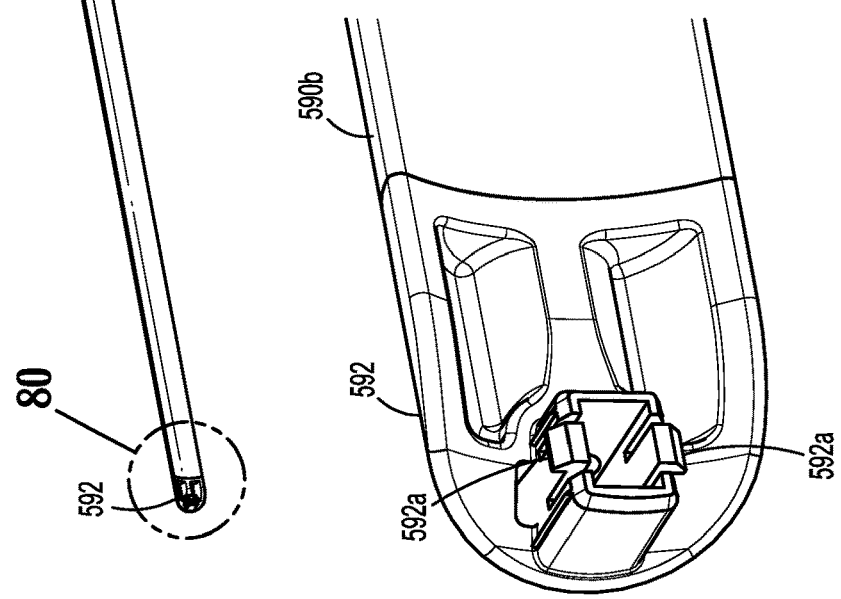

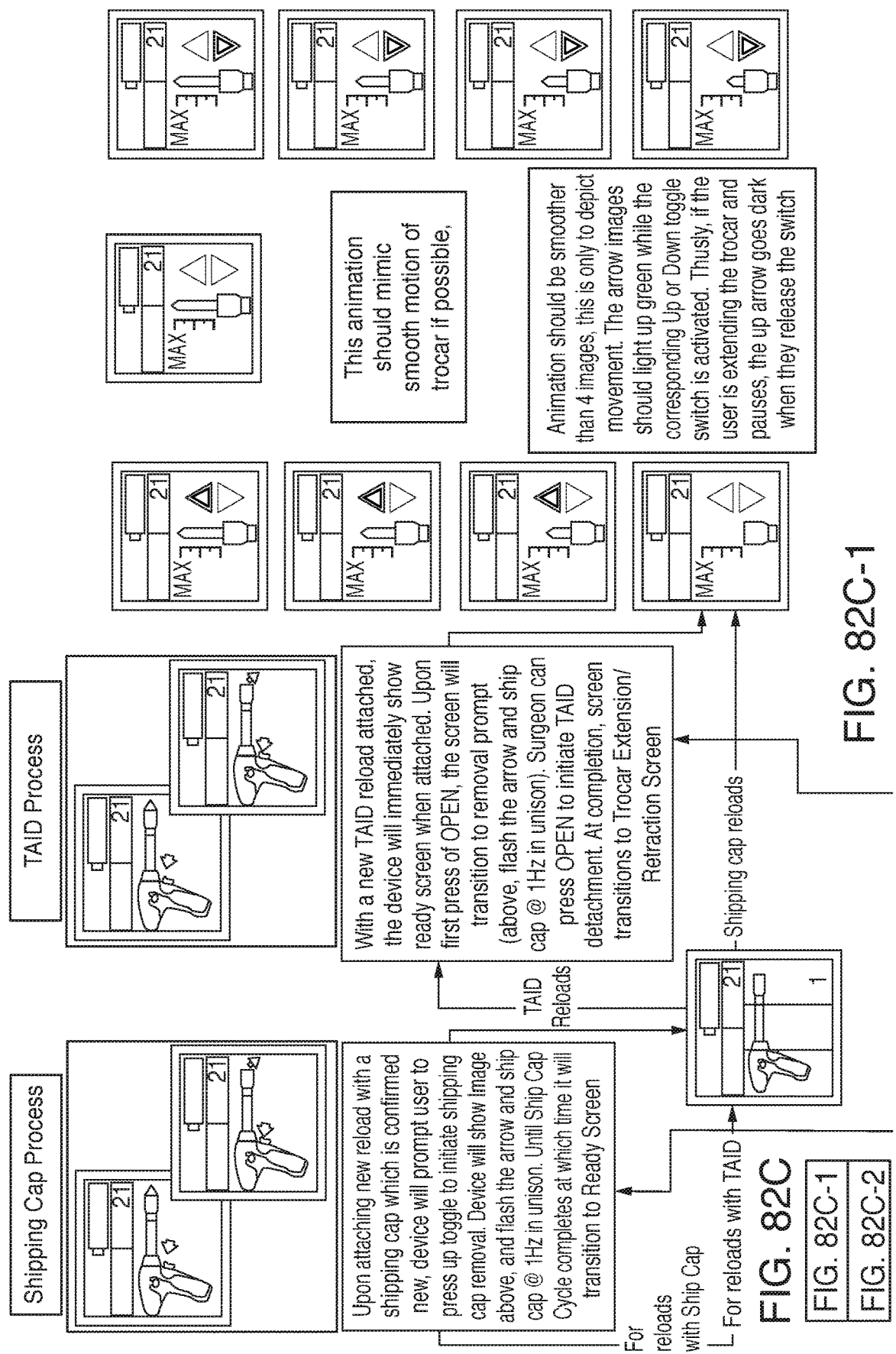

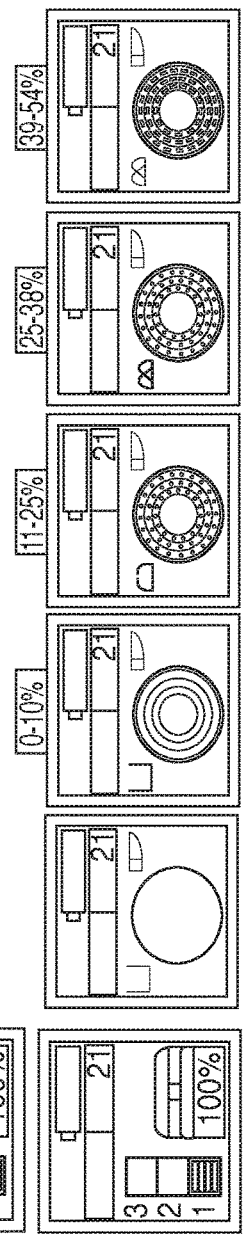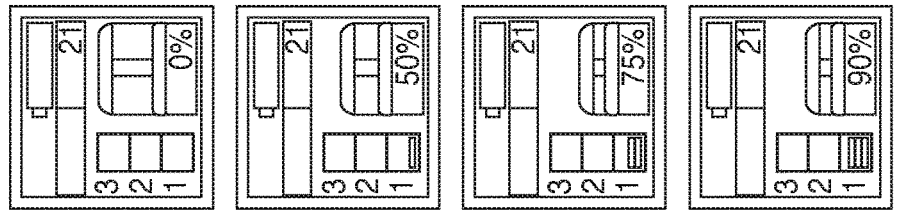
FIG. 82D-1
FIG. 82D
| FIG. 82D-1 |
| FIG. 82D-2 |

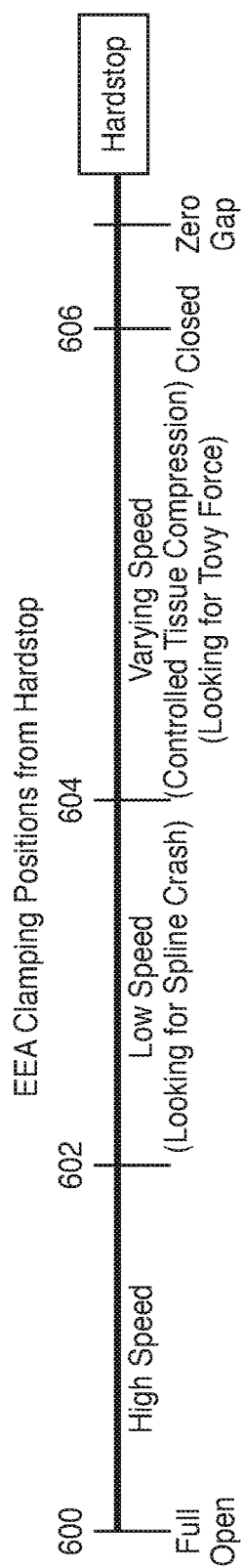
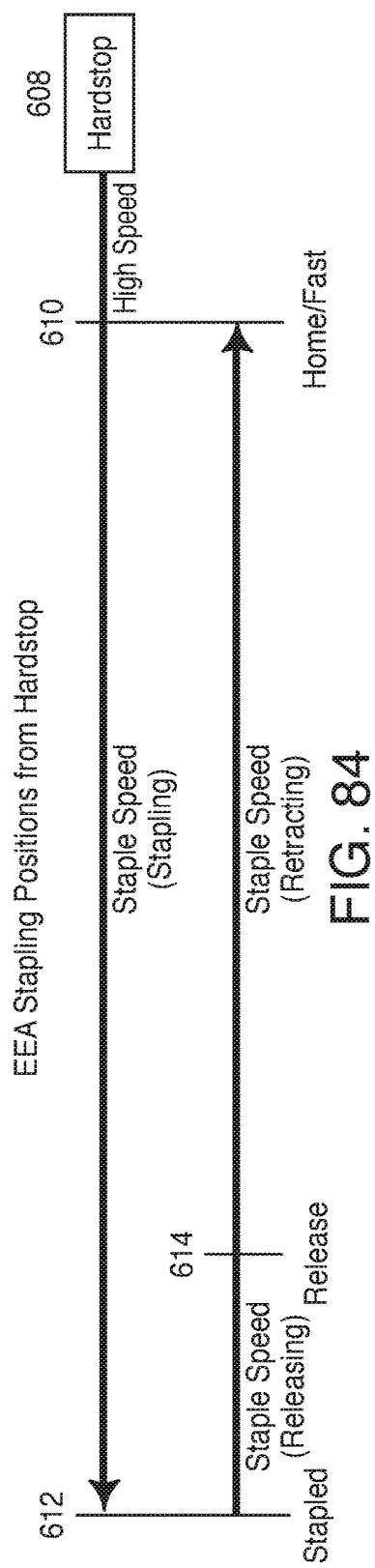
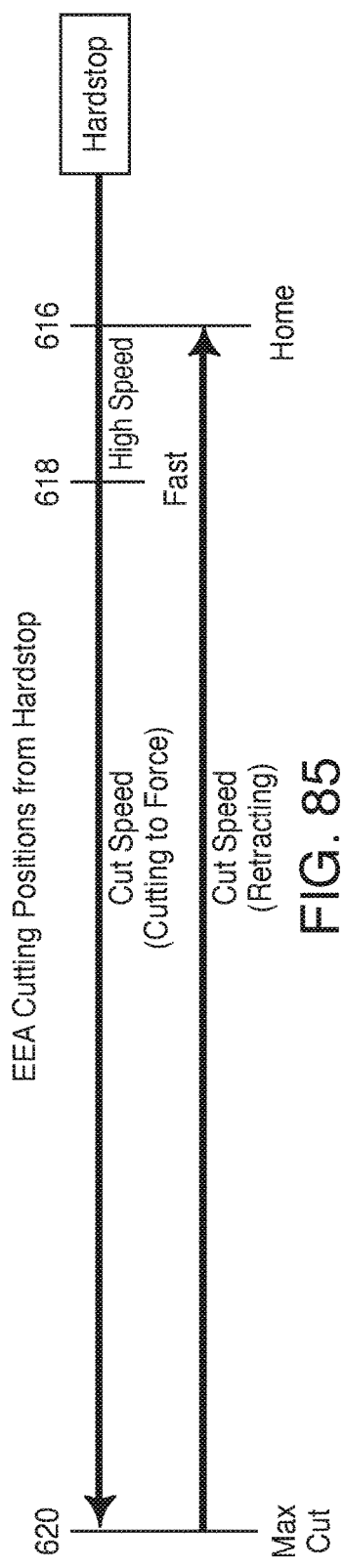
FIG. 83
FIG. 84
FIG. 85

HANDHELD ELECTROMECHANICAL SURGICAL SYSTEM

CROSS-REFERENCE TO RELATED APPLICATIONS

This application is a Continuation-in-Part Application which claims the benefit of and priority to U.S. patent application Ser. No. 15/972,641, filed on May 7, 2018, now U.S. Pat. No. 11,045,199, which claims the benefit of and priority to each of U.S. Provisional Patent Application Ser. No. 62/517,276, filed Jun. 9, 2017, and U.S. Provisional Patent Application Ser. No. 62/517,297, filed Jun. 9, 2017. The entire disclosures of all of the foregoing applications are incorporated by reference herein.

BACKGROUND

1. Technical Field

The present disclosure relates to surgical devices. More specifically, the present disclosure relates to handheld electromechanical surgical systems for performing surgical procedures.

2. Background of Related Art

One type of surgical device is a circular clamping, cutting and stapling device. Such a device may be employed in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been affected, the circular stapling apparatus is removed from the surgical site.

A number of surgical device manufacturers have developed product lines with proprietary powered drive systems for operating and/or manipulating the surgical device. In many instances the surgical devices include a powered handle assembly, which is reusable, and a disposable staple cartridge assembly, end effector or the like that is selectively connected to the powered handle assembly prior to use and then disconnected from the staple cartridge assembly or end effector following use in order to be disposed of or in some instances sterilized for re-use.

The use of powered electro and endomechanical surgical staplers, including intelligent battery power, has grown tremendously over the past few decades. Advanced technology and informatics within these intelligent battery-powered stapling devices provide the ability to gather clinical data and drive design improvements to ultimately improve patient outcomes. Accordingly, a need exists for improved powered electro and endomechanical surgical staplers that are capable of evaluating conditions that affect staple formation with the intention of building a more intelligent stapling algorithm.

SUMMARY

The present disclosure relates to handheld electromechanical surgical systems for performing surgical procedures.

According to an aspect of the present disclosure, a handheld electromechanical surgical device capable of effectuating a surgical procedure is provided. The surgical device includes a handle assembly having a power source; at least one motor coupled to the power source; and a controller configured to control the motor. The surgical device includes an adapter assembly coupled to and extending from the handle assembly. The adapter assembly includes a force transmitting and rotation converting assembly for receiving and communicating a rotation from the at least one motor of the handle assembly to axially translating forces of a driven assembly thereof; and an electrical assembly having a proximal end in communication with the controller of the handle assembly, and a distal end. The surgical device includes a reload configured to selectively connect to a distal portion of the adapter assembly. The reload includes an annular array of staples; an annular staple pusher for ejecting the staples; and a data storage device selectively connectable to the distal end of the electrical assembly of the adapter assembly. The data storage device receives and stores performance data of the surgical device from the controller of the handle assembly.

The the data storage device of the reload may include information pre-stored thereon prior to any use thereof. The pre-stored information may include at least one of lot number, staple size, knife diameter, lumen size, fire count, manufacturing stroke offsets, excessive force index, shipping cap assembly presence, or demonstration modes.

The data storage device of the reload may be configured to have performance data written thereto and stored thereon during or following any use thereof.

The data storage device of the reload may be configured to have performance data written thereto and stored thereon following a successful or unsuccessful firing of the surgical device.

The performance data written and stored to the data storage device of the reload may include clamping forces for the surgical procedure, stapling forces for the surgical procedure, cutting forces for the surgical procedure, a maximum clamping force, a maximum stapling force or a maximum cutting force.

The performance data may be written and stored to the controller of the handle assembly.

During or following any use of the surgical device, performance data related to the use of the surgical device is written to and stored in the data storage device of the reload.

Following a successful or unsuccessful firing of the surgical device, performance data related to the successful or unsuccessful firing may be written to and stored in the data storage device of the reload.

The performance data written and stored to the data storage device of the reload may include clamping forces for the surgical procedure, stapling forces for the surgical procedure, cutting forces for the surgical procedure, a maximum clamping force, a maximum stapling force or a maximum cutting force.

The data storage device of the reload may include information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

The performance data may be written and stored to the controller of the handle assembly.

According to another aspect of the disclosure, a surgical stapler reload configured for selective connection to a surgical device capable of effectuating a surgical procedure, is provided. The surgical stapler reload includes an annular array of staples; an annular staple pusher for ejecting the staples; and a data storage device selectively connectable to an electrical assembly the surgical device, wherein the data storage device receives and stores performance data from a controller of the surgical device.

The data storage device of the reload may include information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

The data storage device of the reload may be configured to have performance data written thereto and stored thereon during or following any use thereof.

The data storage device of the reload may be configured to have performance data written thereto and stored thereon following a successful or unsuccessful firing of the surgical device.

The performance data written and stored to the data storage device of the reload may include clamping forces for the surgical procedure, stapling forces for the surgical procedure, cutting forces for the surgical procedure, a maximum clamping force, a maximum stapling force or a maximum cutting force.

According to yet another aspect of the present disclosure, a method of gathering surgical procedure performance data for a surgical device, is provided. The method includes performing a surgical procedure with a surgical device. The surgical device includes a handle assembly having a power source; at least one motor coupled to the power source; and a controller configured to control the motor; and a reload configured to selectively connect to the handle assembly. The reload includes an annular array of staples; an annular staple pusher for ejecting the staples; and a data storage device selectively connected to the controller of the handle assembly. The method includes transmitting the performance data of the surgical device from the controller thereof to the data storage device of the reload; and storing the performance data of the surgical device in the data storage device of the reload.

The method may further include transmitting and storing the performance data to the data storage device of the reload following a successful or unsuccessful firing of the surgical device.

The performance data written and stored to the data storage device of the reload may include clamping forces for the surgical procedure, stapling forces for the surgical procedure, cutting forces for the surgical procedure, a maximum clamping force, a maximum stapling force or a maximum cutting force.

The method may further include writing the performance data and storing the performance data in the controller of the surgical device.

The method may further include disconnecting the reload from the surgical device; and accessing the performance data stored in the data storage device of the reload.

The storing of the performance data of the surgical device in the data storage device of the reload may occur while the surgical device is in the field of use; and the accessing of the performance data stored in the data storage device of the reload may occur while the reload is outside of the field of use.

According to a further aspect of the present disclosure, a method is provided of operating a surgical device including a surgical stapler reload and an anvil assembly having a head assembly movable between a non-tilted orientation for cooperation with the surgical staple reload to form a plurality of surgical staples and a tilted orientation. The method includes, following a complete firing of the surgical device, and following a tilting of the head assembly of the anvil assembly from the non-titled orientation to the tilted orientation, monitoring an axial distance of the tilted head assembly relative to the reload.

The method may further include monitoring forces acting on the anvil assembly as the anvil assembly is translated towards the reload.

The method may further include stopping axial translation of the anvil assembly when the forces acting on the anvil assembly exceed a predetermined threshold.

The method may still further include monitoring forces acting on the tilted head assembly of the anvil assembly as the tilted head assembly is translated towards the reload.

The method may further include stopping translation of the tilted head assembly toward the reload when the forces acting on the tilted head assembly exceed a predetermined threshold.

According to the method, an increase in the forces being monitored during axial translation of the anvil assembly may be indicative of tissue being captured between the tilted head assembly and the reload.

The method may further include activating an alert when the forces acting on the anvil assembly exceed the predetermined threshold.

The monitoring may be performed by a controller of the surgical device.

According to the method, the reload may be circular and may include a tissue contacting surface defining a reload plane that is orthogonal to an axis of translation of the anvil assembly; and the head assembly of the anvil assembly may be circular and may include a tissue contacting surface defining an anvil head plane that is (1) parallel to the reload plane when the head assembly is in the non-tilted orientation; and (2) angled relative to the reload plane when the head assembly is in the tilted orientation. The method may include monitoring when an outer radial edge of the head assembly is in relative close proximity to the tissue contacting surface of the reload while the head assembly is in the tilted orientation.

The method may further include monitoring an axial position of a trocar member of the surgical device relative to the reload for determining when the tilted head assembly of the anvil assembly is in relative close proximity to the reload.

According to yet another aspect of the present disclosure, a method is provided for operating a surgical device including a removable surgical stapler reload. The method includes attaching a selected surgical stapler reload to the surgical device; a controller of the surgical device reading information stored on the selected surgical stapler reload; and setting a maximum cut stroke for a knife of the selected surgical stapler reload based on the information stored on the selected surgical stapler reload.

The method may further include the controller of the surgical device monitoring an axial position of the knife of the selected surgical stapler reload relative to a housing of the selected surgical stapler reload.

The information stored on the selected surgical stapler reload may include at least one of staple size, knife diameter, lumen size, minimum cut stroke length, or maximum cut stroke length for the selected surgical stapler reload.

The method may further include setting a minimum cut stroke for the knife of the selected surgical stapler reload based on the information stored on the selected surgical stapler reload.

The controller of the surgical device may set the cut stroke for the selected surgical stapler reload.

The selected surgical stapler reload may be a first selected surgical stapler reload, and the method may include replacing the first selected surgical stapler reload with a second selected surgical stapler reload; and setting a maximum cut stroke for a knife of the second selected surgical stapler reload based on the information stored on the second selected surgical stapler reload.

The cut stroke for the knife of the first selected surgical stapler reload may be different than the cut stroke for the knife of the second selected surgical stapler reload.

Each surgical stapler reload may be an annular surgical stapler reload including an annular knife and an annular array of staple.

According to a further aspect of the present disclosure, a method is provided of operating a surgical device including a handheld electromechanical surgical device capable of operating a surgical reload capable of effectuating a surgical procedure, and a surgical adapter assembly for selectively electrically and mechanically interconnecting the surgical device and the removable surgical reload. The method includes mechanically and electrically attaching the adapter assembly to the surgical device; a main controller of the surgical device querying an event log of an electronic temperature sensor of the adapter assembly; and when the query indicates that the adapter assembly has undergone a sterilization cycle, the main controller of the surgical device permitting operation of surgical device to effectuate operation of the surgical reload via the adapter assembly.

The method may further include logging, by the electronic temperature sensor of the adapter assembly, a sterilizing cycle for the adapter assembly.

The method may further include logging, by the electronic temperature sensor of the adapter assembly, a temperature of the sterilizing cycle.

The method may still further include logging, by the electronic temperature sensor of the adapter assembly, a maximum temperature of the sterilizing cycle.

The method may further include logging, by the electronic temperature sensor of the adapter assembly, a duration of the sterilizing cycle.

The method may still further include rendering the adapter assembly disabled when the maximum temperature of the sterilization cycle is not obtained or when a minimum duration of the sterilization cycle is not obtained.

The method may further include rendering the surgical device disabled when the maximum temperature of the sterilization cycle is not obtained or when a minimum duration of the sterilization cycle is not obtained.

The method may still further include the main controller of the surgical device rendering the adapter assembly disabled when the maximum temperature of the sterilization cycle is not obtained or when a minimum duration of the sterilization cycle is not obtained.

The method may further include the main controller of the surgical device querying a number of sterilization cycles registered by the electronic temperature sensor.

The electronic temperature sensor may be a thermistor.

BRIEF DESCRIPTION OF THE DRAWINGS

Embodiments of the present disclosure are described herein with reference to the accompanying drawings, wherein:

FIG. 8 is a front, perspective view of the outer shell housing, shown in an open condition;

FIG. 9 is a front, perspective view of the outer shell housing, shown in a partially open condition, and with an insertion guide removed therefrom;

FIG. 20 is a front, perspective view of the adapter assembly of FIG. 1;

FIG. 21 is a rear, perspective view of the adapter assembly of FIGS. 1 and 20;

FIG. 29 is a perspective view, of a distal end portion of the first force/rotation transmitting/converting assembly of FIG. 25, illustrating a support block thereof;

FIG. 30 is a perspective view, of a distal end portion of the first force/rotation transmitting/converting assembly of FIG. 25, with the support block thereof shown in phantom;

FIG. 31 is a cross-sectional view as taken through 31-31 of FIG. 29;

FIG. 32 is a cross-sectional view as taken through 32-32 of FIG. 29;

FIG. 35 is a perspective view of the second force/rotation transmitting/converting assembly of FIG. 34;

FIG. 36 is an enlarged view of the indicated area of detail of FIG. 35;

FIG. 40 is a perspective view of the third force/rotation transmitting/converting assembly of FIG. 39;

FIG. 41 is an enlarged view of the indicated area of detail of FIG. 40;

FIG. 47 is a front, perspective view of the internal components of the distal end portion of the adapter assembly;

FIG. 48 is an enlarged view of the indicated area of detail of FIG. 47;

FIG. 62 is a rear, perspective view of the adapter assembly, illustrating a rotation of the rotation assembly and a shaft assembly relative to a drive coupling assembly thereof;

FIG. 63 is a rear, perspective view of the adapter assembly, illustrating the adapter assembly in a non-rotated position thereof;

FIG. 67 is a longitudinal, cross-sectional view of the assembled reload of FIG. 66;

FIG. 79 is a perspective view of the irrigation tube;

FIG. 80 is an enlarged view of the indicated area of detail of FIG. 79;

FIG. 81 is an enlarged view of the indicated area of detail of FIG. 79;

FIG. 83 is a schematic diagram illustrating travel distance and speed of the anvil assembly and a corresponding motor during a clamping sequence performed by the handheld surgical device of FIG. 1 according to an embodiment of the present disclosure;

FIG. 84 is a schematic diagram illustrating travel distance and speed of the driver and a corresponding motor during a stapling sequence performed by the handheld surgical device of FIG. 1 according to an embodiment of the present disclosure;

FIG. 85 is a schematic diagram illustrating travel distance and speed of the knife assembly and a corresponding motor during a cutting sequence performed by the handheld surgical device of FIG. 1 according to an embodiment of the present disclosure;

DETAILED DESCRIPTION OF EMBODIMENTS

Figure 1:
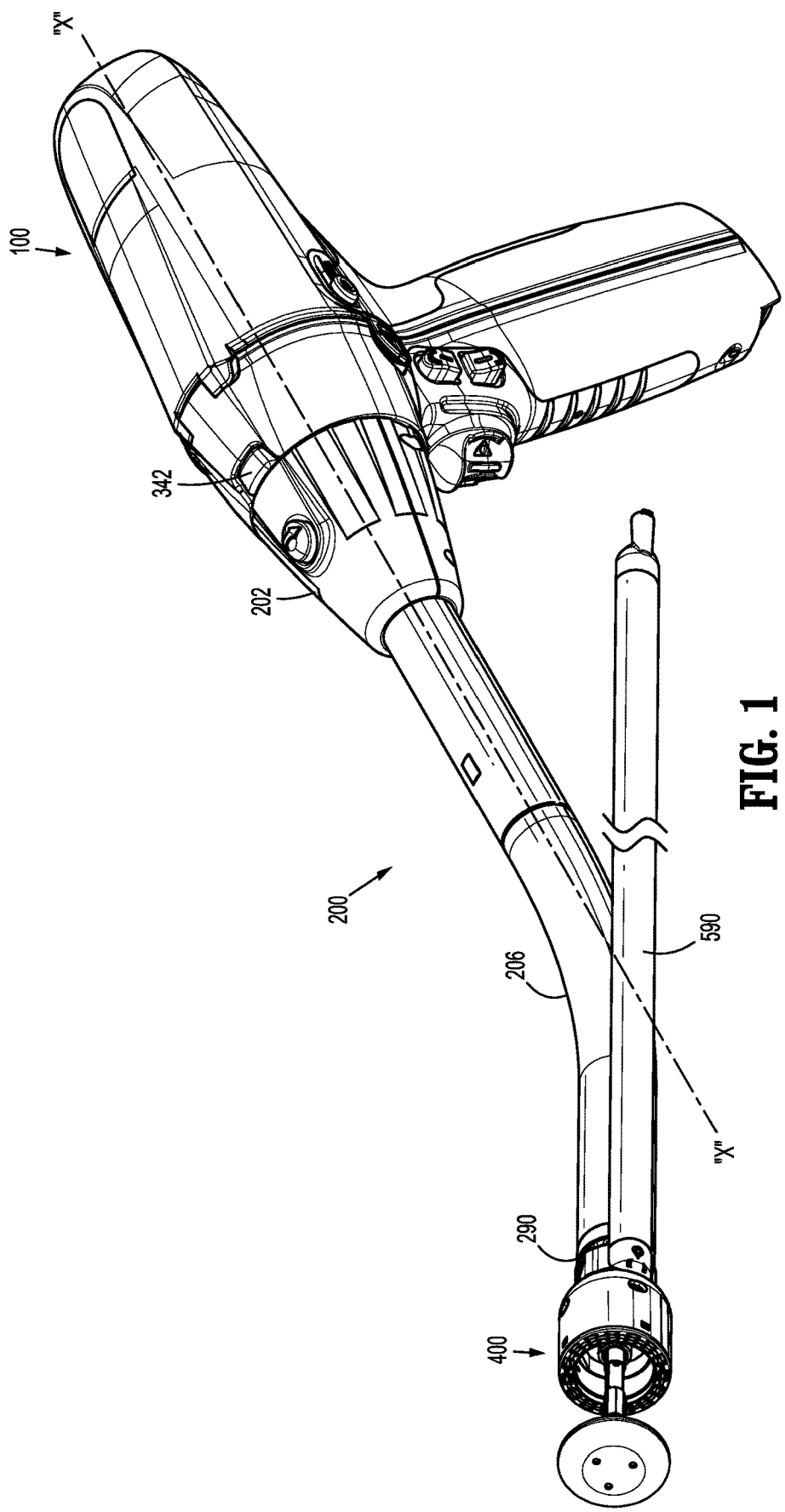
FIG. 1 is a perspective view of a handheld surgical device and adapter assembly, in accordance with an embodiment of the present disclosure, illustrating a connection thereof with an end effector or reload.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is a handheld surgical device in the form of a powered electromechanical handle assembly configured for selective attachment thereto of a plurality of different reloads, via a plurality of respective adapter assemblies, that are each configured for actuation and manipulation by the powered electromechanical handle assembly.

The surgical device includes a handle assembly 100 which is configured for selective connection with an adapter assembly 200, and, in turn, adapter assembly 200 is configured for selective connection with a selected reload 400 (of a plurality of reloads), which are configured to produce a surgical effect on tissue of a patient.

As illustrated in FIGS. 1-11, handle assembly 100 includes a power handle 101, and an outer shell housing 10 configured to selectively receive and encase power handle 101. Outer shell housing 10 includes a distal half-section 10a and a proximal half-section 10b pivotably connected to distal half-section 10a by a hinge 16 located along an upper edge of distal half-section 10a and proximal half-section 10b. When joined, distal and proximal half-sections 10a, 10b define a shell cavity 10c therein in which power handle 101 is selectively situated.

Distal and proximal half-sections 10a, 10b of shell housing 10 are divided along a plane that traverses a longitudinal axis "X" of adapter assembly 200.

Each of distal and proximal half-sections 10a, 10b of shell housing 10 includes a respective upper shell portion 12a, 12b, and a respective lower shell portion 14a, 14b. Lower shell portions 14a, 14b define a snap closure feature 18 for selectively securing lower shell portions 14a, 14b to one another and for maintaining shell housing 10 in a closed condition. Shell housing 10 includes right-side and left-side snap closure features 18a for further securing distal and proximal half-sections 10a, 10b of shell housing 10 to one another.

Distal half-section 10a of shell housing 10 defines a connecting portion 20 configured to accept a corresponding drive coupling assembly 210 of Adapter assembly 200. Specifically, distal half-section 10a of shell housing 10 has a recess 20 that receives a portion of drive coupling assembly 210 of Adapter assembly 200 when Adapter assembly 200 is mated to handle assembly 100.

Connecting portion 20 of distal half-section 10a defines a pair of axially extending guide rails 20a, 20b projecting radially inward from inner side surfaces thereof. Guide rails 20a, 20b assist in rotationally orienting Adapter assembly 200 relative to handle assembly 100 when Adapter assembly 200 is mated to handle assembly 100.

Connecting portion 20 of distal half-section 10a defines three apertures 22a, 22b, 22c formed in a distally facing surface thereof and which are arranged in a common plane or line with one another. Connecting portion 20 of distal half-section 10a also defines an elongate slot 24 (to contain connector 66, see FIG. 3) also formed in the distally facing surface thereof.

Connecting portion 20 of distal half-section 10a further defines a female connecting feature 26 (see FIG. 2) formed in a surface thereof. Female connecting feature 26 selectively engages with a male connecting feature of Adapter assembly 200, as will be described in greater detail below.

Distal half-section 10a of shell housing 10 supports a distal facing toggle control button 30. Toggle control button 30 is capable of being actuated in a left, right, up, and down direction upon application of a corresponding force thereto or a depressive force thereto.

Figure 2:
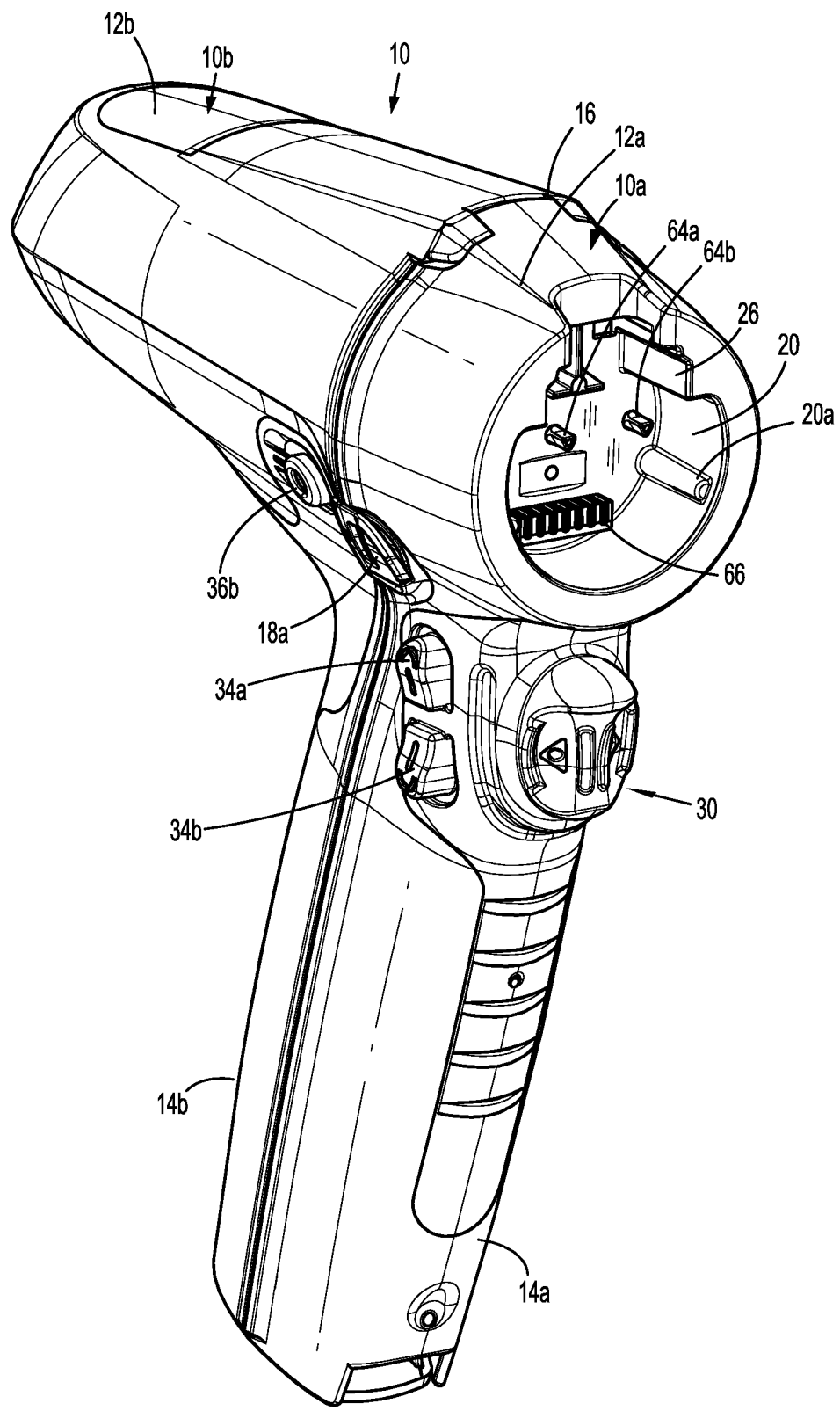
FIG. 2 is a front perspective view of a handle assembly of the surgical device of FIG. 1.

Distal half-section 10a of shell housing 10 supports a right-side pair of control buttons 32a, 32b (see FIG. 3); and a left-side pair of control button 34a, 34b (see FIG. 2). Right-side control buttons 32a, 32b and left-side control buttons 34a, 34b are capable of being actuated upon application of a corresponding force thereto or a depressive force thereto.

Proximal half-section 10b of shell housing 10 supports a right-side fire button 36a (see FIG. 3) and a left-side fire button 36b (see FIG. 2). Right-side fire button 36a and left-side fire button 36b are capable of being actuated upon application of a corresponding force thereto or a depressive force thereto.

Distal half-section 10a and proximal half-section 10b of shell housing 10 are fabricated from a polycarbonate, and are clear or transparent or may be overmolded.

With reference to FIGS. 5-11, handle assembly 100 includes an insertion guide 50 that is configured and shaped to seat on and entirely surround a distal facing edge 10d (FIGS. 3 and 9) of proximal half-section 10b. Insertion guide 50 includes a body portion 52 defining a central opening therein, and a hand/finger grip tab 54 extending from a bottom of body portion 52.

In use, when body portion 52 of insertion guide 50 is seated on distal facing edge 10d of proximal half-section 10b, the central opening of insertion guide 50 provides access to shell cavity 10c of shell housing 10 for insertion of a non-sterile power handle 101 of handle assembly 100 into proximal half-section 10b of sterile shell housing 10.

Figure 3:
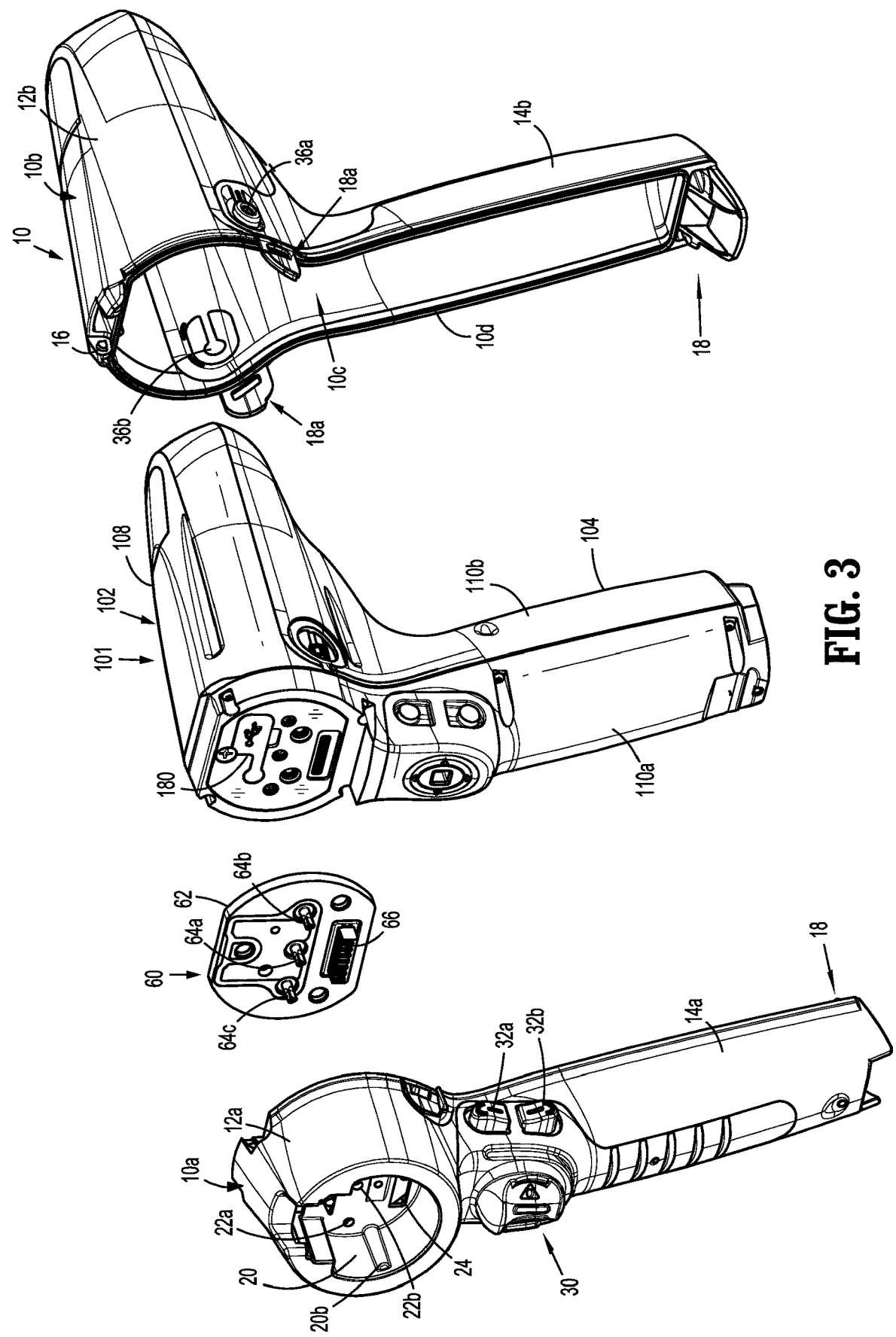
FIG. 3 is a front, perspective view, with parts separated, of the handle assembly of FIG. 2.
Figure 4:
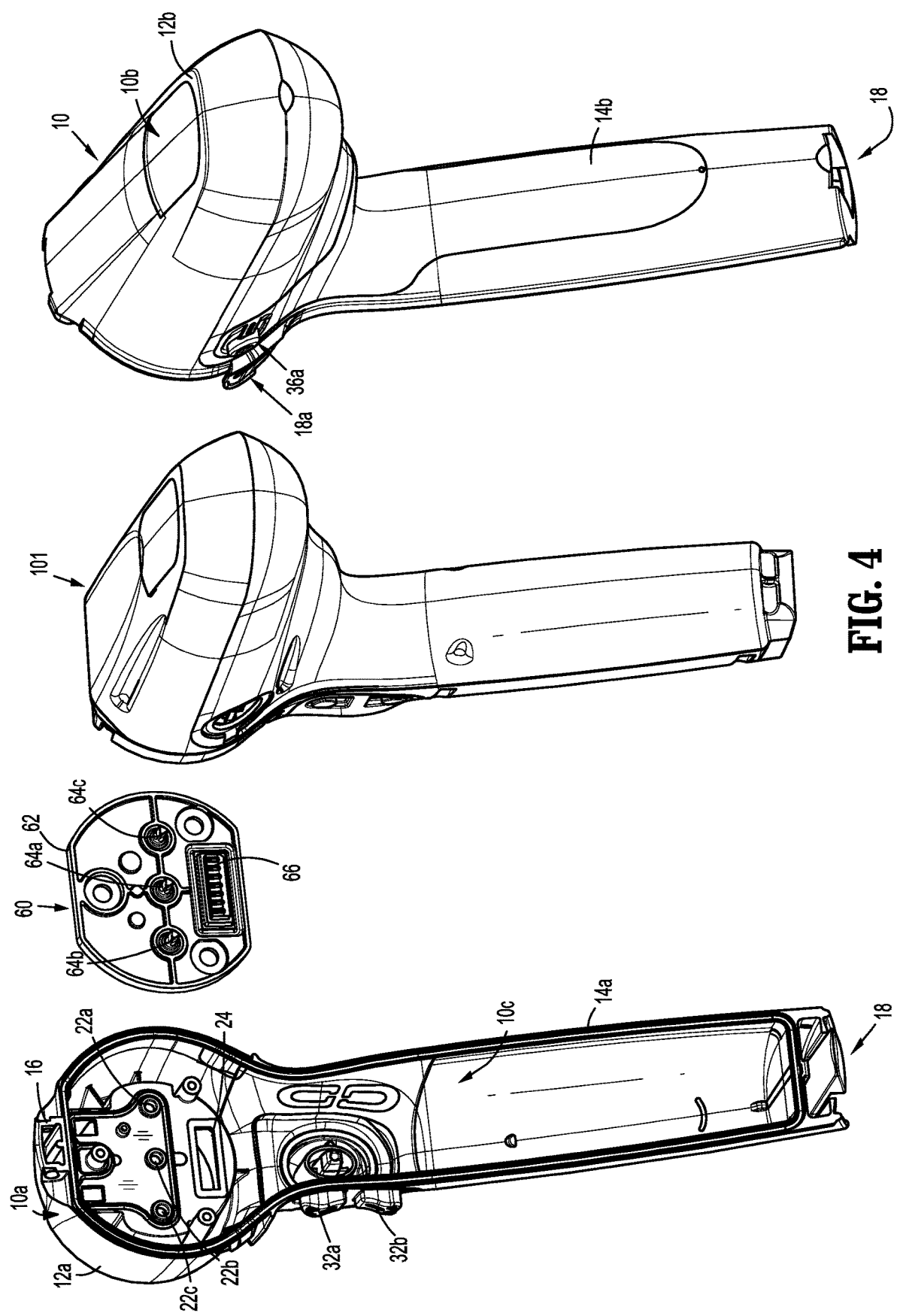
FIG. 4 is a rear, perspective view, with parts separated, of the handle assembly of FIG. 2.
Figure 6:
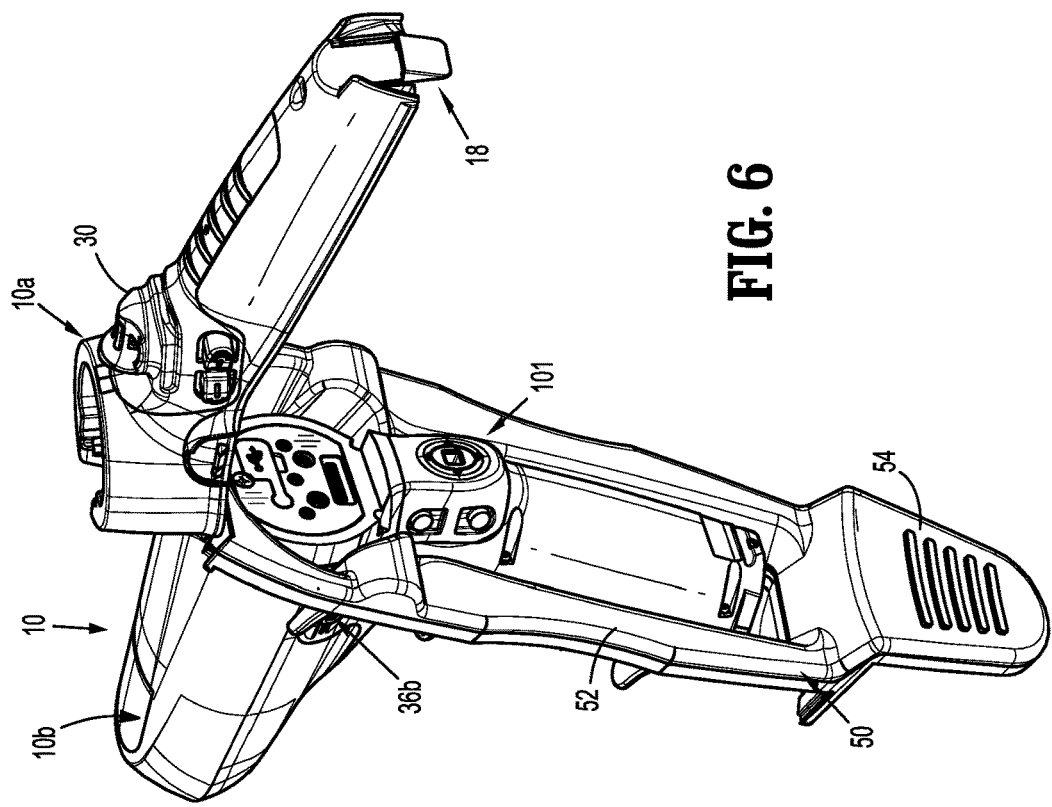
FIG. 6 is a perspective view illustrating the handle assembly inserted in a proximal half-section of the outer shell housing assembly, in accordance with the present disclosure.
Figure 5:
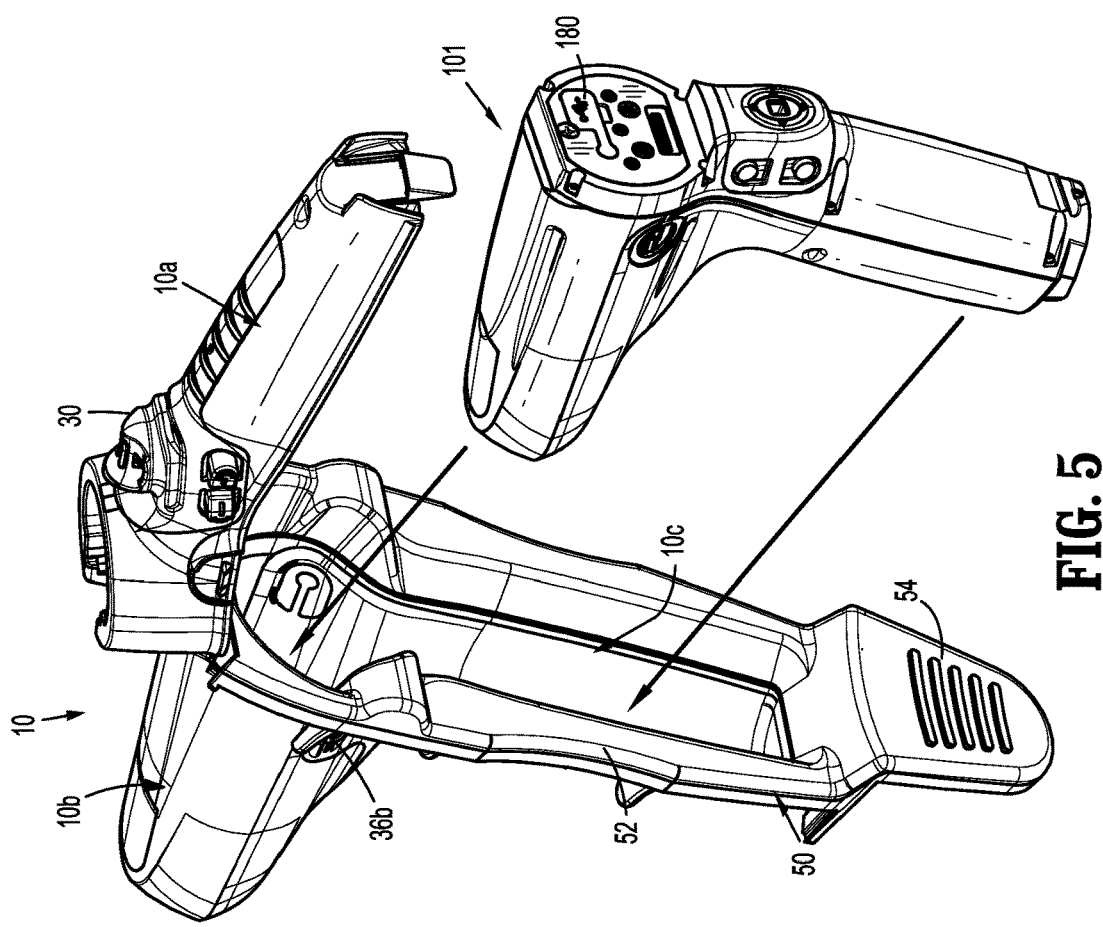
FIG. 5 is a perspective view illustrating an insertion of the handle assembly into an outer shell housing assembly, in accordance with the present disclosure.
Figure 7:
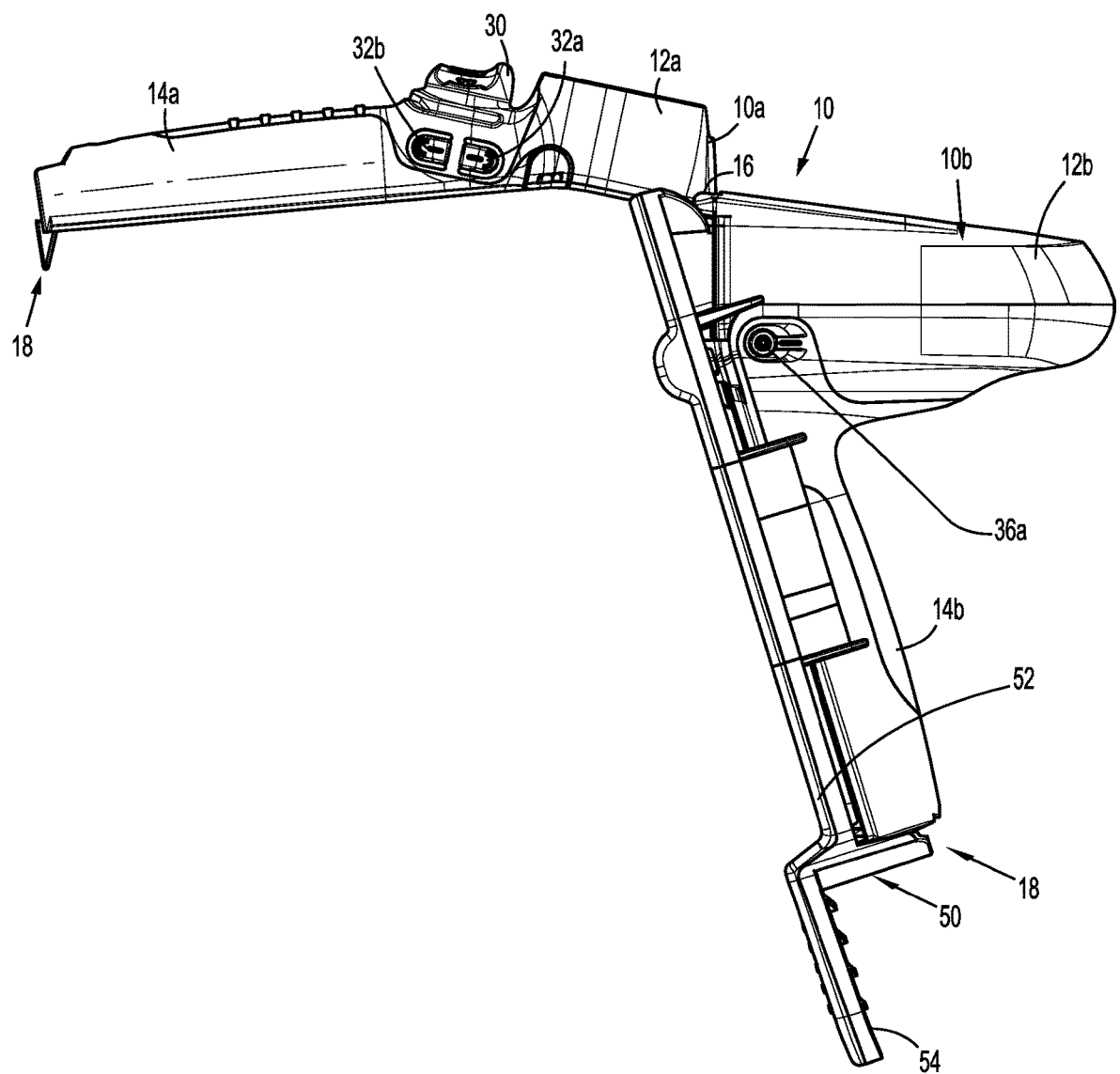
FIG. 7 is a side, elevational view of the outer shell housing, shown in an open condition.
Figure 10:
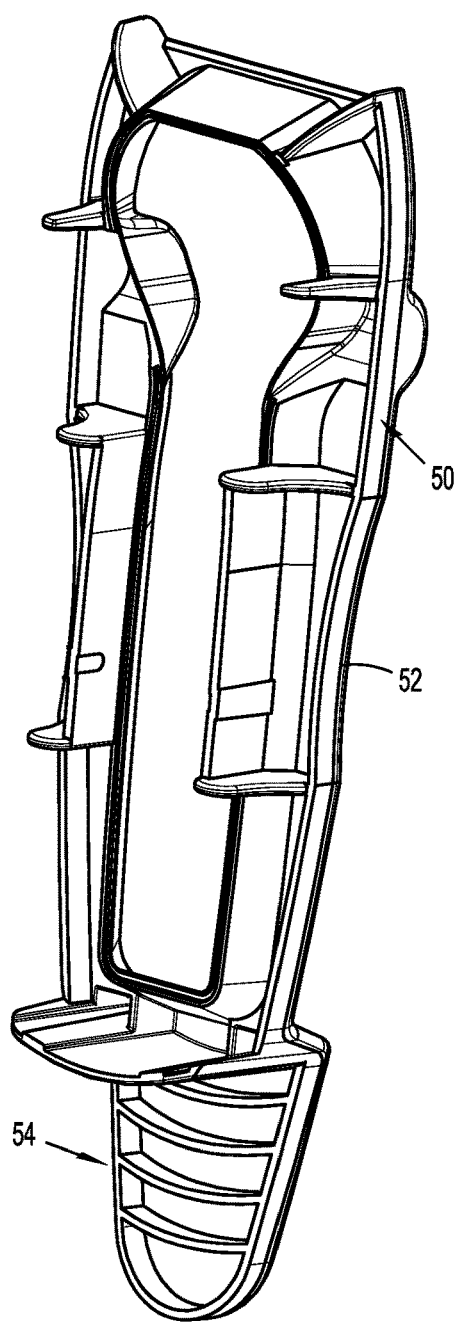
FIG. 10 is a rear, perspective view of the insertion guide.
Figure 11:
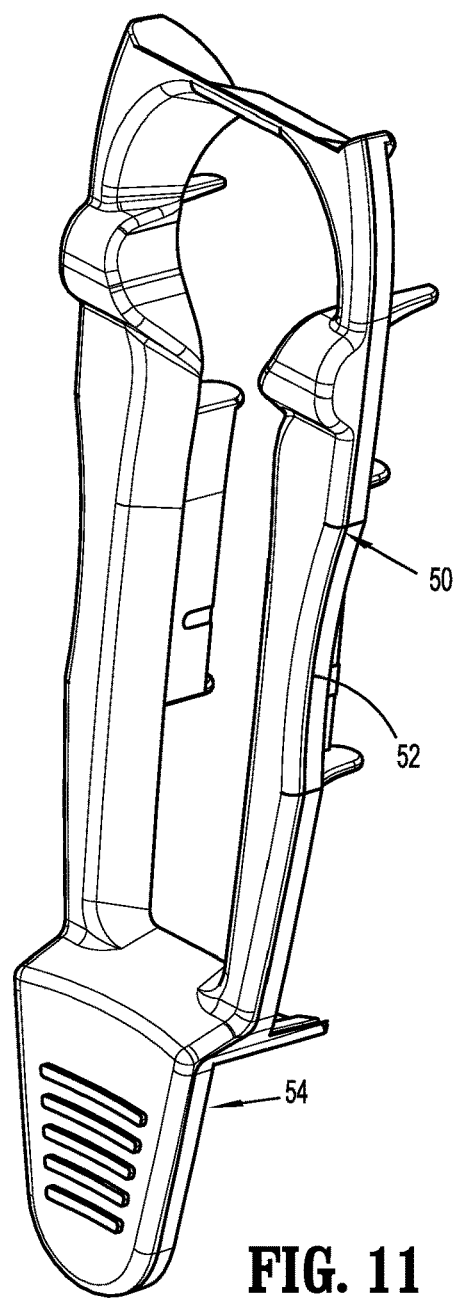
FIG. 11 is a front, perspective view of the insertion guide.

With reference to FIGS. 2-4, shell housing 10 includes a sterile barrier plate assembly 60 selectively supported in distal half-section 10a. Specifically, sterile barrier plate assembly 60 is disposed behind connecting portion 20 of distal half-section 10a and within shell cavity 10c of shell housing 10. Plate assembly 60 includes a plate 62 rotatably supporting three coupling shafts 64a, 64b, 64c. Each coupling shaft 64a, 64b, 64c extends from opposed sides of plate 62 and has a tri-lobe transverse cross-sectional profile. Each coupling shaft 64a, 64b, 64c extends through a respective aperture 22b, 22c, 22a of connecting portion 20 of distal half-section 10a when sterile barrier plate assembly 60 is disposed within shell cavity 10c of shell housing 10.

Plate assembly 60 further includes an electrical connector 66 supported on plate 62. Electrical connector 66 extends from opposed sides of plate 62. Each coupling shaft 64a, 64b, 64c extends through respective aperture 22a, 22b, 22c of connecting portion 20 of distal half-section 10a of shell housing 10 when sterile barrier plate assembly 60 is disposed within shell cavity 10c of shell housing 10. Electrical connector 66 includes a chip and defines a plurality of contact paths each including an electrical conduit for extending an electrical connection across plate 62.

When plate assembly 60 is disposed within shell cavity 10c of shell housing 10, distal ends of coupling shaft 64a, 64b, 64c and a distal end of pass-through connector 66 are disposed or situated within connecting portion 20 of distal half-section 10a of shell housing 10, and electrically and/or mechanically engage respective corresponding features of Adapter assembly 200, as will be described in greater detail below.

In operation, with a new and/or sterile shell housing 10 in an open configuration (e.g., distal half-section 10a separated from proximal half-section 10b, about hinge 16), and with insertion guide 50 in place against the distal edge 10d of proximal half-section 10b of shell housing 10, power handle 101 is inserted through the central opening of insertion guide 50 and into shell cavity 10c of shell housing 10. With power handle 101 inserted into shell cavity 10c of shell housing 10, insertion guide 50 is removed from proximal half-section 10b and distal half-section 10a is pivoted, about hinge 16, to a closed configuration for shell housing 10. In the closed configuration, snap closure feature 18 of lower shell portion 14a of distal half-section 10a engages snap closure feature 18 of lower shell portion 14b of proximal half-section 10b. Also, right-side and left-side snap closure features 18a engage to further maintain shell housing 10 in the closed configuration.

In operation, following a surgical procedure, snap closure feature 18 of lower shell portion 14a of distal half-section 10a is disengaged from snap closure feature 18 of lower shell portion 14b of proximal half-section 10b, and right-side and left-side snap closure features 18a are disengaged, such that distal half-section 10a may be pivoted, about hinge 16, away from proximal half-section 10b to open shell housing 10. With shell housing 10 open, power handle 101 is removed from shell cavity 10c of shell housing 10 (specifically from proximal half-section 10b of shell housing 10), and shell housing 10 is discarded.

Power handle 101 is then disinfected and cleaned. Power handle 101 is not to be submerged and is not to be sterilized.

Referring to FIGS. 3-6 and FIGS. 12-19, handle assembly 100 includes a power handle 101. Power handle 101 includes an inner handle housing 110 having a lower housing portion 104 and an upper housing portion 108 extending from and/or supported on lower housing portion 104. Lower housing portion 104 and upper housing portion 108 are separated into a distal half-section 110a and a proximal half-section 110b connectable to distal half-section 110a by a plurality of fasteners. When joined, distal and proximal half-sections 110a, 110b define an inner handle housing 110 having an inner housing cavity 110c therein in which a power-pack core assembly 106 is situated.

Power-pack core assembly 106 is configured to control the various operations of handle assembly 100, as will be set forth in additional detail below.

Distal half-section 110a of inner handle housing 110 defines a distal opening 111a therein which is configured and adapted to support a control plate 160 of power-pack core assembly 106. Control plate 160 of power handle 101 abuts against a rear surface of plate 62 of sterile barrier plate assembly 60 of shell housing 10 when power handle 101 is disposed within shell housing 10.

Figure 12:
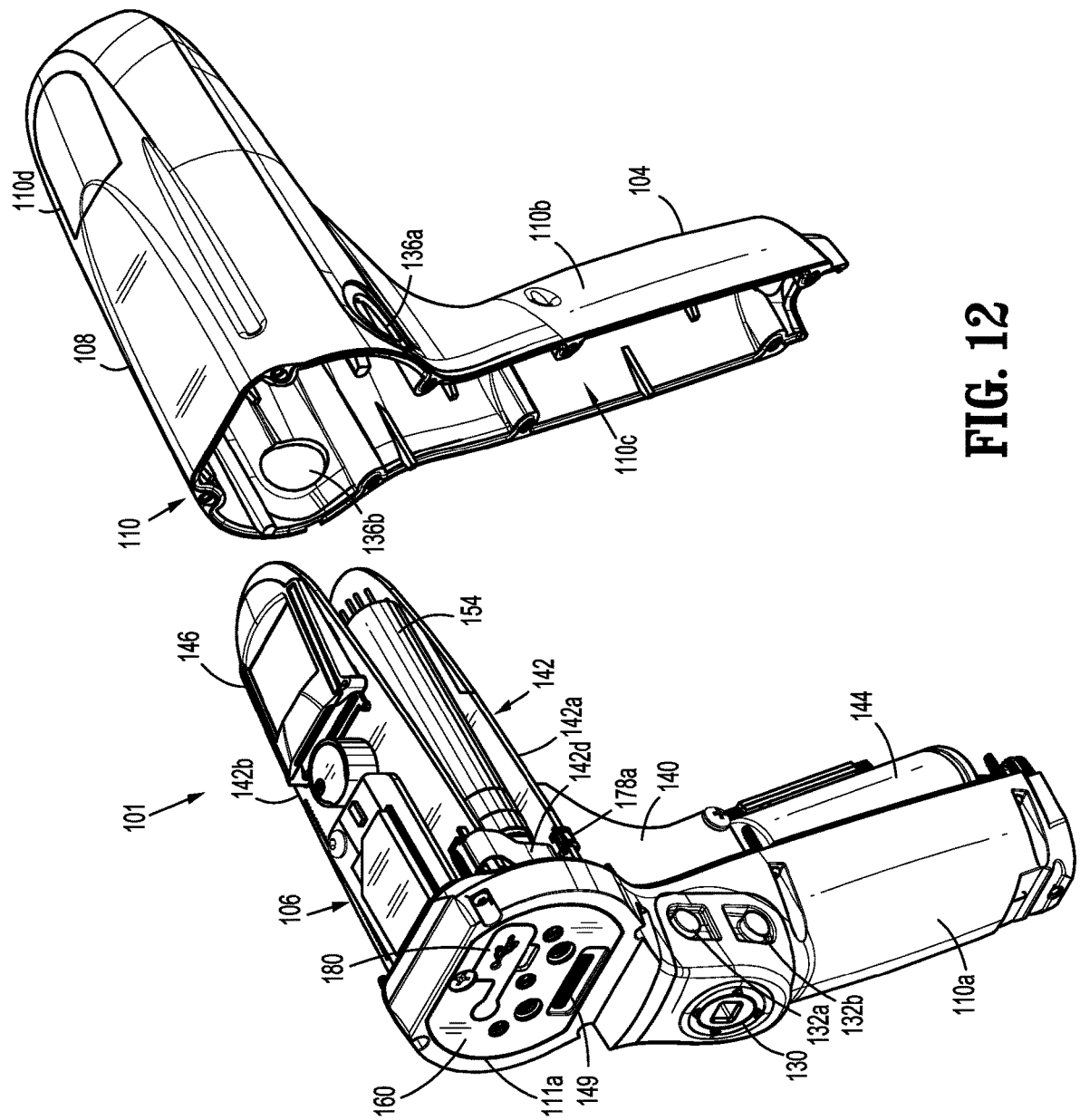
FIG. 12 is a front, perspective view of a power handle with an inner rear housing separated therefrom.
Figure 13:
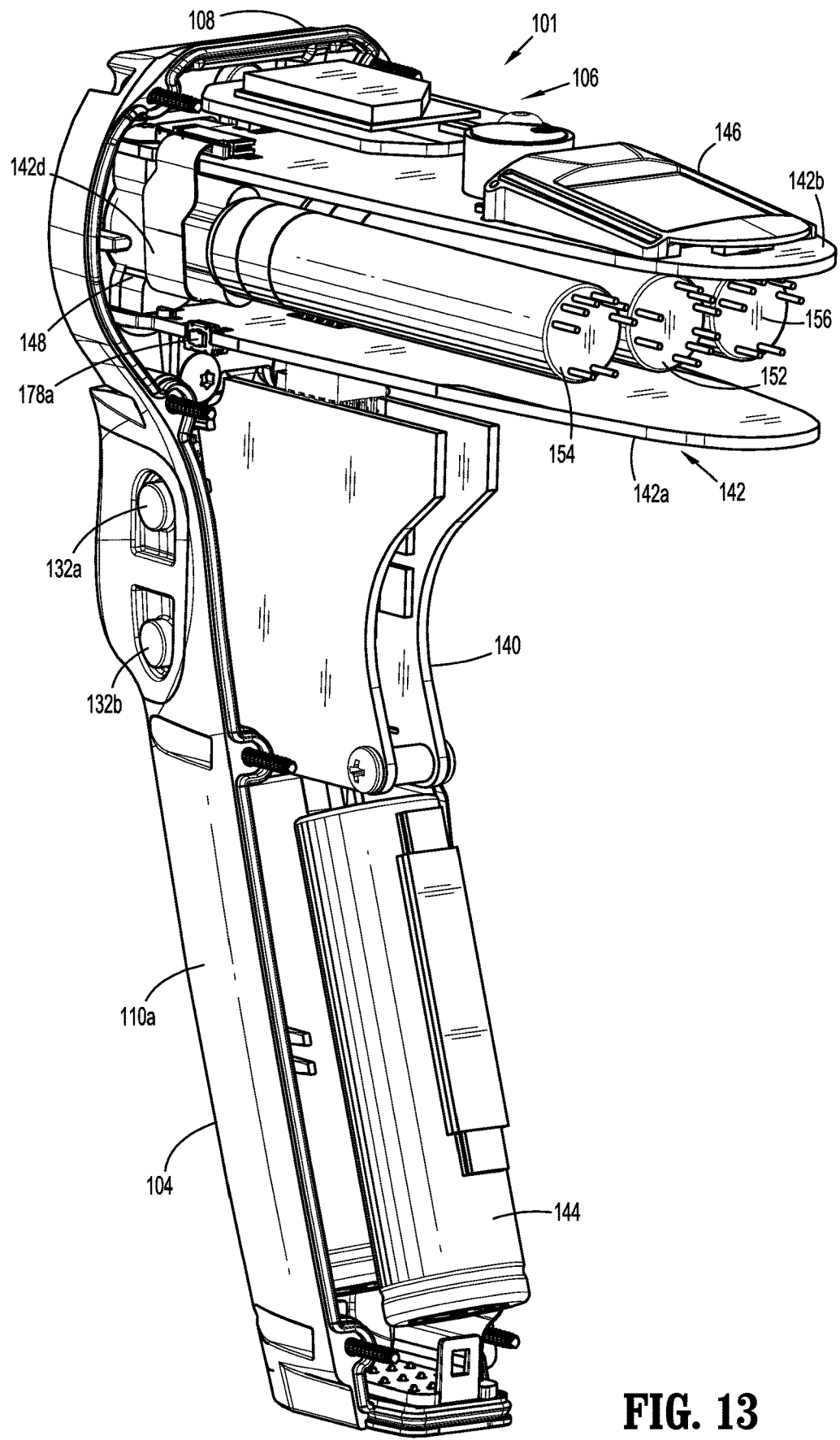
FIG. 13 is a rear, perspective view of the power handle with the inner rear housing removed therefrom.
Figure 15:
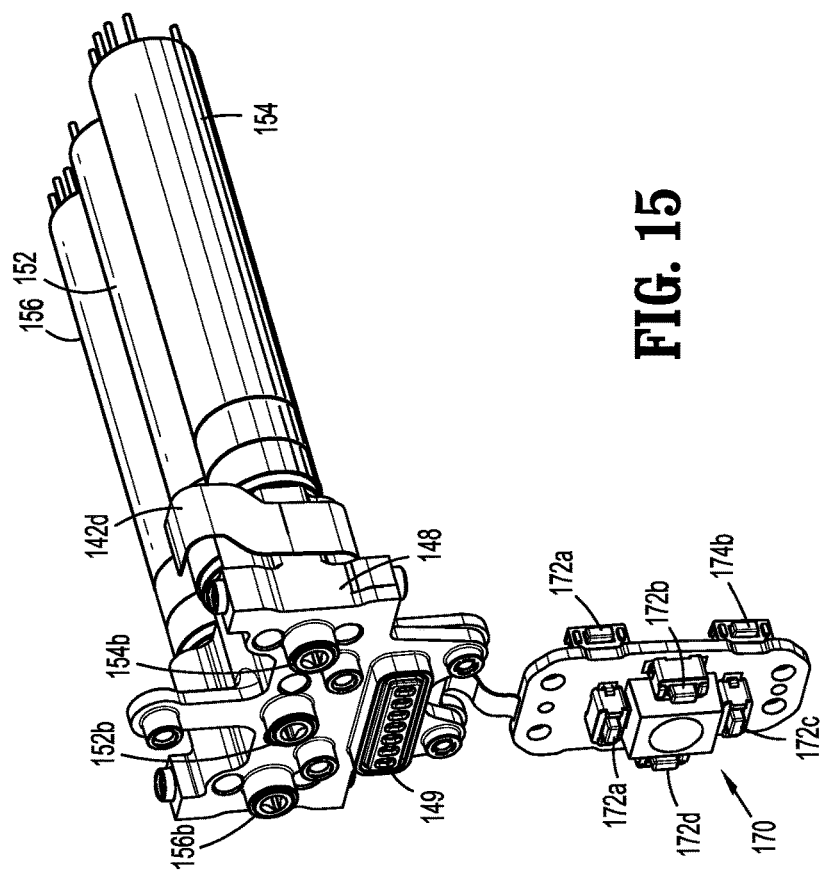
FIG. 15 is a front, perspective view of a motor assembly and a control assembly of the power handle core assembly of FIG. 14.

With reference to FIG. 12, distal half-section 110a of inner handle housing 110 supports a distal toggle control interface 130 that is in operative registration with distal toggle control button 30 of shell housing 10. In use, when power handle 101 is disposed within shell housing 10, actuation of toggle control button 30 exerts a force on toggle control interface 130.

Distal half-section 110a of inner handle housing 110 also supports a right-side pair of control interfaces 132a, 132b, and a left-side pair of control interfaces 134a, 134b. In use, when power handle 101 is disposed within shell housing 10, actuation of one of the right-side pair of control buttons 32a, 32b or the left-side pair of control button 34a, 34b of distal half-section 10a of shell housing 10 exerts a force on a respective one of the right-side pair of control interfaces 132a, 132b or the left-side pair of control interfaces 134a, 134b of distal half-section 110a of inner handle housing 110.

In use, control button 30, right-side fire button 36a or the left-side fire button 36b, the right-side pair of control interfaces 132a, 132b, and the left-side pair of control interfaces 134a, 134b of distal half-section 110a of inner handle housing 110 will be deactivated or fail to function unless shell housing 10 has been validated.

Proximal half-section 110b of inner handle housing 110 defines a right-side control aperture 136a and a left-side control aperture 136b. In use, when power handle 101 is disposed within shell housing 10, actuation of one of the right-side fire button 36a or the left-side fire button 36b of proximal half-section 10b of shell housing 10 extends the right-side fire button 36a or the left-side fire button 36b into and across the right-side control aperture 136a or the left-side control aperture 136b of the proximal half-section 110b of inner handle housing 110.

With reference to FIGS. 12-19, inner handle housing 110 provides a housing in which power-pack core assembly 106 is situated. Power-pack core assembly 106 includes a battery circuit 140, a controller circuit board 142 and a rechargeable battery 144 configured to supply power to any of the electrical components of handle assembly 100. Controller circuit board 142 includes a motor controller circuit board 142a, a main controller circuit board 142b, and a first ribbon cable 142c interconnecting motor controller circuit board 142a and main controller circuit board 142b.

Power-pack core assembly 106 further includes a display screen 146 supported on main controller circuit board 142b. Display screen 146 is visible through a clear or transparent window 110d (see FIGS. 12 and 17) provided in proximal half-section 110b of inner handle housing 110.

Power-pack core assembly 106 further includes a first motor 152, a second motor 154, and a third motor 156 each electrically connected to controller circuit board 142 and battery 144. Motors 152, 154, 156 are disposed between motor controller circuit board 142a and main controller circuit board 142b. Each motor 152, 154, 156 includes a respective motor shaft 152a, 154a, 156a extending therefrom. Each motor shaft 152a, 154a, 156a has a tri-lobe transverse cross-sectional profile for transmitting rotative forces or torque.

Each motor 152, 154, 156 is controlled by a respective motor controller. The motor controllers are disposed on motor controller circuit board 142a and are A3930/31K motor drivers from Allegro Microsystems, Inc. The A3930/31K motor drivers are designed to control a 3-phase brushless DC (BLDC) motor with N-channel external power MOSFETs, such as the motors 152, 154, 156. Each of the motor controllers is coupled to a main controller disposed on the main controller circuit board 142b. The main controller is also coupled to memory, which is also disposed on the main controller circuit board 142b. The main controller is an ARM Cortex M4 processor from Freescale Semiconductor, Inc, which includes 1024 kilobytes of internal flash memory. The main controller communicates with the motor controllers through an FPGA, which provides control logic signals (e.g., coast, brake, etc.). The control logic of the motor controllers then outputs corresponding energization signals to their respective motors 152, 154, 156 using fixed-frequency pulse width modulation (PWM).

Figure 16:
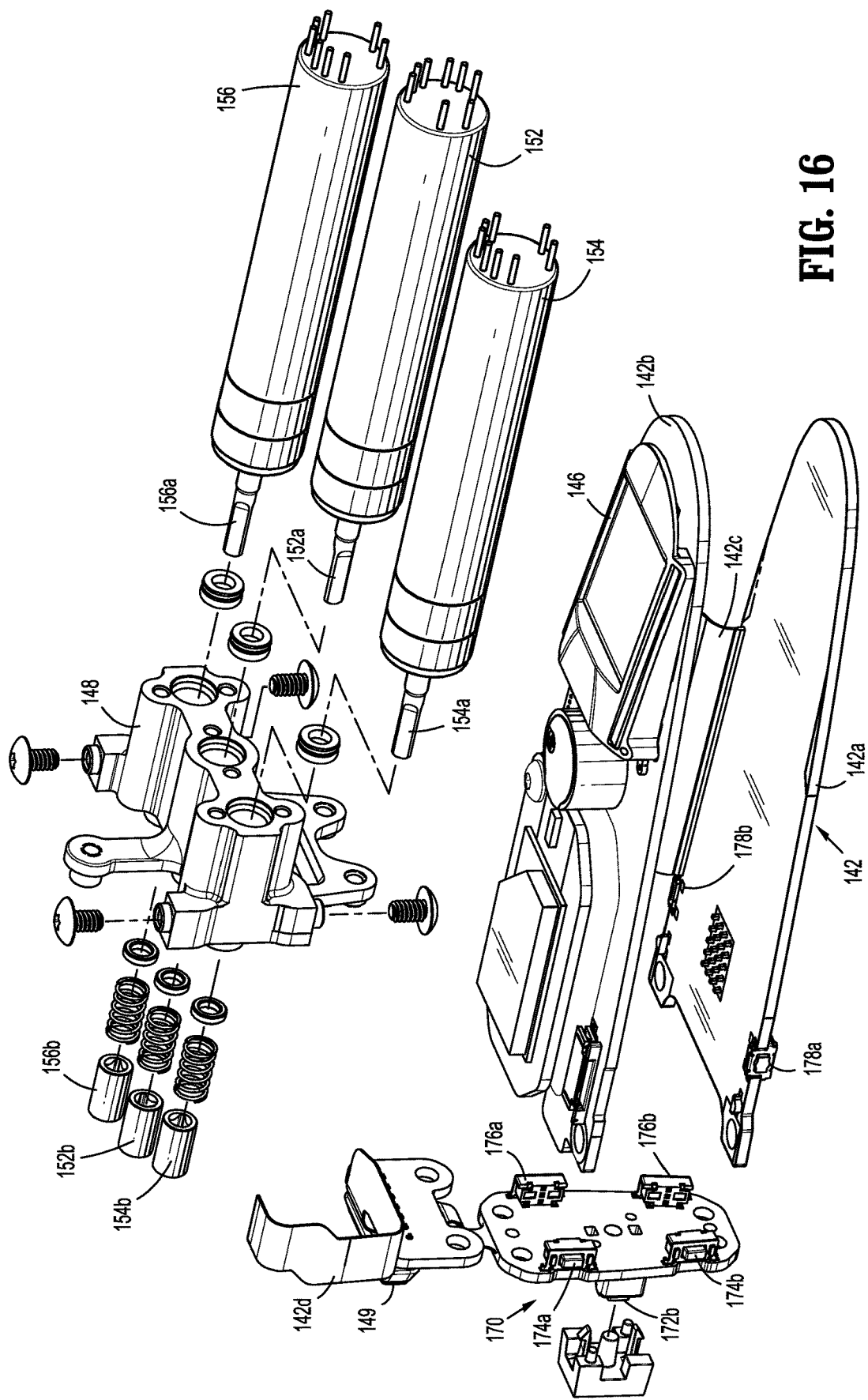
FIG. 16 is a rear, perspective view, with parts separated, of the motor assembly and the control assembly of FIG. 15.
Figure 17:
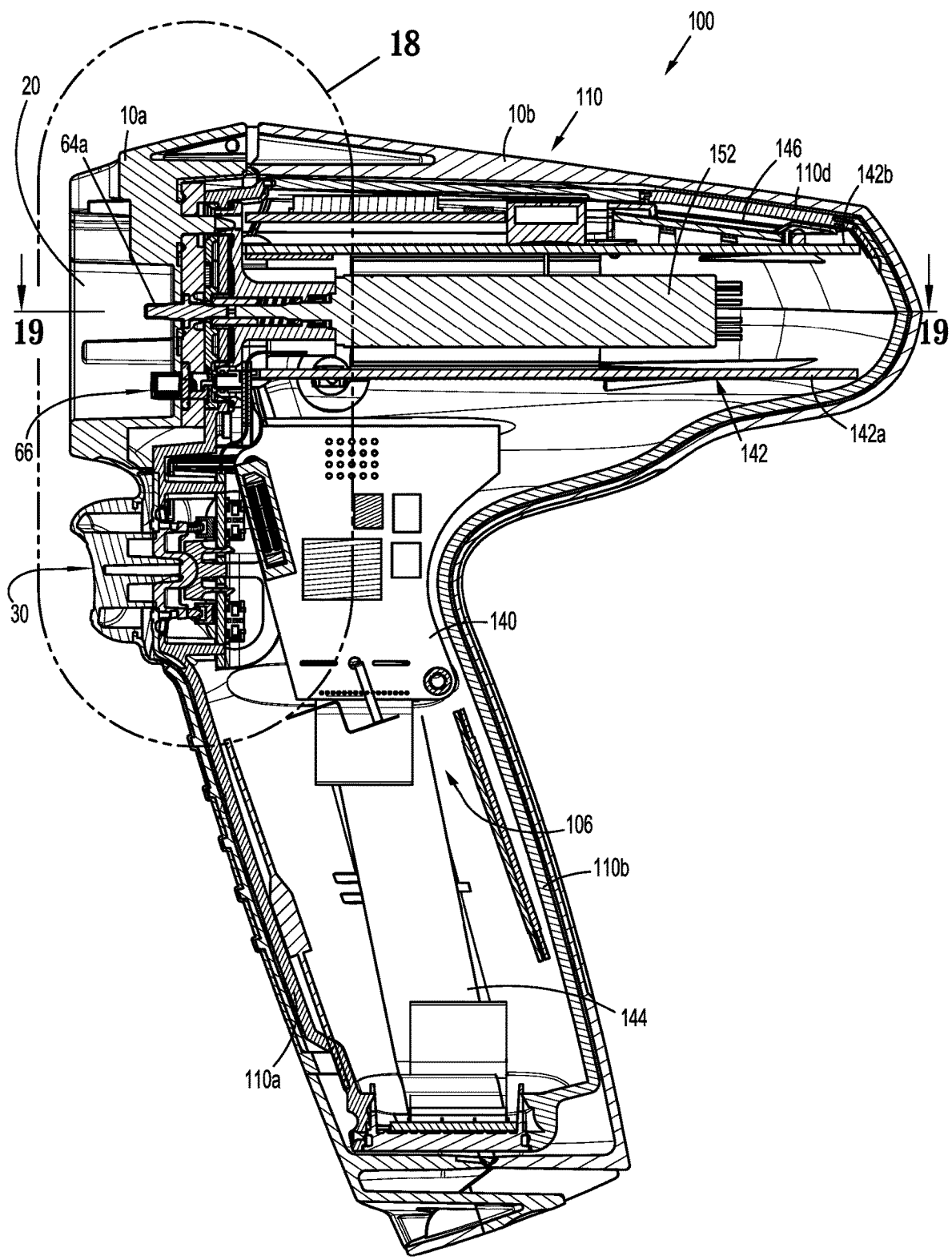
FIG. 17 is a longitudinal, cross-sectional view of the handle assembly of FIG. 2.
Figure 18:
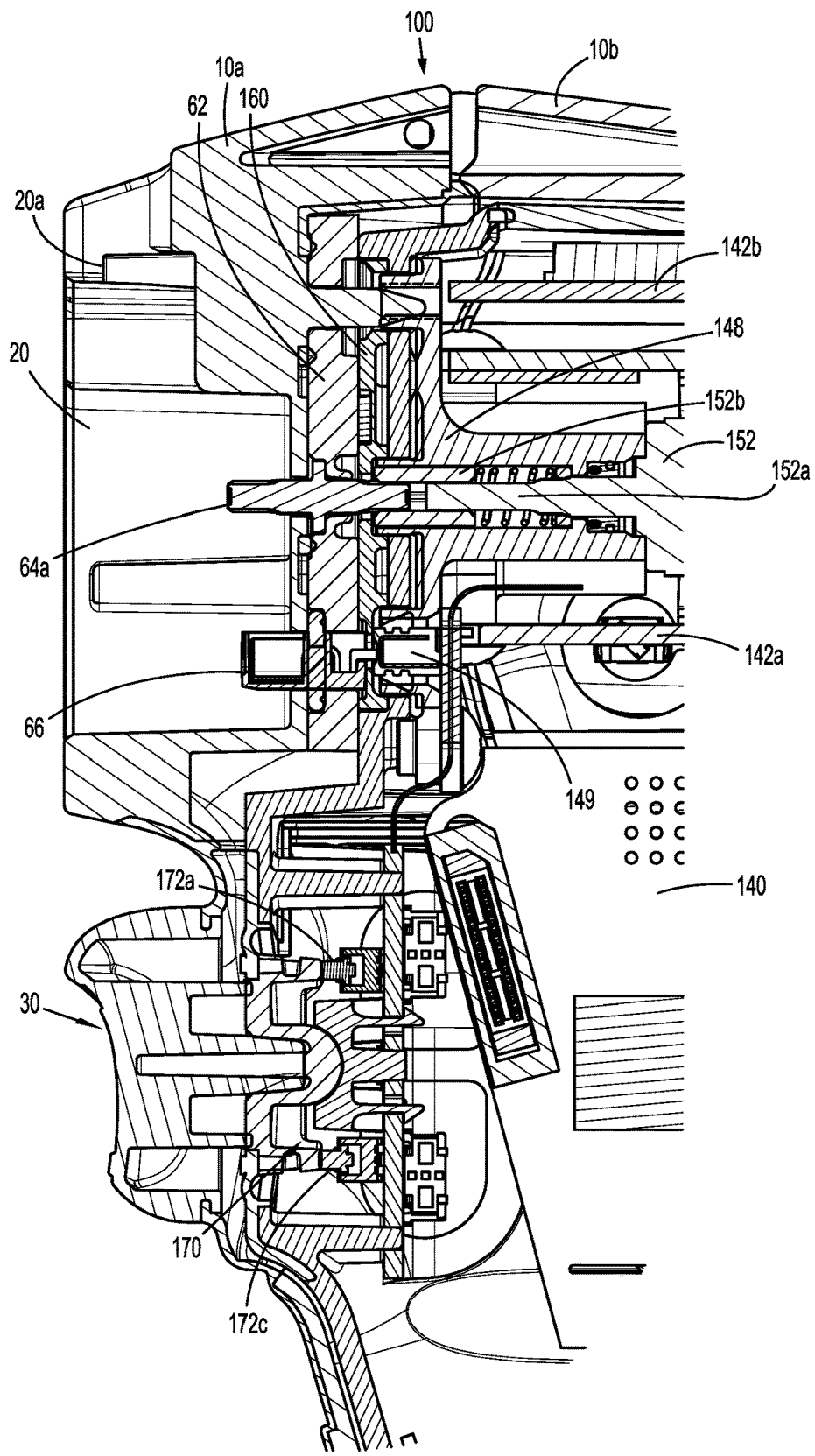
FIG. 18 is an enlarged view of the indicated area of detail of FIG. 17.
Figure 19:
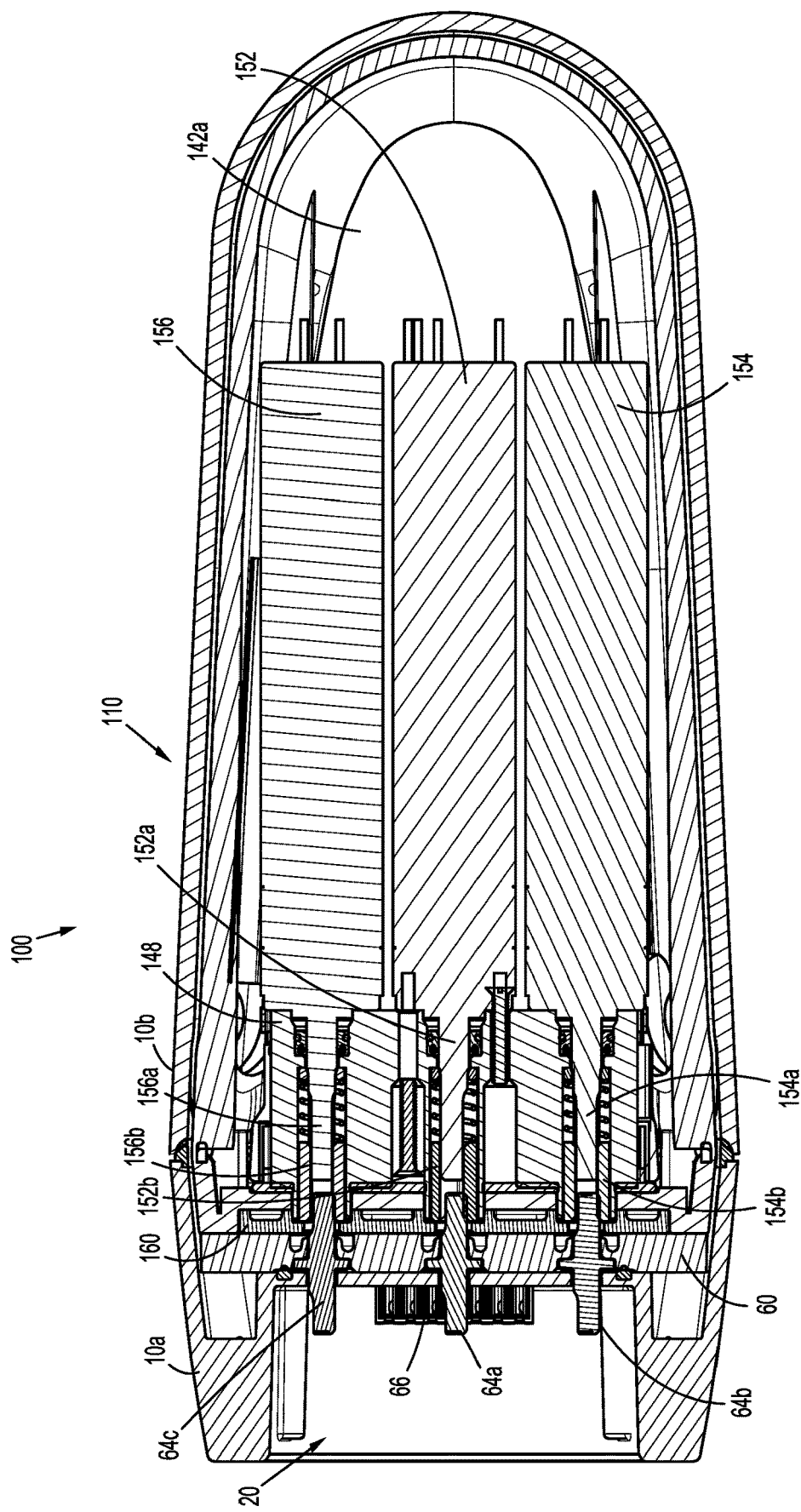
FIG. 19 is a cross-sectional view of the handle assembly as taken through 19-19 of FIG. 17.

Each motor 152, 154, 156 is supported on a motor bracket 148 such that motor shaft 152a, 154a, 156a are rotatably disposed within respective apertures of motor bracket 148. As illustrated in FIGS. 16 and 19, motor bracket 148 rotatably supports three rotatable drive connector sleeves 152b, 154b, 156b that are keyed to respective motor shafts 152a, 154a, 156a of motors 152, 154, 156. Drive connector sleeves 152b, 154b, 156b non-rotatably receive proximal ends of respective coupling shaft 64a, 64b, 64c of plate assembly 60 of shell housing 10, when power handle 101 is disposed within shell housing 10. Drive connector sleeves 152b, 154b, 156b are each spring biased away from respective motors 152, 154, 156.

Rotation of motor shafts 152a, 154a, 156a by respective motors 152, 154, 156 function to drive shafts and/or gear components of Adapter assembly 200 in order to perform the various operations of handle assembly 100. In particular, motors 152, 154, 156 of power-pack core assembly 106 are configured to drive shafts and/or gear components of adapter assembly 200 in order to selectively extend/retract a trocar member 274 of a trocar assembly 270 of adapter assembly 200; to, open/close reload 400 (when an anvil assembly 510 is connected to trocar member 274 of trocar assembly 270), to fire an annular array of staples of reload 400, and to fire an annular knife 444 of reload 400.

Motor bracket 148 also supports an electrical receptacle 149. Electrical receptacle 149 is in electrical connection with main controller circuit board 142b by a second ribbon cable 142d. Electrical receptacle 149 defines a plurality of electrical slots for receiving respective electrical contacts or blades extending from pass-through connector 66 of plate assembly 60 of shell housing 10.

Figure 22:
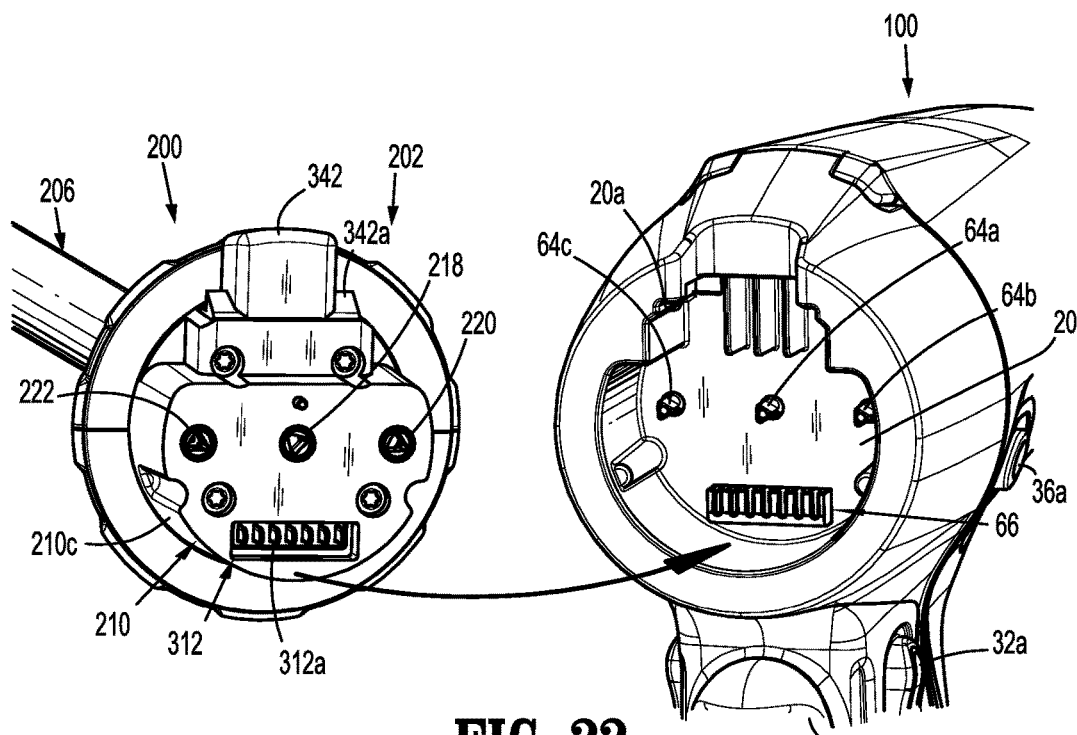
FIG. 22 is a perspective view illustrating a connection of the adapter assembly and the handle assembly.

In use, when adapter assembly 200 is mated to handle assembly 100, each of coupling shafts 64a, 64b, 64c of plate assembly 60 of shell housing 10 of handle assembly 100 couples with corresponding rotatable connector sleeves 218, 222, 220 of adapter assembly 200 (see FIG. 22). In this regard, the interface between corresponding first coupling shaft 64a and first connector sleeve 218, the interface between corresponding second coupling shaft 64b and second connector sleeve 222, and the interface between corresponding third coupling shaft 64c and third connector sleeve 220 are keyed such that rotation of each of coupling shafts 64a, 64b, 64c of handle assembly 100 causes a corresponding rotation of the corresponding connector sleeve 218, 222, 220 of adapter assembly 200.

The mating of coupling shafts 64a, 64b, 64c of handle assembly 100 with connector sleeves 218, 222, 220 of adapter assembly 200 allows rotational forces to be independently transmitted via each of the three respective connector interfaces. The coupling shafts 64a, 64b, 64c of handle assembly 100 are configured to be independently rotated by respective motors 152, 154, 156.

Since each of coupling shafts 64a, 64b, 64c of handle assembly 100 has a keyed and/or substantially non-rotatable interface with respective connector sleeves 218, 222, 220 of adapter assembly 200, when adapter assembly 200 is coupled to handle assembly 100, rotational force(s) are selectively transferred from motors 152, 154, 156 of handle assembly 100 to adapter assembly 200.

The selective rotation of coupling shaft(s) 64a, 64b, 64c of handle assembly 100 allows handle assembly 100 to selectively actuate different functions of reload 400. As will be discussed in greater detail below, selective and independent rotation of first coupling shaft 64a of handle assembly 100 corresponds to the selective and independent extending/retracting of trocar member 274 of adapter assembly 200 and/or the selective and independent opening/closing of reload 400 (when anvil assembly 510 is connected to trocar member 274). Also, the selective and independent rotation of third coupling shaft 64c of handle assembly 100 corresponds to the selective and independent firing of an annular array of staples of reload 400. Additionally, the selective and independent rotation of second coupling shaft 64b of handle assembly 100 corresponds to the selective and independent firing of an annular knife 444 of reload 400.

With reference to FIGS. 12-19, power-pack core assembly 106 further includes a switch assembly 170 supported within distal half-section 110a of inner handle housing 110, at a location beneath and in registration with toggle control interface 130, the right-side pair of control interfaces 132a, 132b, and the left-side pair of control interfaces 134a, 134b. Switch assembly 170 includes a first set of four push-button switches 172a-172d arranged around stem 30a of toggle control button 30 of outer shell housing 10 when power handle 101 is disposed within outer shell housing 10. Switch assembly 170 also includes a second pair of push-button switches 174a, 174b disposed beneath right-side pair of control interfaces 132a, 132b of distal half-section 110a of inner handle housing 110 when power handle 101 is disposed within outer shell housing 10. Switch assembly 170 further includes a third pair of push-button switches 176a, 176b disposed beneath left-side pair of control interfaces 134a, 134b of distal half-section 110a of inner handle housing 110 when power handle 101 is disposed within outer shell housing 10.

Power-pack core assembly 106 includes a single right-side push-button switch 178a disposed beneath right-side control aperture 136a of proximal half-section 110b of inner handle housing 110, and a single left-side push-button switch 178b disposed beneath left-side control aperture 136b of proximal half-section 110b of inner handle housing 110. Push-button switches 178a, 178b are supported on controller circuit board 142. Push-button switches 178a, 178b are disposed beneath right-side fire button 36a and left-side fire button 36b of proximal half-section 10b of shell housing 10 when power handle 101 is disposed within outer shell housing 10.

The actuation of push button switch 172c of switch assembly 170 of power handle 101, corresponding to a downward actuation of toggle control button 30, causes controller circuit board 142 to provide appropriate signals to motor 152 to activate, to retract a trocar member 274 of adapter assembly 200 and/or to close handle assembly 100 (e.g., approximate anvil assembly 510 relative to reload 400).

The actuation of push button switch 172a of switch assembly 170 of power handle 101, corresponding to an upward actuation of toggle control button 30, causes controller circuit board 142 to activate, to advance trocar member 274 of adapter assembly 200 and/or to open handle assembly 100 (e.g., separate anvil assembly 510 relative to reload 400).

The actuation of fire switch 178a or 178b of power handle 101, corresponding to an actuation of right-side or left-side control button 36a, 36b, causes controller circuit board 142 to provide appropriate signals to motors 154 and 156 to activate, as appropriate, to fire staples of reload 400, and then to advance (e.g., fire) and retract an annular knife 444 of reload 400.

The actuation of switches 174a, 174b (by right-hand thumb of user) or switches 176a, 176b (by left-hand thumb of user) of switch assembly 170, corresponding to respective actuation of right-side pair of control buttons 32a, 32b or left-side pair of control button 34a, 34b, causes controller circuit board 142 to provide appropriate signals to motor 152 to activate, to advance or retract trocar member 274 of adapter assembly 200.

Figure 14:
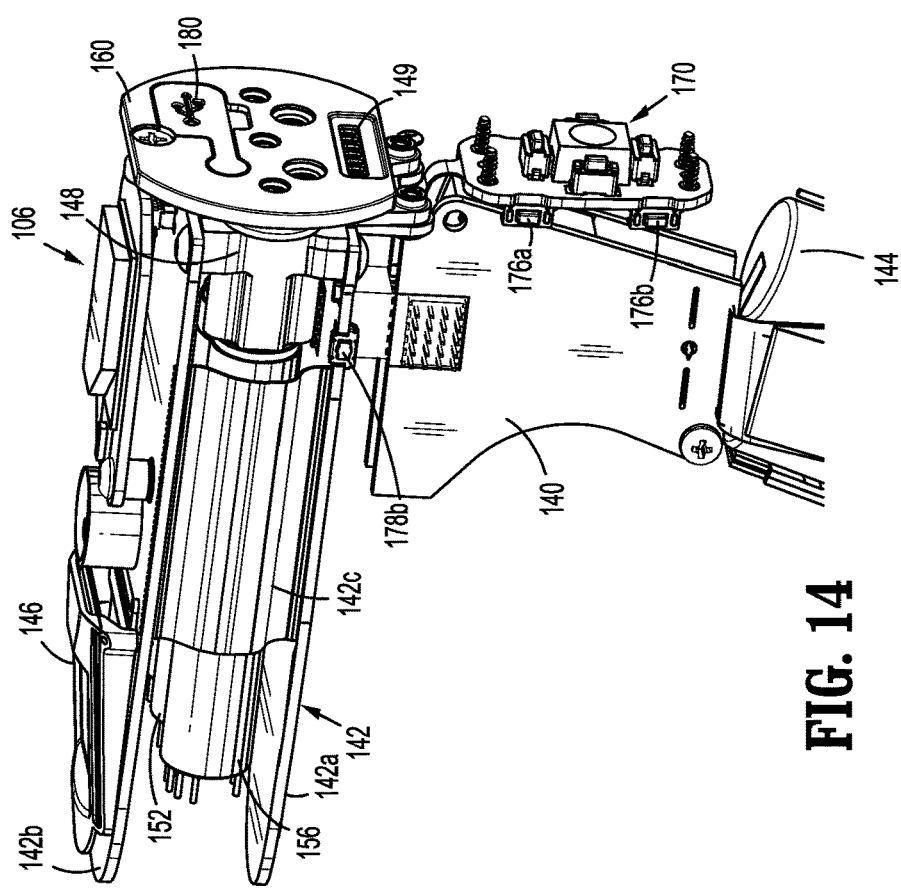
FIG. 14 is a perspective view of a power handle core assembly of the power handle.

With reference to FIGS. 12 and 14, power-pack core assembly 106 of handle assembly 100 includes a USB connector 180 supported on main controller circuit board 142b of controller circuit board 142. USB connector 180 is accessible through control plate 160 of power-pack core assembly 106. When power handle 101 is disposed within outer shell housing 10, USB connector 180 is covered by plate 62 of sterile barrier plate assembly 60 of shell housing 10.

As illustrated in FIG. 1 and FIGS. 20-65, handle assembly 100 is configured for selective connection with adapter assembly 200, and, in turn, adapter assembly 200 is configured for selective connection with reload 400.

Adapter assembly 200 is configured to convert a rotation of coupling shaft(s) 64a, 64b, 64c of handle assembly 100 into axial translation useful for advancing/retracting trocar member 274 of adapter assembly 200, for opening/closing handle assembly 100 (when anvil assembly 510 is connected to trocar member 274), for firing staples of reload 400, and for firing annular knife 444 of reload 400, as illustrated in FIG. 22, and as will be described in greater detail below.

Adapter assembly 200 includes a first drive transmitting/converting assembly for interconnecting first coupling shaft 64a of handle assembly 100 and an anvil assembly 510, wherein the first drive transmitting/converting assembly converts and transmits a rotation of first coupling shaft 64a of handle assembly 100 to an axial translation of trocar member 274 of trocar assembly 270, and in turn, the anvil assembly 510, which is connected to trocar member 274, to open/close handle assembly 100.

Adapter assembly 200 includes a second drive transmitting/converting assembly for interconnecting third coupling shaft 64c of handle assembly 100 and a second axially translatable drive member of reload 400, wherein the second drive transmitting/converting assembly converts and transmits a rotation of third coupling shaft 64c of handle assembly 100 to an axial translation of an outer flexible band assembly 255 of adapter assembly 200, and in turn, a driver adapter 432 of a staple driver assembly 430 of reload 400 to fire staples from a staple cartridge 420 of reload 400 and against anvil assembly 510.

Adapter assembly 200 includes a third drive transmitting/converting assembly for interconnecting second coupling shaft 64b of handle assembly 100 and a third axially translatable drive member of reload 400, wherein the third drive transmitting/converting assembly converts and transmits a rotation of second coupling shaft 64b of handle assembly 100 to an axial translation of an inner flexible band assembly 265 of adapter assembly 200, and in turn, a knife assembly 440 of reload 400 to fire annular knife 444 against anvil assembly 510.

Turning now to FIGS. 20-24, adapter assembly 200 includes an outer knob housing 202 and an outer tube 206 extending from a distal end of knob housing 202. Knob housing 202 and outer tube 206 are configured and dimensioned to house the components of adapter assembly 200. Knob housing 202 includes a drive coupling assembly 210 which is configured and adapted to connect to connecting portion 108 of handle housing 102 of handle assembly 100.

Adapter assembly 200 is configured to convert a rotation of either of first, second or third coupling shafts 64a, 64b, 64c, respectively, of handle assembly 100, into axial translations useful for operating trocar assembly 270 of adapter assembly 200, anvil assembly 510, and/or staple driver assembly 430 or knife assembly 440 of reload 400, as will be described in greater detail below.

As illustrated in FIGS. 57-61, adapter assembly 200 includes a proximal inner housing member 204 disposed within knob housing 202. Inner housing member 204 rotatably supports a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective coupling shafts 64a, 64c and 64b of handle assembly 100, as described in greater detail below.

As described briefly above, drive coupling assembly 210 of adapter assembly 200 is also configured to rotatably support first, second and third connector sleeves 218, 222 and 220, respectively, arranged in a common plane or line with one another. Each of connector sleeves 218, 220, 222 is configured to mate with respective first, second and third coupling shafts 64a, 64c and 64b of handle assembly 100, as described above. Each of connector sleeves 218, 220, 222 is further configured to mate with a proximal end of respective first, second and third proximal drive shafts 212, 214, 216 of adapter assembly 200.

Drive coupling assembly 210 of adapter assembly 200 also includes, as illustrated in FIGS. 26, 34, 35 and 40, a first, a second and a third biasing member 224, 226 and 228 disposed distally of respective first, second and third connector sleeves 218, 222, 220. Each of biasing members 224, 226 and 228 is disposed about respective first, second and third rotatable proximal drive shaft 212, 216 and 214. Biasing members 224, 226 and 228 act on respective connector sleeves 218, 222 and 220 to help maintain connector sleeves 218, 222 and 220 engaged with the distal end of respective coupling shafts 64a, 64b and 64c of handle assembly 100 when adapter assembly 200 is connected to handle assembly 100.

In particular, first, second and third biasing members 224, 226 and 228 function to bias respective connector sleeves 218, 222 and 220 in a proximal direction. In this manner, during connection of handle assembly 100 to adapter assembly 200, if first, second and or third connector sleeves 218, 222 and/or 220 is/are misaligned with coupling shafts 64a, 64b and 64c of handle assembly 100, first, second and/or third biasing member(s) 224, 226 and/or 228 are compressed. Thus, when handle assembly 100 is operated, coupling shafts 64a, 64c and 64b of handle assembly 100 will rotate and first, second and/or third biasing member(s) 224, 228 and/or 226 will cause respective first, second and/or third connector sleeve(s) 218, 220 and/or 222 to slide back proximally, effectively connecting coupling shafts 64a, 64c and 64b of handle assembly 100 to first, second and/or third proximal drive shaft(s) 212, 214 and 216 of drive coupling assembly 210.

As briefly mentioned above, adapter assembly 200 includes a first, a second and a third force/rotation transmitting/converting assembly 240, 250, 260, respectively, disposed within inner housing member 204 and outer tube 206. Each force/rotation transmitting/converting assembly 240, 250, 260 is configured and adapted to transmit or convert a rotation of a first, second and third coupling shafts 64a, 64c and 64b of handle assembly 100 into axial translations to effectuate operation of trocar assembly 270 of adapter assembly 200, and of staple driver assembly 430 or knife assembly 440 of reload 400.

As shown in FIGS. 25-28, first force/rotation transmitting/converting assembly 240 includes first rotatable proximal drive shaft 212, as described above, a second rotatable proximal drive shaft 281, a rotatable distal drive shaft 282, and a coupling member 286, each of which are supported within inner housing member 204, drive coupling assembly 210 and/or an outer tube 206 of adapter assembly 200. First force/rotation transmitting/converting assembly 240 functions to extend/retract trocar member 274 of trocar assembly 270 of adapter assembly 200, and to open/close handle assembly 100 (when anvil assembly 510 is connected to trocar member 274).

First rotatable proximal drive shaft 212 includes a non-circular or shaped proximal end portion configured for connection with first connector 218 which is connected to respective first coupling shaft 64a of handle assembly 100. First rotatable proximal drive shaft 212 includes a non-circular recess formed therein which is configured to key with a respective complimentarily shaped proximal end portion 281a of second rotatable proximal drive shaft 281. Second rotatable proximal drive shaft 281 includes a distal end portion 281b defining an oversized recess therein which is configured to receive a proximal end portion 282a of first rotatable distal drive shaft 282. Proximal end portion 282a of first rotatable distal drive shaft 282 is pivotally secured within the recess in distal end 281b of second rotatable proximal drive shaft 281 by a pin 283a received through the oversized recess in distal end portion 281b of second rotatable proximal drive shaft 281.

First rotatable distal drive shaft 282 includes a proximal end portion 282a, and a distal end portion 282b which is pivotally secured within a recess of coupling member 286. Distal end portion 282b of first rotatable distal drive shaft 282 is pivotally secured within a recess in a proximal end of coupling member 286 by a pin 283b received through the recess in the proximal end portion of coupling member 286. Proximal and distal end portions 282a, 282b of first rotatable distal drive shaft 282 define oversized openings for receiving pins 283a, 283b, respectively.

Coupling member 286 includes a proximal end 286a defining a recess 286c for receiving distal end portion 282b of first rotatable distal drive shaft 282, a distal end 286b defining a recess 286d for operably receiving a non-circular stem 276c on proximal end 276a of a drive screw 276 of trocar assembly 270.

Figure 73:
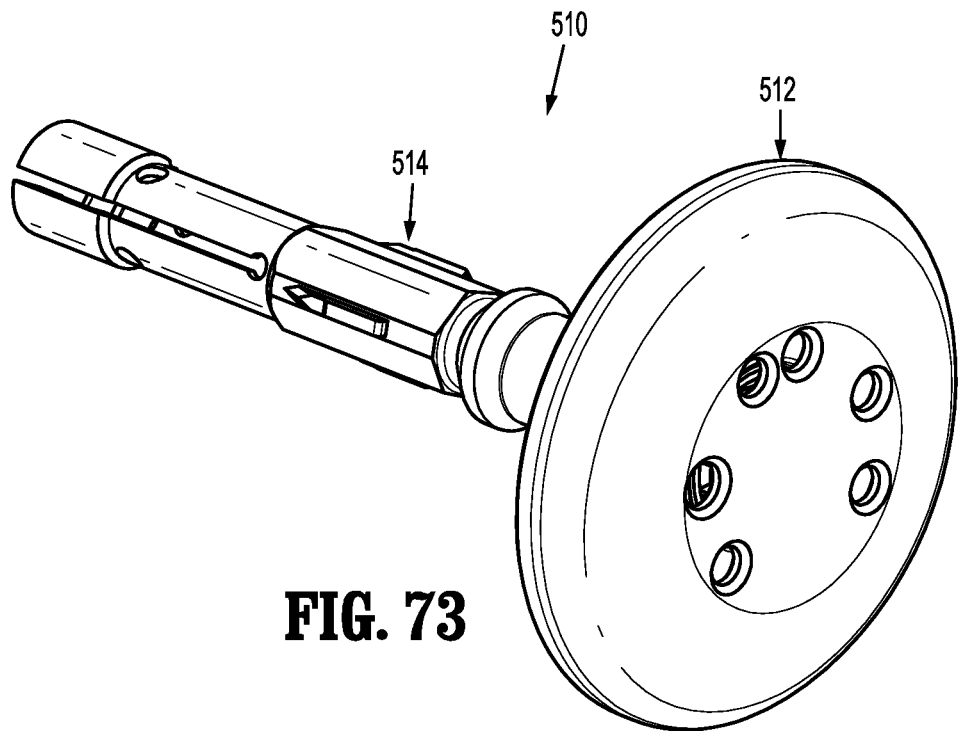
FIG. 73 is a front, perspective view of an anvil assembly of the present disclosure.
Figure 74:
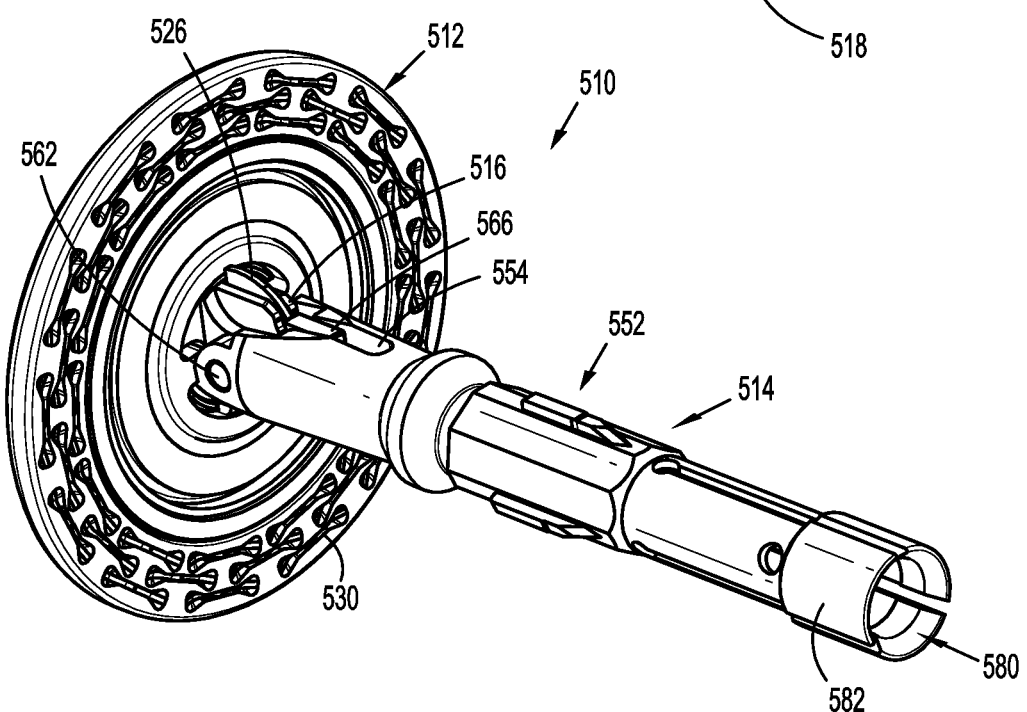
FIG. 74 is a rear, perspective view of the anvil assembly of FIG. 73.
Figure 75:
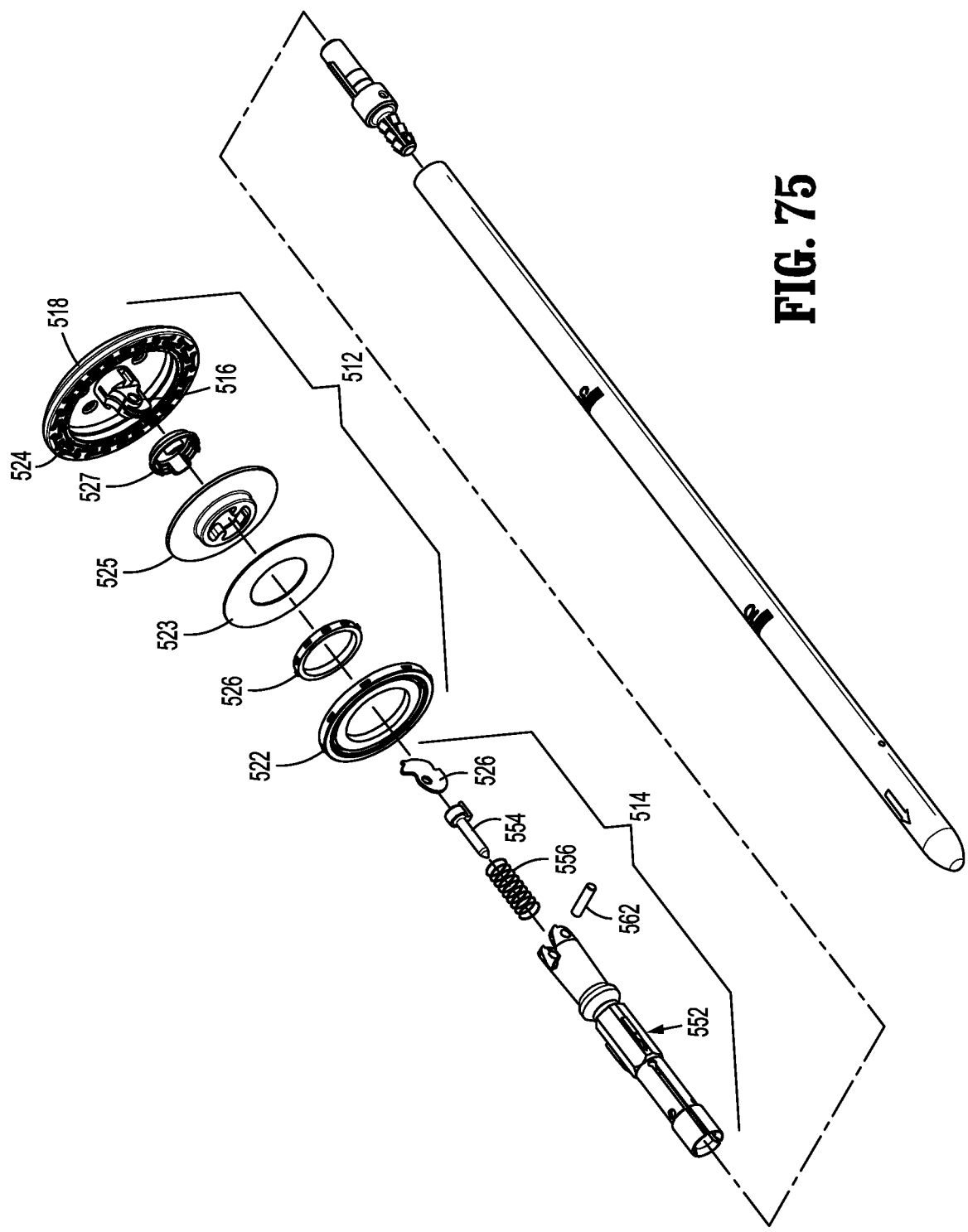
FIG. 75 is a perspective view, with parts separated, of the anvil assembly of FIGS. 73 and 74.
Figure 76:
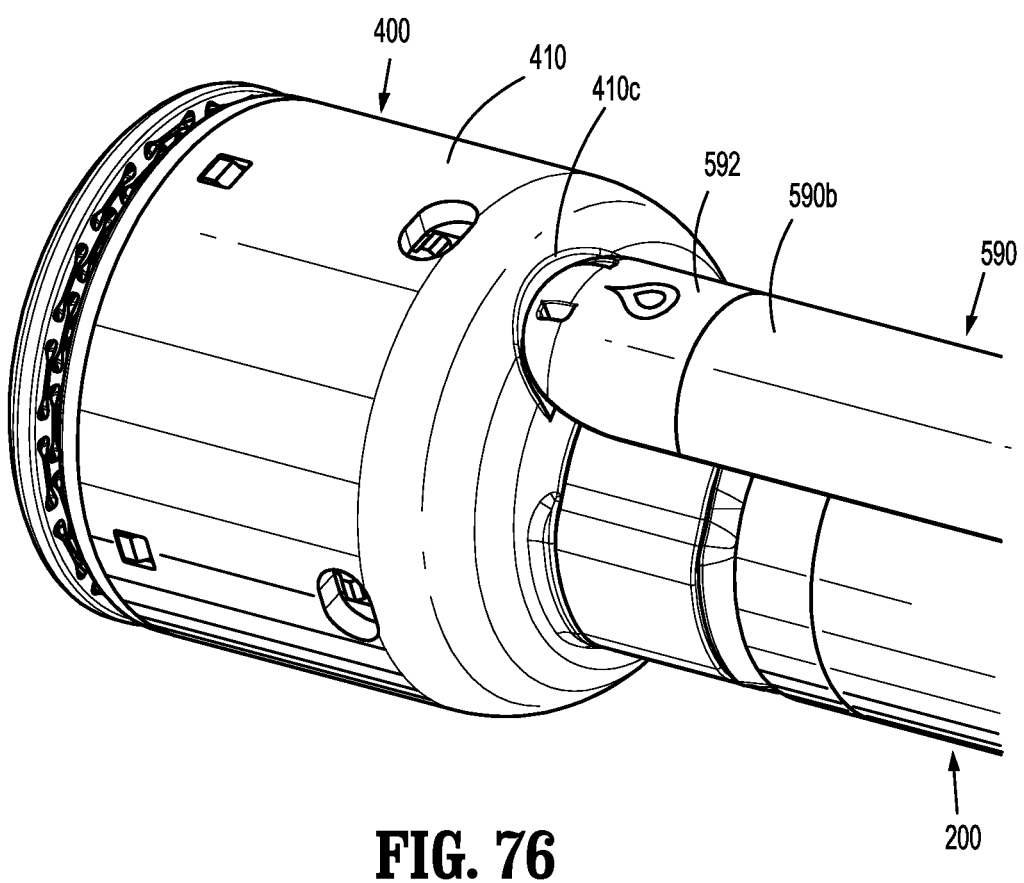
FIG. 76 is a rear, perspective view of the reload and more distal end portion of the adapter assembly, illustrating a connection of an irrigation tube thereto.
Figure 77:
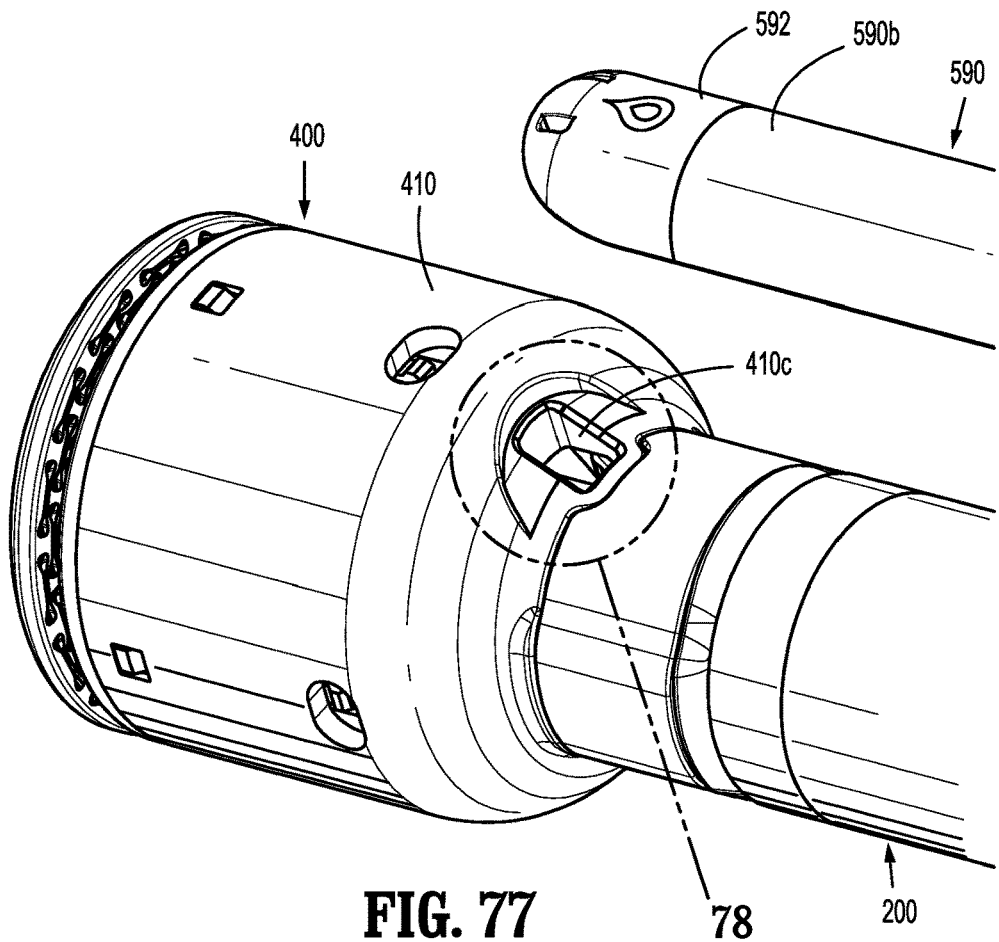
FIG. 77 is a rear, perspective view of the reload and more distal end portion of the adapter assembly, illustrating the irrigation tube separated therefrom.
Figure 78:
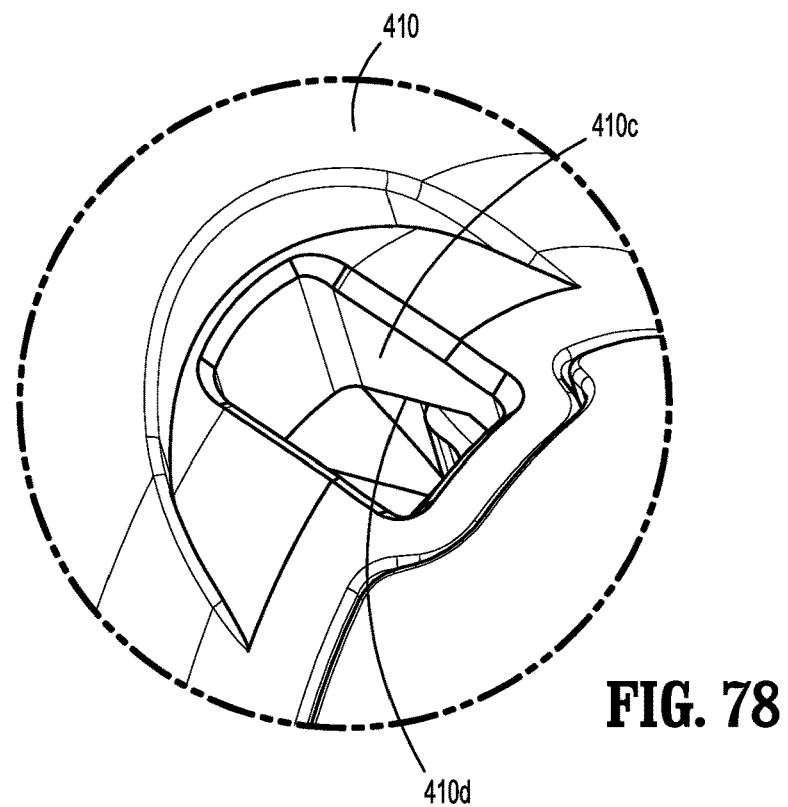
FIG. 78 is an enlarged view of the indicated area of detail of FIG. 77.

First force/rotation transmitting/converting assembly 240 further includes a trocar assembly 270 removably supported in a distal end of outer tube 206. Trocar assembly 270 includes an outer housing 272, a trocar member 274 slidably disposed within tubular outer housing 272, and a drive screw 276 operably received within trocar member 274 for axially moving trocar member 274 relative to tubular housing 272. In particular, trocar member 274 includes a proximal end 274a having an inner threaded portion which engages a threaded distal portion 276b of drive screw 276. Trocar member 274 further includes at least one longitudinally extending flat formed in an outer surface thereof which mates with a corresponding flat formed in tubular housing 272 thereby inhibiting rotation of trocar member 274 relative to tubular housing 272 as drive screw 276 is rotated. A distal end 274b of trocar member 274 is configured to selectively engage anvil assembly 510 (FIGS. 73-75).

Tubular housing 272 of trocar assembly 270 is axially and rotationally fixed within outer tube 206 of adapter assembly 200. Tubular housing 272 defines a pair of radially opposed, and radially oriented openings 272a which are configured and dimensioned to cooperate with a pair of lock pins 275c of a trocar assembly release mechanism 275. With reference to FIGS. 29-33, adapter assembly 200 includes a support block 292 fixedly disposed within outer tube 206. Support block 292 is disposed proximal of a connector sleeve 290 and proximal of a strain sensor 320a of a strain gauge assembly 320, as described in greater detail below. The pair of lock pins 275c extend through support block 292 and into tubular housing 272 of trocar assembly 270 to connect trocar assembly 270 to adapter assembly 200.

As illustrated in FIGS. 29-33, trocar assembly release mechanism 275 includes a release button 275a pivotally supported on support block 292 and in outer tube 206. Release button 275a is spring biased to a locked/extended condition. Trocar assembly release mechanism 275 further includes a spring clip 275b connected to release button 275a, wherein spring clip 275b includes a pair of legs that extend through support block 292 and transversely across trocar assembly 270. Each of the pair of legs of spring clip 275b extends through a respective lock pin 275c which is slidably disposed within a respective radial opening 272a of tubular housing 272 and radial opening 292a of support block 292 (see FIG. 31).

In use, when release button 275a is depressed (e.g., in a radially inward direction, FIG. 33), release button 275a moves spring clip 275b transversely relative to trocar assembly 270. As spring clip 275b is moved transversely relative to trocar assembly 270, the pair of legs of spring clip 275b translate through the pair of lock pins 275c such that a goose-neck in each leg acts to cam and urge the pair of lock pins 275c radially outward. Each of the pair of lock pins 275c is urged radially outward by a distance sufficient that each of the pair of lock pins 275c clears respective opening 272a of tubular housing 272. With the pair of lock pins 275c free and clear of tubular housing 272, trocar assembly 270 may be axially withdrawn from within the distal end of outer tube 206 of adapter assembly 200.

In operation, as first rotatable proximal drive shaft 212 is rotated, due to a rotation of first connector sleeve 218, as a result of the rotation of first coupling shaft 64a of handle assembly 100, second rotatable distal drive shaft 281 is caused to be rotated. Rotation of second rotatable distal drive shaft 281 results in contemporaneous rotation of first rotatable distal drive shaft 282. Rotation of first rotatable distal drive shaft 282 causes contemporaneous rotation of coupling member 286, which, in turn, causes contemporaneous rotation of drive screw 276 of trocar assembly 270. As drive screw 276 is rotated within and relative to trocar member 274, engagement of the inner threaded portion of trocar member 274 with threaded distal portion 276b of drive screw 276 causes axial translation of trocar member 274 within tubular housing 272 of trocar assembly 270. Specifically, rotation of drive screw 276 in a first direction causes axial translation of trocar member 274 in a first direction (e.g., extension of trocar assembly 270 of handle assembly 100), and rotation of drive screw 276 in a second direction causes axial translation of trocar member 274 in a second direction (e.g., retraction of trocar assembly 270 of handle assembly 100).

When anvil assembly 510 is connected to trocar member 274, as will be described in detail below, the axial translation of trocar member 274 in the first direction results in an opening of reload 400, and the axial translation of trocar member 274 in the second direction results in a closing of reload 400.

Forces during an actuation or trocar member 274 or a closing of reload 400 may be measured by strain sensor 320a of strain gauge assembly 320 in order to:
- determine a presence and proper engagement of trocar assembly 270 in adapter assembly 200;
- determine a presence of anvil assembly 510 during calibration;
- determine misalignment of the splines of trocar member 274 with longitudinally extending ridges 416 of reload 400;
- determine a re-clamping of a previously tiled anvil assembly 510;
- determine a presence of obstructions during clamping or closing of reload 400;
- determine a presence and connection of anvil assembly 510 with trocar member 274;
- monitor and control a compression of tissue disposed within reload 400;
- monitor a relaxation of tissue, over time, clamped within reload 400;
- monitor and control a firing of staples from reload 400;
- detect a presence of staples in reload 400;
- monitors forces during a firing and formation of the staples as the staples are being ejected from reload 400;
- optimize formation of the staples (e.g., staple crimp height) as the staples are being ejected from reload 400 for different indications of tissue;
- monitor and control a firing of annular knife 444 of reload 400;
- monitor and control a completion of the firing and cutting procedure; and
- monitor a maximum firing force and control the firing and cutting procedure to protect against exceeding a pre-determined maximum firing force.

In operation, strain sensor 320a of strain gauge assembly 320 of adapter assembly 200 measures and monitors the retraction of trocar member 274, as described above. During the closing of reload 400, if and when head assembly 512 of anvil assembly 510 contacts tissue, an obstruction, staple cartridge 420 or the like, a reaction force is exerted on head assembly 512 which is in a generally distal direction. This distally directed reaction force is communicated from head assembly 512 to center rod assembly 514 of anvil assembly 510, which in turn is communicated to trocar assembly 270. Trocar assembly 270 then communicates the distally directed reaction force to the pair of pins 275c of trocar assembly release mechanism 275, which in turn then communicate the reaction force to support block 292. Support block 292 then communicates the distally directed reaction force to strain sensor 320a of strain gauge assembly 320.

Strain sensor 320a of strain gauge assembly 320 is a device configured to measure strain (a dimensionless quantity) on an object that it is adhered to (e.g., support block 292), such that, as the object deforms, a metallic foil of the strain sensor 320a is also deformed, causing an electrical resistance thereof to change, which change in resistance is then used to calculate loads experienced by trocar assembly 270.

Strain sensor 320a of strain gauge assembly 320 then communicates signals to main controller circuit board 142b of power-pack core assembly 106 of handle assembly 100. Graphics are then displayed on display screen 146 of power-pack core assembly 106 of handle assembly 100 to provide the user with real-time information related to the status of the firing of handle assembly 100.

With reference to FIGS. 34-38, second force/rotation transmitting/converting assembly 250 of adapter assembly 200 includes second proximal drive shaft 214, as described above, a first coupling shaft 251, a planetary gear set 252, a staple lead screw 253, and a staple driver 254, each of which are supported within inner housing member 204, drive coupling assembly 210 and/or an outer tube 206 of adapter assembly 200. Second force/rotation transmitting/converting assembly 250 functions to fire staples of reload 400 for formation against anvil assembly 510.

Second rotatable proximal drive shaft 214 includes a non-circular or shaped proximal end portion configured for connection with second connector or coupler 220 which is connected to respective second coupling shaft 64c of handle assembly 100. Second rotatable proximal drive shaft 214 further includes a distal end portion 214b having a spur gear non-rotatably connected thereto.

First coupling shaft 251 of second force/rotation transmitting/converting assembly 250 includes a proximal end portion 251a having a spur gear non-rotatably connected thereto, and a distal end portion 251b having a spur gear non-rotatably connected thereto. The spur gear at the proximal end portion 251a of first coupling shaft 251 is in meshing engagement with the spur gear at the distal end portion 214b of the second rotatable proximal drive shaft 214.

Planetary gear set 252 of second force/rotation transmitting/converting assembly 250 includes a first cannulated sun gear 252a, a first set of planet gears 252b, a ring gear 252c, a second set of planet gears 252d, and a second cannulated sun gear 252e. First sun gear 252a is in meshing engagement with the spur gear at the distal end portion 251b of first coupling shaft 251. The first set of planet gears 252b are interposed between, and are in meshing engagement with, first sun gear 252a and ring gear 252c. The second set of planet gears 252d are interposed between, and are in meshing engagement with, second sun gear 252e and ring gear 252c. Ring gear 252c is non-rotatably supported in outer tube 206 of adapter assembly 200.

Planetary gear set 252 of second force/rotation transmitting/converting assembly 250 includes a washer 252f disposed within ring gear 252c, and between the first set of planet gears 252b and the second set of planet gears 252d. The first set of planet gears 252b are rotatably supported radially about washer 252f, and second sun gear 252e is non-rotatably connected to a center of washer 252f.

Staple lead screw 253 of second force/rotation transmitting/converting assembly 250 includes a proximal flange 253a and a distal threaded portion 253b extending from flange 253a. Staple lead screw 253 defines a lumen 253c therethrough. The second set of planet gears 252d are rotatably supported radially about proximal flange 253a of staple lead screw 253.

Staple driver 254 of second force/rotation transmitting/converting assembly 250 includes a central threaded lumen 254a extending therethrough and is configured and dimensioned to support distal threaded portion 253b of staple lead screw 253 therein. Staple driver 254 includes a pair of tabs 254b projecting radially from an outer surface thereof, and which are configured for connection to outer flexible band assembly 255 of adapter assembly 200, as will be described in greater detail below.

With reference now to FIGS. 34, 35 and 43-51, second force/rotation transmitting/converting assembly 250 of adapter assembly 200 includes an outer flexible band assembly 255 secured to staple driver 254. Outer flexible band assembly 255 includes first and second flexible bands 255a, 255b laterally spaced and connected at proximal ends thereof to a support ring 255c and at distal ends thereof to a proximal end of a support base 255d. Each of first and second flexible bands 255a, 255b is attached to support ring 255c and support base 255d.

Outer flexible band assembly 255 further includes first and second connection extensions 255e, 255f extending proximally from support ring 255c. First and second connection extensions 255e, 255f are configured to operably connect outer flexible band assembly 255 to staple driver 254 of second force/rotation transmitting/converting assembly 250. In particular, each of first and second connection extensions 255e, 255f defines an opening configured to receive a respective tab 254b of staple driver 254. Receipt of tabs 254b of staple driver 254 within the openings of respective first and second connection extensions 255e, 255f secures outer flexible band assembly 255 to staple driver 254 of second force/rotation transmitting/converting assembly 250.

Support base 255d extends distally from flexible bands 255a, 255b and is configured to selectively contact driver adapter 432 of staple driver assembly 430 of reload 400.

Flexible bands 255a, 255b are fabricated from stainless steel 301 half hard and are configured to transmit axial pushing forces along a curved path.

Second force/rotation transmitting/converting assembly 250 and outer flexible band assembly 255 are configured to receive first rotatable proximal drive shaft 212, first rotatable distal drive shaft 282, and trocar assembly 270 of first force/rotation transmitting/converting assembly 240 therethrough. Specifically, first rotatable proximal drive shaft 212 is non-rotatably connected to second rotatable proximal drive shaft 281 which in turn is rotatably disposed within and through first cannulated sun gear 252a of first planetary gear set 252, second cannulated sun gear 252e of planetary gear set 252, staple lead screw 253, and staple driver 254.

Second force/rotation transmitting/converting assembly 250 and outer flexible band assembly 255 are also configured to receive third force/rotation transmitting/converting assembly 260 therethrough. Specifically, as described below, inner flexible band assembly 265 is slidably disposed within and through outer flexible band assembly 255.

First rotatable distal drive shaft 282 of first force/rotation transmitting/converting assembly 240 is rotatably disposed within support base 255d of outer flexible band assembly 255, while trocar member 274 of trocar assembly 270 of first force/rotation transmitting/converting assembly 240 is slidably disposed within support base 255d of outer flexible band assembly 255.

Outer flexible band assembly 255 is also configured to receive inner flexible band assembly 265 therethrough.

In operation, as second rotatable proximal drive shaft 214 is rotated due to a rotation of second connector sleeve 220, as a result of the rotation of the second coupling shaft 64c of handle assembly 100, first coupling shaft 251 is caused to be rotated, which in turn causes first cannulated sun gear 252a to rotate. Rotation of first cannulated sun gear 252a, results in contemporaneous rotation of the first set of planet gears 252b, which in turn causes washer 252f to contemporaneously rotate second cannulated sun gear 252e. Rotation of second cannulated sun gear 252e, results in contemporaneous rotation of the second set of planet gears 252d, which in turn causes contemporaneous rotation of staple lead screw 253. As staple lead screw 253 is rotated, staple driver 254 is caused to be axially translated, which in turn causes outer flexible band assembly 255 to be axially translated. As outer flexible band assembly 255 is axially translated, support base 255d presses against driver adapter 432 of staple driver assembly 430 of reload 400 to distally advance driver 434 and fire staples "S" (FIG. 67) of reload 400 against anvil assembly 510 for formation of staples "S" in underlying tissue.

With reference to FIGS. 39-42 and 45-51, third force/rotation transmitting/converting assembly 260 of adapter assembly 200 includes third proximal drive shaft 216, as described above, a second coupling shaft 261, a planetary gear set 262, a knife lead screw 263, and a knife driver 264, each of which are supported within inner housing member 204, drive coupling assembly 210 and/or an outer tube 206 of adapter assembly 200. Third force/rotation transmitting/converting assembly 260 functions to fire knife of reload 400.

Third rotatable proximal drive shaft 216 includes a non-circular or shaped proximal end portion configured for connection with third connector or coupler 222 which is connected to respective third coupling shaft 64b of handle assembly 100. Third rotatable proximal drive shaft 216 further includes a distal end portion 216b having a spur gear non-rotatably connected thereto.

Second coupling shaft 261 of third force/rotation transmitting/converting assembly 260 includes a proximal end portion 261a having a spur gear non-rotatably connected thereto, and a distal end portion 261b having a spur gear non-rotatably connected thereto. The spur gear at the proximal end portion 261a of second coupling shaft 261 is in meshing engagement with the spur gear at the distal end portion 216b of the third rotatable proximal drive shaft 216.

Planetary gear set 262 of third force/rotation transmitting/converting assembly 260 includes a first cannulated sun gear 262a, a first set of planet gears 262b, a ring gear 262c, a second set of planet gears 262d, and a second cannulated sun gear 262e. First sun gear 262a is non-rotatably supported on a distal end portion of a hollow shaft 269. Hollow shaft 269 includes a spur gear 269a non-rotatably supported on a proximal end thereof. Spur gear 269a of hollow shaft 269 is in meshing engagement with the spur gear at the distal end portion 261b of second coupling shaft 261. The first set of planet gears 262b are interposed between, and are in meshing engagement with, first sun gear 262a and ring gear 262c. The second set of planet gears 262d are interposed between, and are in meshing engagement with, second sun gear 262e and ring gear 262c. Ring gear 262c is non-rotatably supported in outer tube 206 of adapter assembly 200.

Planetary gear set 262 of third force/rotation transmitting/converting assembly 260 includes a washer 262f disposed within ring gear 262c, and between the first set of planet gears 262b and the second set of planet gears 262d. The first set of planet gears 262b are rotatably supported radially about washer 262f, and second sun gear 262e is non-rotatably connected to a center of washer 262f.

Knife lead screw 263 of second force/rotation transmitting/converting assembly 260 includes a proximal flange 263a and a distal threaded portion 263b extending from flange 263a. Knife lead screw 263 defines a lumen 263c therethrough. The second set of planet gears 262d are rotatably supported radially about proximal flange 263a of knife lead screw 263.

Knife driver 264 of second force/rotation transmitting/converting assembly 260 includes a central threaded lumen 264a extending therethrough and is configured and dimensioned to support distal threaded portion 263b of knife lead screw 263 therein. Knife driver 264 includes a pair of tabs 264b projecting radially from an outer surface thereof, and which are configured for connection to inner flexible band assembly 265 of adapter assembly 200, as will be described in greater detail below.

With reference now to FIGS. 39-42, third force/rotation transmitting/converting assembly 260 of adapter assembly 200 includes an inner flexible band assembly 265 secured to knife driver 264. Inner flexible band assembly 265 includes first and second flexible bands 265a, 265b laterally spaced and connected at proximal ends thereof to a support ring 265c and at distal ends thereof to a proximal end of a support base 265d. Each of first and second flexible bands 265a, 265b are attached to support ring 265c and support base 265d. Inner flexible band assembly 265 is configured to receive first rotatable proximal drive shaft 212, first rotatable distal drive shaft 282, and trocar assembly 270 of first force/rotation transmitting/converting assembly 240 therethrough.

Inner flexible band assembly 265 further includes first and second connection extensions 265e, 265f extending proximally from support ring 265c. First and second connection extensions 265e, 265f are configured to operably connect inner flexible band assembly 265 to knife driver 264 of third force/rotation transmitting/converting assembly 260. In particular, each of first and second connection extensions 265e, 265f defines an opening configured to receive a respective tab 264b of knife driver 264. Receipt of tabs 264b of knife driver 264 within the openings of respective first and second connection extensions 265e, 265f secures inner flexible band assembly 265 to knife driver 264 of third force/rotation transmitting/converting assembly 260.

Support base 265d extends distally from flexible bands 265a, 265b and is configured to connect with knife carrier 442 of knife assembly 440 of reload 400.

Flexible bands 265a, 265b are fabricated from stainless steel 301 half hard and are configured to transmit axial pushing forces along a curved path.

Third force/rotation transmitting/converting assembly 260 and inner flexible band assembly 265 are configured to receive first rotatable proximal drive shaft 212, first rotatable distal drive shaft 282, and trocar assembly 270 of first force/rotation transmitting/converting assembly 240 therethrough. Specifically, first rotatable proximal drive shaft 212 is rotatably disposed within and through hollow shaft 269, first cannulated sun gear 262a of first planetary gear set 262, second cannulated sun gear 262e of planetary gear set 262, knife lead screw 263, and knife driver 264.

First rotatable distal drive shaft 282 of first force/rotation transmitting/converting assembly 240 is also rotatably disposed within support base 265d of inner flexible band assembly 265, while trocar member 274 of trocar assembly 270 of first force/rotation transmitting/converting assembly 240 is slidably disposed within support base 265d of inner flexible band assembly 265.

In operation, as third rotatable proximal drive shaft 216 is rotated due to a rotation of third connector sleeve 222, as a result of the rotation of the third coupling shaft 64b of handle assembly 100, second coupling shaft 261 is caused to be rotated, which in turn causes hollow shaft 269 to rotate. Rotation of hollow shaft 269 results in contemporaneous rotation of the first set of planet gears 262b, which in turn causes washer 262f to rotate second cannulated sun gear 262e. Rotation of second cannulated sun gear 262e causes contemporaneous rotation of the second set of planet gears 262d, which in turn causes knife lead screw 263 to rotate. As knife lead screw 263 is rotated, knife driver 264 is caused to be axially translated, which in turn causes inner flexible band assembly 265 to be axially translated. As inner flexible band assembly 265 is axially translated, support base 265d presses against knife carrier 442 of reload 400 to distally advance knife carrier 442 and fire annular knife 444 of reload 400 against anvil assembly 510 for cutting of tissue clamped in reload 400.

Turning now to FIGS. 21-24, adapter assembly 200 includes an outer tube 206 extending from knob housing 202. As mentioned above, outer tube 206 is configured to support first, second and third force/rotation transmitting/converting assembly 240, 250, 260, respectively. Adapter assembly 200 further includes a frame assembly 230 supported in outer tube 206. Frame assembly 230 is configured to support and guide flexible bands 255a, 255b of outer flexible band assembly 255, and flexible bands 265a, 265b of inner flexible band assembly 265, as flexible bands 255a, 255b, 265a, 265b are axially translated through outer tube 206.

Frame assembly 230 includes first and second proximal spacer members 232a, 232b, and first and second distal spacer members 234a, 234b. When secured together, first and second proximal spacer members 232a, 232b define a pair of inner longitudinal slots 234c for slidably receiving first and second flexible bands 265a, 265b of inner flexible band assembly 265 and a pair of outer longitudinal slots 234d for slidably receiving first and second flexible bands 255a, 255b of outer flexible band assembly 255. First and second proximal spacer members 232a, 232b further define a longitudinal passage therethrough for receipt of first force/rotation transmitting/converting assembly 240 and trocar assembly 270.

First and second distal spacer members 234a, 234b define a pair of inner slots 234c for slidably receiving first and second flexible bands 265a, 265b of inner flexible band assembly 265 and a pair of outer slots 234d for slidably receiving first and second flexible bands 255a, 255b of outer flexible band assembly 255. First and second distal spacer members 234a, 234b further define a longitudinal passage therethrough for receipt of first force/rotation transmitting/converting assembly 240, and trocar assembly 270.

First and second proximal spacer members 232a, 232b and first and second distal spacer members 234a, 234b are formed of plastic to reduce friction with flexible bands 255a, 255b of outer flexible band assembly 255, and flexible bands 265a, 265b of inner flexible band assembly 265.

With reference now to FIGS. 44-50, frame assembly 230 further includes a seal member 235. Seal member 235 engages outer tube 206, inner and outer flexible bands 255a, 255b and 265a, 265b of respective inner and outer flexible band assemblies 255, 265 and trocar assembly 270, and wiring extending therethrough, in a sealing manner. In this manner, seal member 235 operates to provide a fluid tight seal through between the distal end and the proximal end of outer tube 206.

Adapter assembly 200 further includes a connector sleeve 290 fixedly supported at a distal end of outer tube 206. Connector sleeve 290 is configured to selectively secure securing reload 400 to adapter assembly 200, as will be described in greater detail below. Connector sleeve 290 is also configured to be disposed about distal ends of outer and inner flexible assemblies 255, 265 and trocar assembly 270. In particular, a proximal end of connector sleeve 290 is received within and securely attached to the distal end of outer tube 206 and is configured to engage a stain gauge assembly 320 of adapter assembly 200, and a distal end of connector sleeve 290 is configured to selectively engage a proximal end of reload 400.

With reference now to FIGS. 52-55, 60 and 69, adapter assembly 200 includes an electrical assembly 310 disposed therewithin, and configured for electrical connection with and between handle assembly 100 and reload 400. Electrical assembly 310 serves to allow for calibration and communication information (e.g., identifying information, life-cycle information, system information, force information) to the main controller circuit board 142b of power-pack core assembly 106 via electrical receptacle 149 of power-pack core assembly 106 of handle assembly 100.

Electrical assembly 310 includes a proximal pin connector assembly 312, a proximal harness assembly 314 in the form of a ribbon cable, a distal harness assembly 316 in the form of a ribbon cable, a strain gauge assembly 320, and a distal electrical connector 322.

Figure 53:
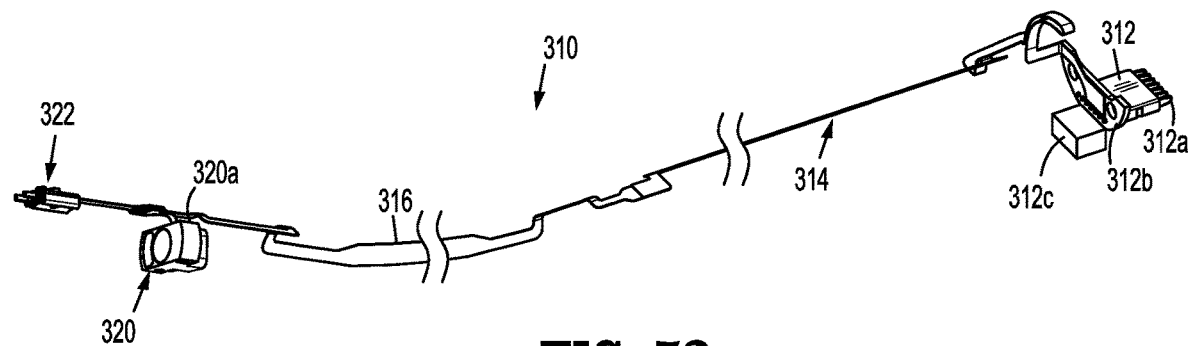
FIG. 53 is a perspective view of the electrical assembly of the adapter assembly of the present disclosure.
Figure 54:
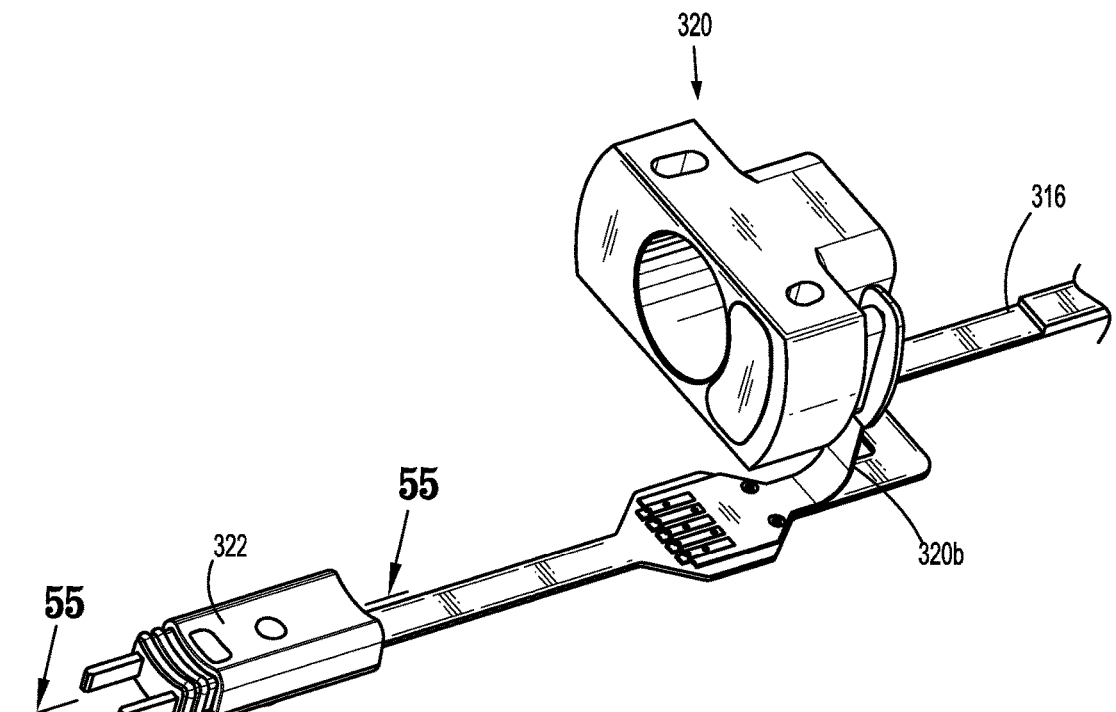
FIG. 54 is a perspective view of a strain gauge assembly of the electrical assembly of FIGS. 52-53.

Proximal pin connector assembly 312 of electrical assembly 310 is supported within inner housing member 204 and drive coupling assembly 210 of knob housing 202. Proximal pin connector assembly 312 includes a plurality of electrical contact blades 312a supported on a circuit board 312b and which enable electrical connection to pass-through connector 66 of plate assembly 60 of outer shell housing 10 of handle assembly 100. Proximal harness assembly 314 is electrically connected to circuit board 312b of proximal pin connector assembly 312 (FIGS. 53 and 54).

Strain gauge assembly 320 is electrically connected to proximal pin connector assembly 312 via proximal and distal harness assemblies 314, 316. Strain gauge assembly 320 includes a strain sensor 320a supported in outer tube 206 of adapter assembly 200. Strain sensor 320a is electrically connected to distal harness assembly 316 via a sensor flex cable 320b. Strain sensor 320a defines a lumen therethrough, through which trocar assembly 270 extends.

As illustrated in FIGS. 29-33, trocar assembly 270 of first force/rotation transmitting/converting assembly 240 extends through strain sensor 320a of strain gauge assembly 320. Strain gauge assembly 320 provides a closed-loop feedback to a firing/clamping load exhibited by first, second and third force/rotation transmitting/converting assembly 240, 250, 260, respectively.

Strain sensor 320a of strain gauge assembly 320 is supported in outer tube 206 and interposed between connector sleeve 290 and support block 292. Support block 292 includes a raised ledge 292b (see FIG. 29) which extends distally therefrom and which is in contact with strain sensor 320a.

Figure 55:
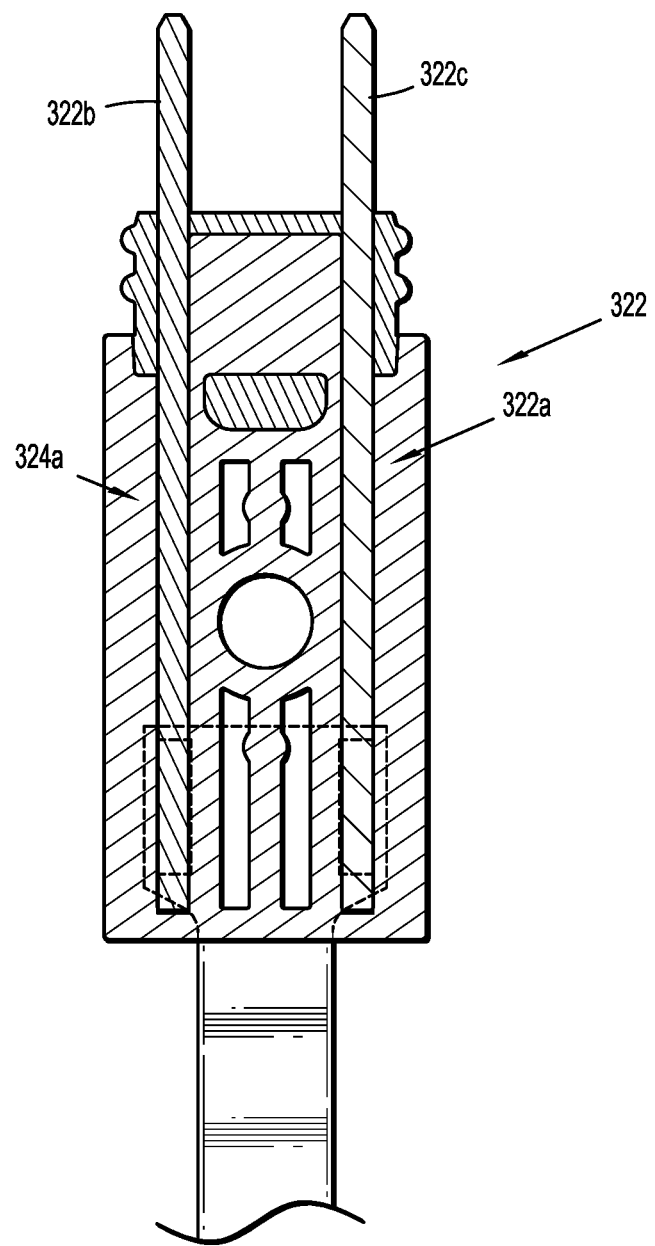
FIG. 55 is a cross-sectional view, as taken through 55-55 of FIG. 54.
Figure 56:
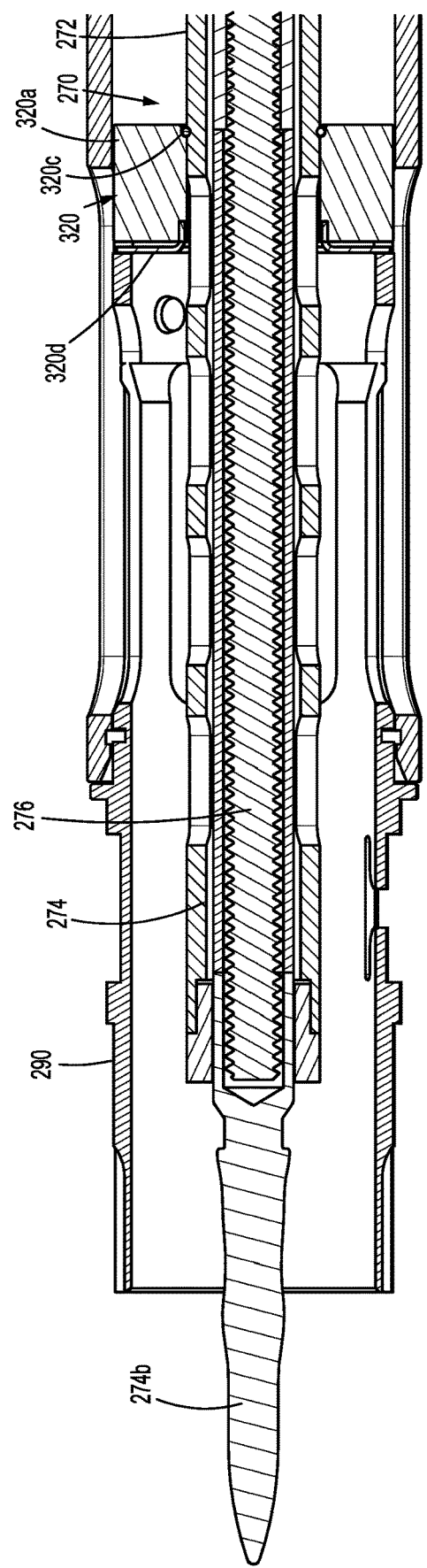
FIG. 56 is a longitudinal, cross-sectional view of the more distal end portion of the adapter assembly illustrated in FIGS. 49 and 50.

With reference now to FIGS. 53-55, electrical assembly 310 includes, as mentioned above, a distal electrical connector 322 which is supported in connector sleeve 290. Distal electrical connector 322 is configured to selectively mechanically and electrically connect to chip assembly 460 of reload 400 when reload 400 is connected to adapter assembly 200.

Distal electrical connector 322 includes a plug member 322a, first and second wires 323a, 323b, and first and second contact members 324a, 324b electrically connected to respective first and second wires 323a, 323b. Plug member 322a includes a pair of arms 322b, 322c supporting first and second contact members 324a, 324b, respectively. The pair of arms 322b, 322c are sized and dimensioned to be received within a cavity 461a of chip assembly 460 and about a circuit board assembly 464 of reload 400 when reload 400 is connected to adapter assembly 200.

First and second contact members 324a, 324b of distal electrical connector 322 are configured to engage respective contact members 464b of circuit board assembly 464 of chip assembly 460 of reload 400 when reload 400 is connected to adapter assembly 200.

With reference now to FIGS. 57-65, adapter assembly 200 includes a rotation assembly 330 configured to enable rotation of adapter assembly 200 relative to handle assembly 100. Specifically, outer knob housing 202 and an outer tube 206 of adapter assembly 200 are rotatable relative to drive coupling assembly 210 of adapter assembly 200.

Rotation assembly 330 includes a lock button 332 operably supported on outer knob housing 202. As will be described in further detail below, when rotation assembly 330 is in an unlocked configuration, outer knob housing 202 and an outer tube 206 are rotatable along a longitudinal axis of adapter assembly 200 relative to drive coupling assembly 210. When rotation assembly 330 is in a locked configuration, outer knob housing 202 and an outer tube 206 are rotationally secured relative to drive coupling assembly 210. In particular, being that outer tube 206 has a curved profile, rotation of outer knob housing 202 and an outer tube 206 about the longitudinal axis of adapter assembly 200 causes handle assembly 100 to be positioned in various orientations relative to adapter assembly 200 in order to provide the clinician with increased flexibility in manipulating the surgical instrument in the target surgical site.

Lock button 332 of rotation assembly 330 is configured to operatively engage inner housing member 204 of adapter assembly 200. Inner housing member 204 is a substantially cylindrical member defining a pair of longitudinal openings for receiving at least portions of first and second force/rotation transmitting/converting assemblies 240, 250 therethrough. Inner housing member 204 includes proximal and distal annular flanges 204a, 204b and further defines proximal and distal outer annular grooves. The proximal annular groove of inner housing member 204 accommodates an inner annular flange of outer knob housing 202 to rotatably secure outer knob housing 202 to inner housing member 204.

With reference still to FIGS. 57-65, distal annular flange 204b and the distal annular groove of inner housing member 204 operate in combination with rotation assembly 330 of adapter assembly 200 to secure outer knob housing 202 in fixed rotational orientations relative to inner housing member 204. In particular, distal annular flange 204b of inner housing member 204 defines first, second, and third radial cutouts 204c, 204d, 204e configured to selectively receive a lock shoe 334 of lock button 332 of rotation assembly 330. The first and third cutouts 204c, 204e are opposed to one another, and second cutout 204d is oriented perpendicular to the first and third cutouts 204c, 204e.

Figure 60:
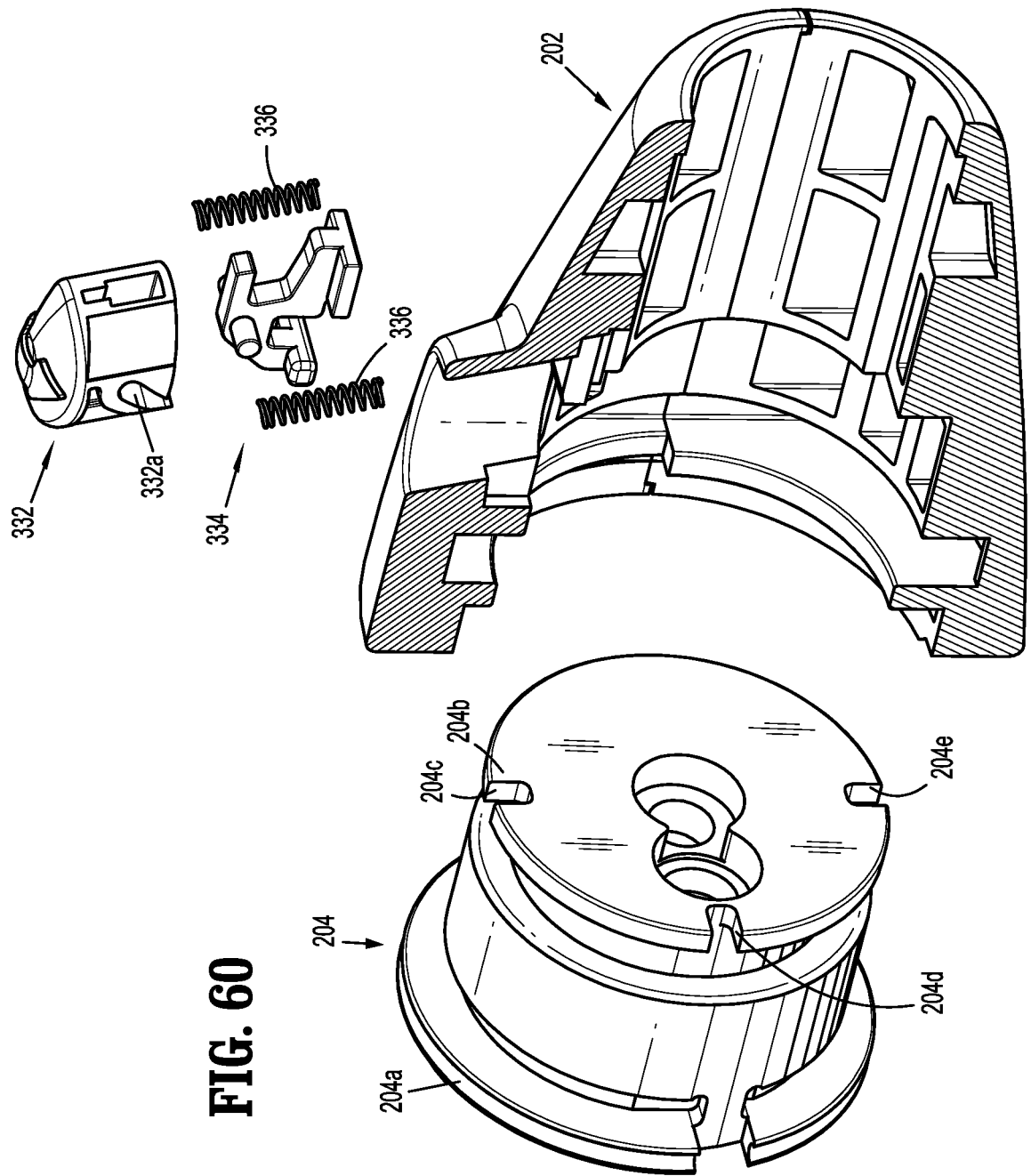
FIG. 60 is a perspective, partial cross-sectional view, with parts separated, of the rotation assembly of FIG. 58.
Figure 61:
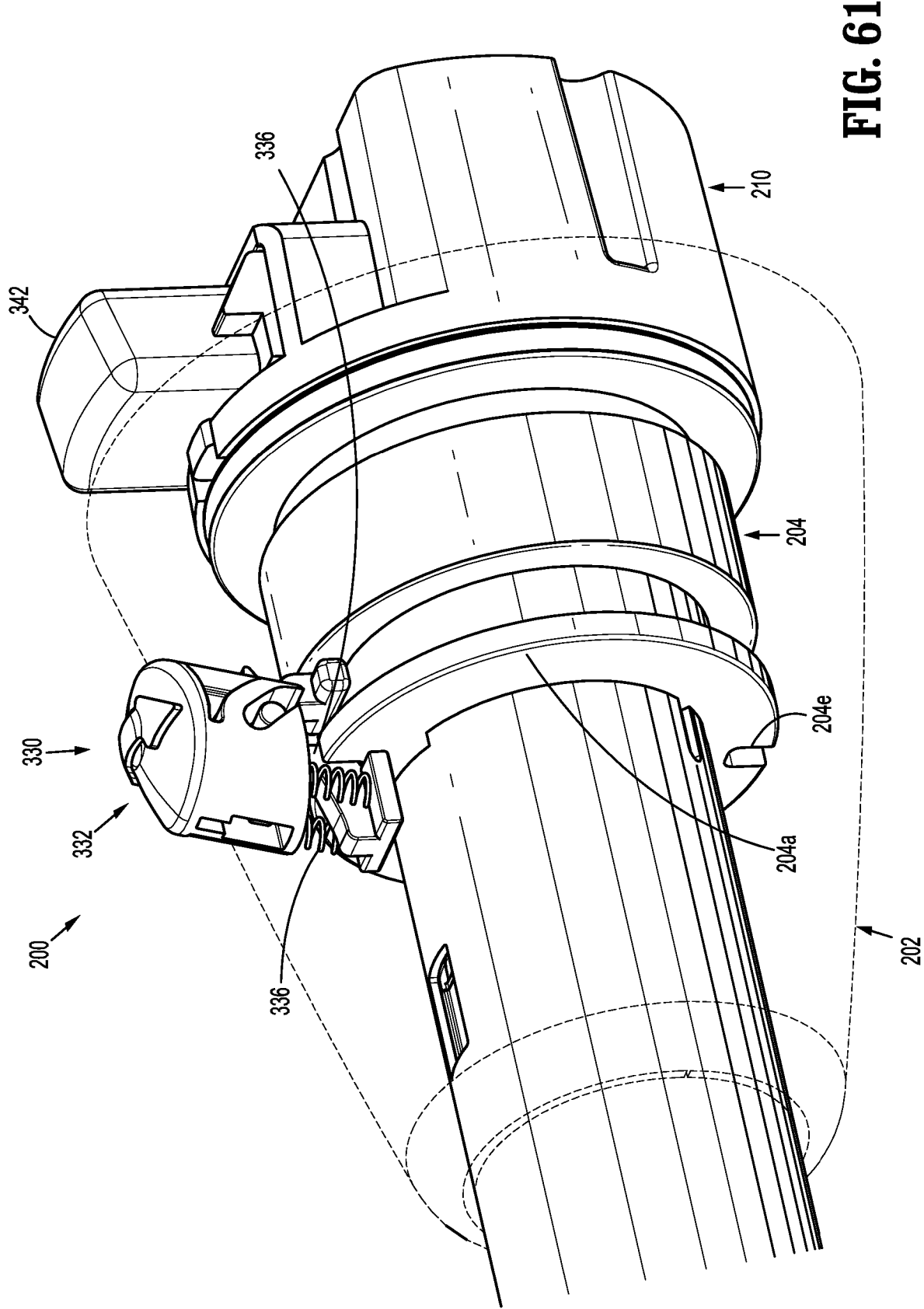
FIG. 61 is a perspective view of the rotation assembly, illustrating an operation thereof.

With reference to FIGS. 60-61, outer knob housing 202 has a frustoconical profile including a plurality of ridges configured for operable engagement by a clinician. Outer knob housing 202 defines a radial opening for operably supporting lock button 332. The opening in outer knob housing 202 is positioned in alignment or registration with the distal annular groove of inner housing member 204 such that lock button 332 of rotation assembly 330 is receivable with the distal annular groove and selectively receivable within each of the first, second, and third cutouts 204c, 204d, 204e in distal annular flange 204b of inner housing member 204.

As mentioned above, rotation assembly 330 of adapter assembly 200 includes a lock button 332 operably supported in an opening of outer knob housing 202 and configured for actuating rotation assembly 330. Rotation assembly 330 further includes a lock shoe 334 disposed between outer knob housing 202 and inner housing member 204 and axially slidable relative to lock button 332 and inner housing member 204. A biasing member 336 is interposed between lock button 332 and lock shoe 334 to urge lock button 332 to a locked position, wherein lock shoe 334 is disposed within one of first, second, and third cutouts 204c, 204d, 204e in distal annular flange 204b of inner housing member 204.

Lock button 332 is configured for operable engagement by a clinician. Lock button member 332 defines an angled cam slot 332a formed therein for receiving a cam pin or boss 334a of lock shoe 334. The biasing member 336 biases lock button 332 and lock shoe 334 away from one another, and urges lock shoe 334 into contact with distal annular flange 204b of inner housing member 204 and into one of first, second, and third cutouts 204c, 204d, 204e in distal annular flange 204b when lock shoe 334 is in registration with one of first, second, and third cutouts 204c, 204d, 204e.

As mentioned above, lock shoe 334 is configured to be selectively received within one of the first, second, and third radial cutouts 204c, 204d, 204e in distal annular flange 204b of inner housing member 204. Specifically, lock shoe 334 includes or defines a shoulder 334a projecting from a surface thereof for receipt in one of the first, second, and third radial cutouts 204c, 204d, 204e in distal annular flange 204b when shoulder 334a of lock shoe 334 is in registration with one of the first, second, and third radial cutouts 204c, 204d, 204e in distal annular flange 204b and lock button 332 is un-depressed. When shoulder 334a of lock shoe 334 is free of any of the first, second, and third radial cutouts 204c, 204d, 204e in distal annular flange 204b (e.g., rotation assembly 330 is in an unlocked condition), outer knob housing 202 is free to rotate relative to inner housing member 204, and thus adapter assembly 200 is free to rotate relative to handle assembly 100.

The operation of rotation assembly 330 will now be described with continued reference to FIGS. 57-65. Referring initially to FIGS. 58, 59, 61 and 64, rotation assembly 330 is shown in a locked condition. In particular, in the locked condition, shoulder 334a of lock shoe 334 is received within first cutout 204c in distal annular flange 204a of inner housing member 204. Also, in the locked condition, lock button 332 of rotation mechanism 330 is biased radially outward by biasing member 336.

Figure 64:
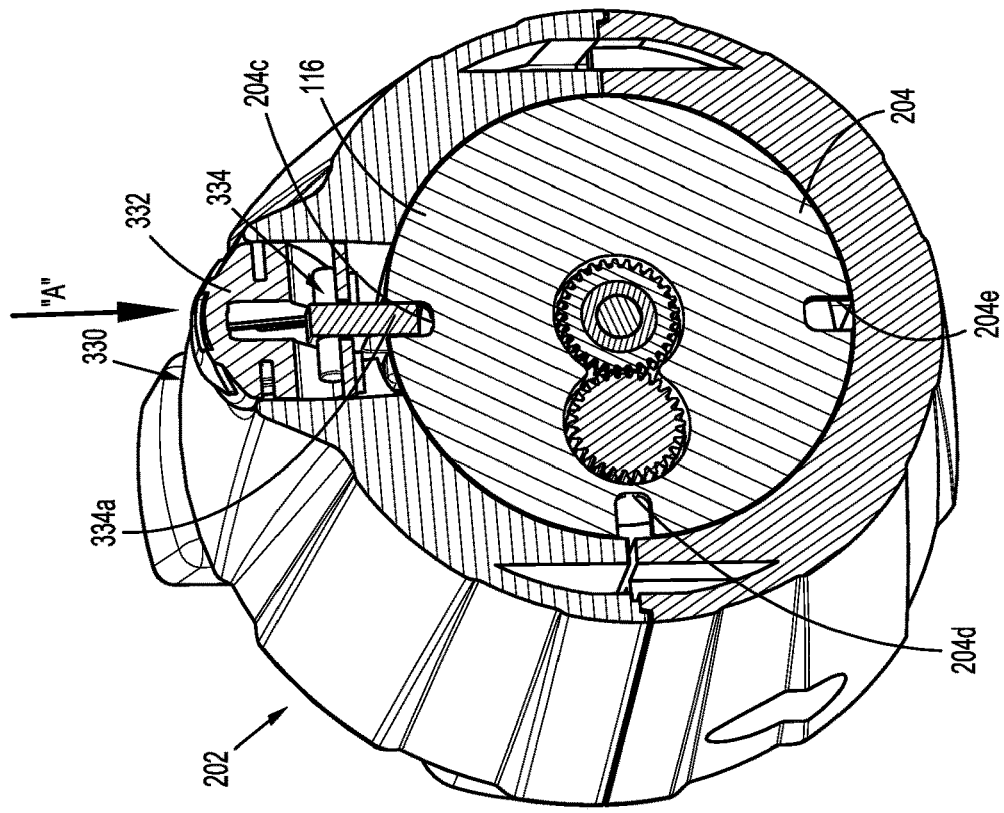
FIG. 64 is a cross-sectional view, as taken through 64-64 of FIG. 63.
Figure 66:
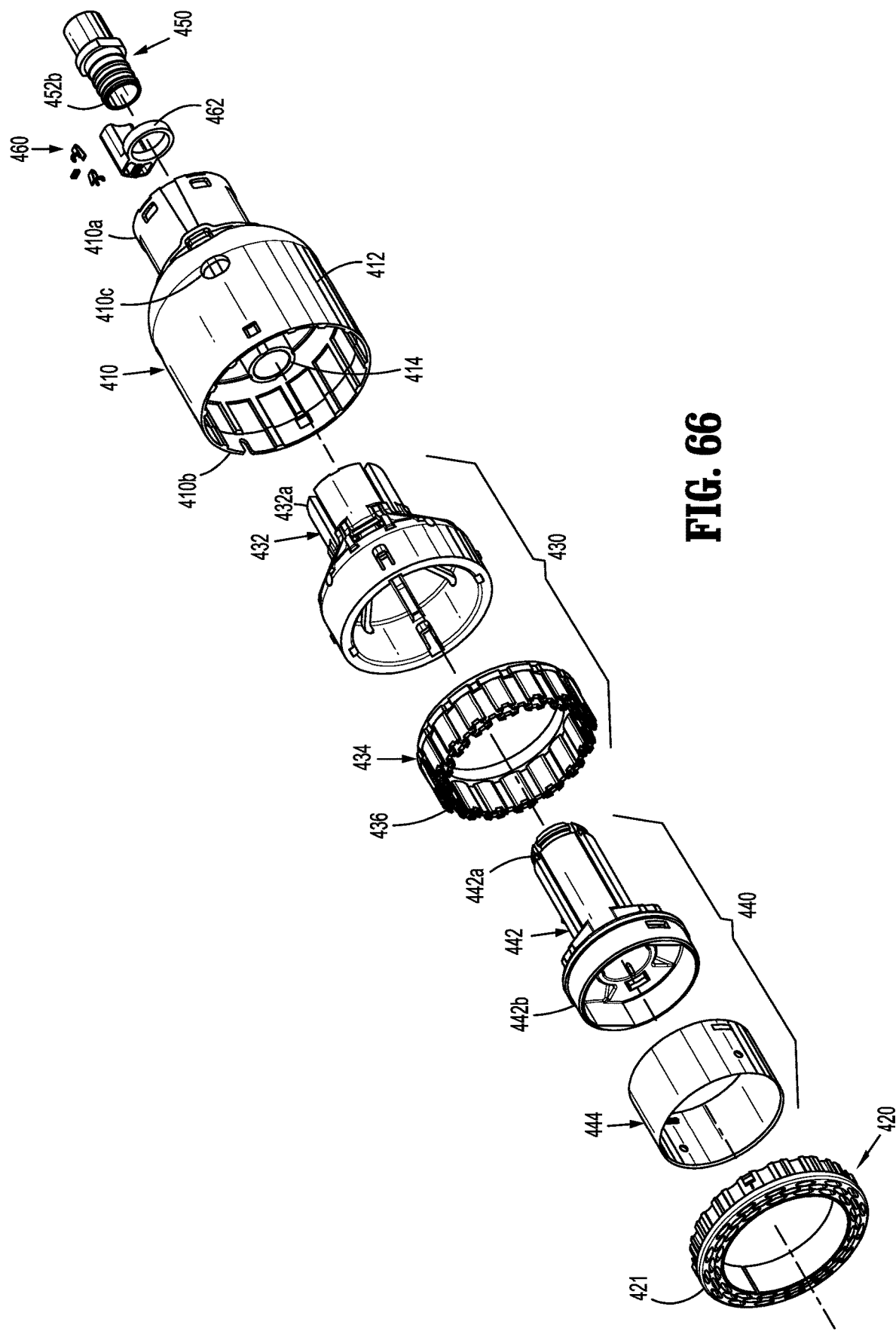
FIG. 66 is a perspective view, with parts separated, of a reload according to the present disclosure.
Figure 69:
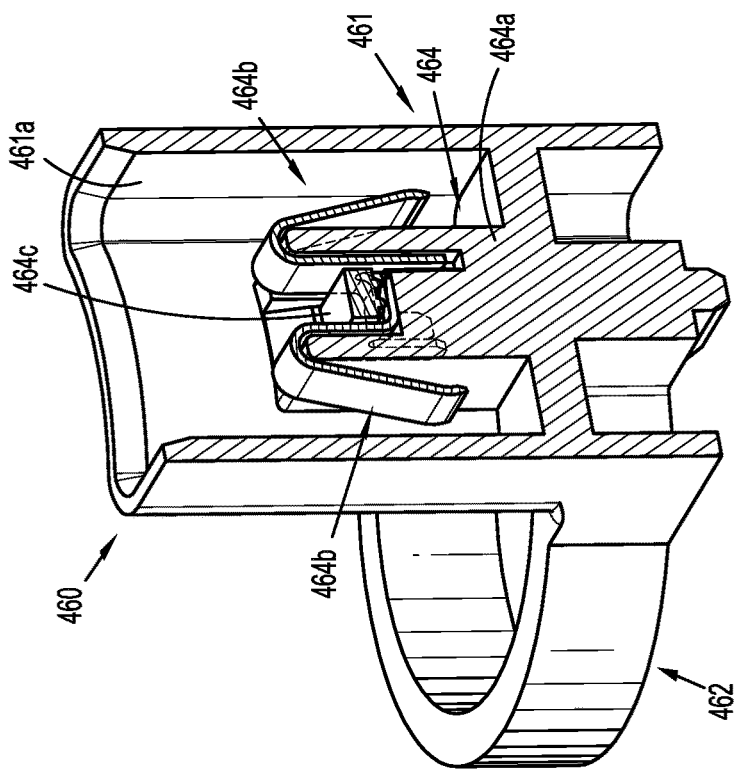
FIG. 69 is a cross-sectional view, as taken through 69-69 of FIG. 68.
Figure 68:
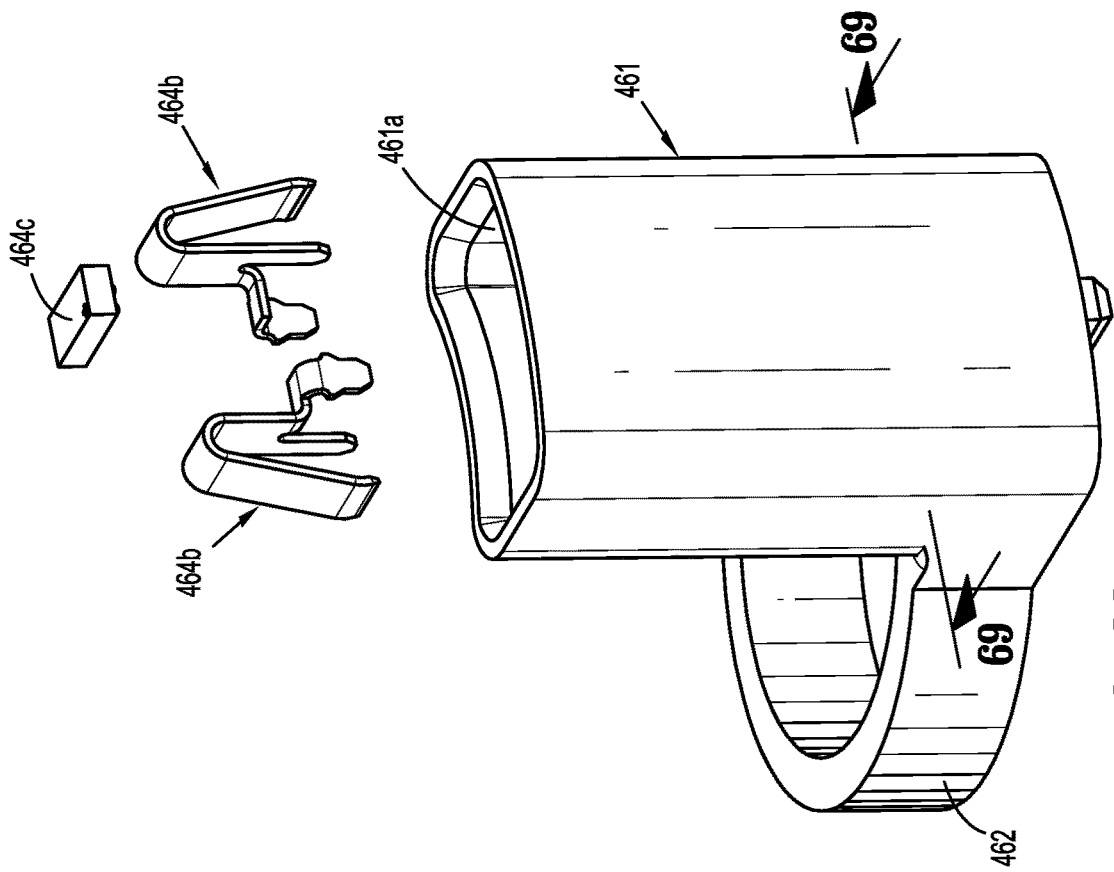
FIG. 68 is a perspective view of an electrical connector of the reload of FIGS. 66-67.
Figure 70:
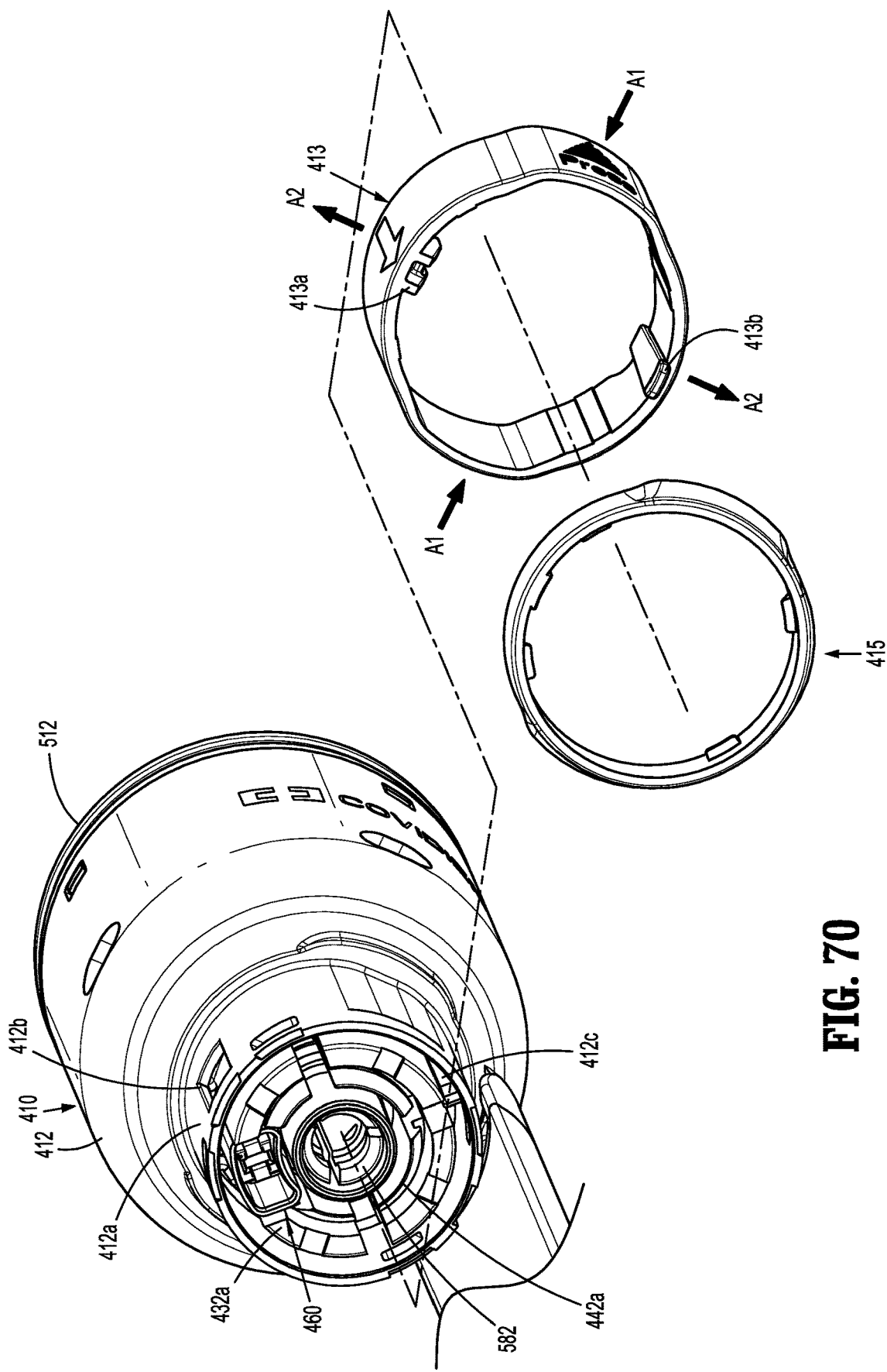
FIG. 70 is a rear, perspective view of the reload of FIGS. 66-69, with a release ring and a retaining ring illustrated separated therefrom.
Figure 71:
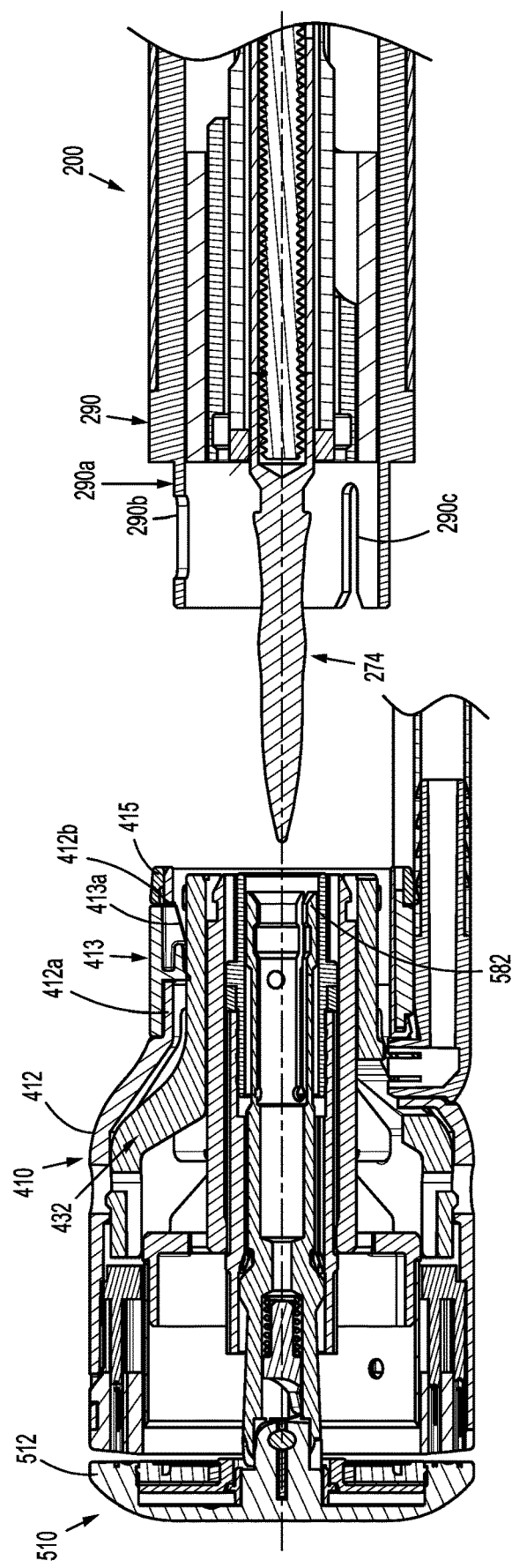
FIG. 71 is a longitudinal, cross-sectional view, illustrating the reload aligned with and separated from the more distal end portion of the adapter assembly.
Figure 72:
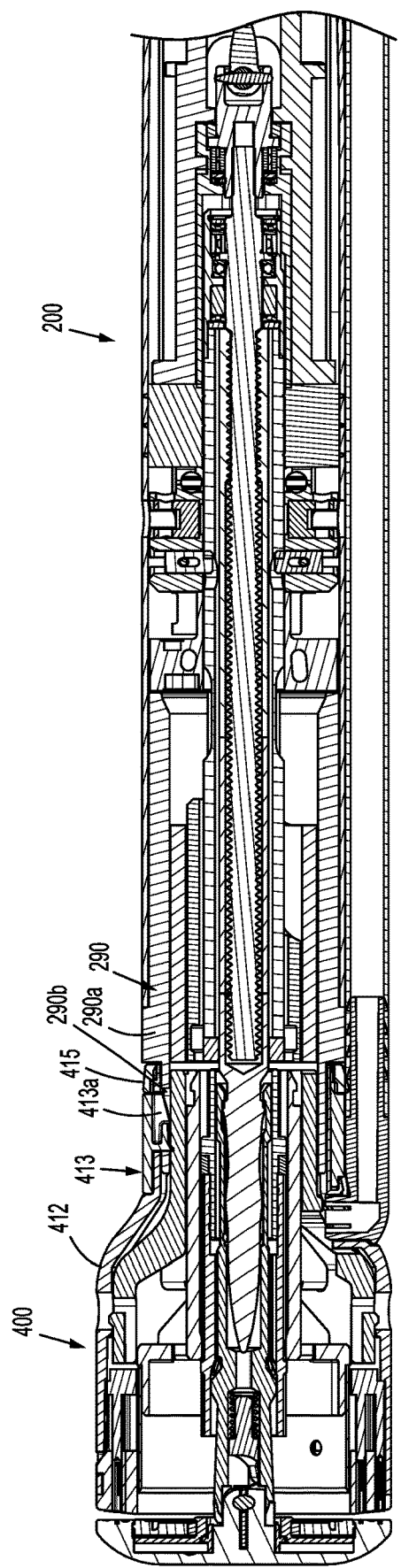
FIG. 72 is a longitudinal, cross-sectional view, illustrating the reload aligned and connected with the more distal end portion of the adapter assembly.

When lock button 332 of rotation assembly 330 is depressed, as indicated by arrow "A" in FIG. 64, lock button 332 moves radially inward against the bias of biasing member 336. As lock button 332 moves radially inward, lock shoe 334 slides axially in a distal direction, against the bias of biasing member 336. The axial sliding of lock shoe 334 moves shoulder 334a of lock shoe 334 from within the first radial cutout 204c of the distal annular flange 204b of inner housing member 204, thus placing rotation assembly 330 in an unlocked condition and freeing outer knob housing 202 to rotate, as indicated by arrow "B" in FIG. 62, relative to inner housing member 204.

Figure 65:
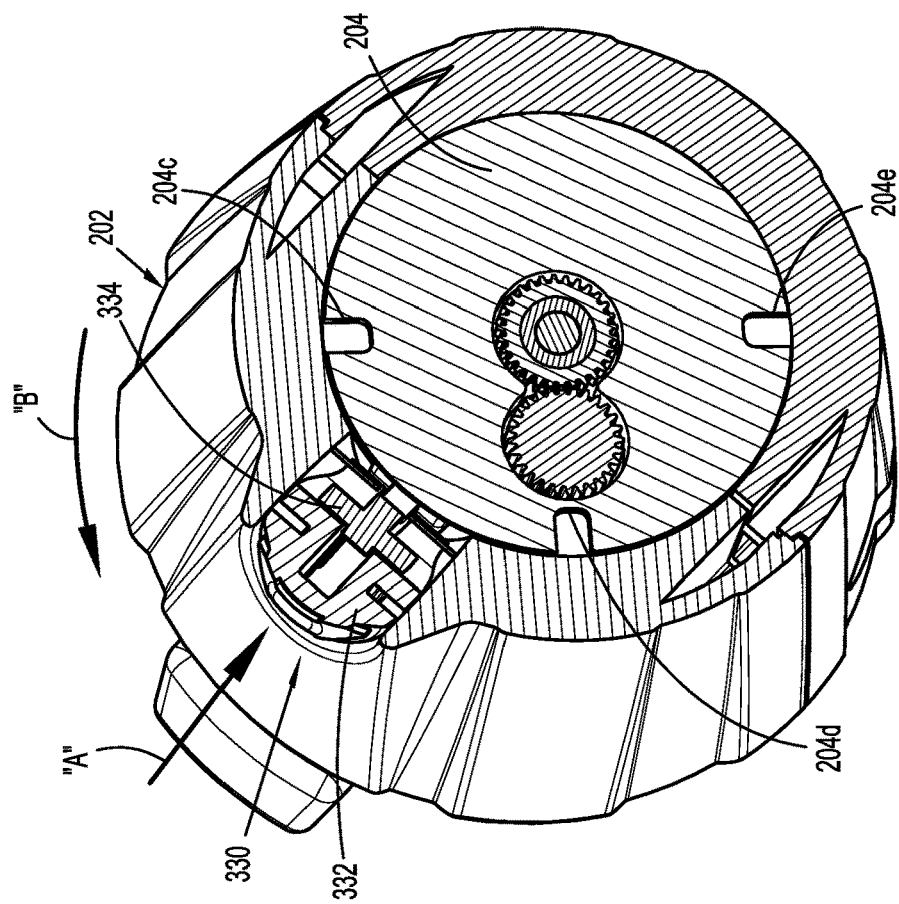
FIG. 65 is a cross-sectional view, as taken through 64-64 of FIG. 63, illustrating the rotation of the rotation assembly and the shaft assembly relative to the drive coupling assembly.

Turning now to FIG. 65, once rotation assembly 330 is in the unlocked condition, outer knob housing 202 may be rotated relative to inner housing member 204. The release of lock button 332 allows biasing member 336 to bias lock button 332 to its initial position. Similarly, biasing member 336 biases lock shoe 334 to its initial position. When lock shoe 334 is re-aligned with one of the first, second, and third radial cutouts 204c, 204d, 204e of distal annular flange 204b of inner housing member 204, as outer knob housing 202 is rotated relative to inner housing member 204, shoulder 334a of lock shoe 334 is free to be received within the respective first, second, and third cutout 204c, 204d, 204e and rotationally locks outer knob housing 202 relative to inner housing member 204 and drive coupling assembly 210 of adapter assembly 200.

Rotation assembly 330 may be used throughout the surgical procedure to rotate handle assembly 100 and adapter assembly 200 relative to one another.

During rotation of outer knob housing 202 relative to inner housing member 204 and drive coupling assembly 210 of adapter assembly 200, since proximal drive shafts 212, 214, 216 are supported in drive coupling assembly 210, and since first coupling shaft 251 of second force/rotation transmitting/converting assembly 250, second coupling shaft 261 of third force/rotation transmitting/converting assembly 260, and second rotatable proximal drive shaft 281 of first force/rotation transmitting/converting assembly 240 are supported in inner housing member 204, the respective angular orientations of proximal drive shaft 212 relative to second rotatable proximal drive shaft 281, proximal drive shaft 216 relative to second coupling shaft 261, and proximal drive shaft 214 relative to first coupling shaft 251, are changed relative to one another.

Figure 57:
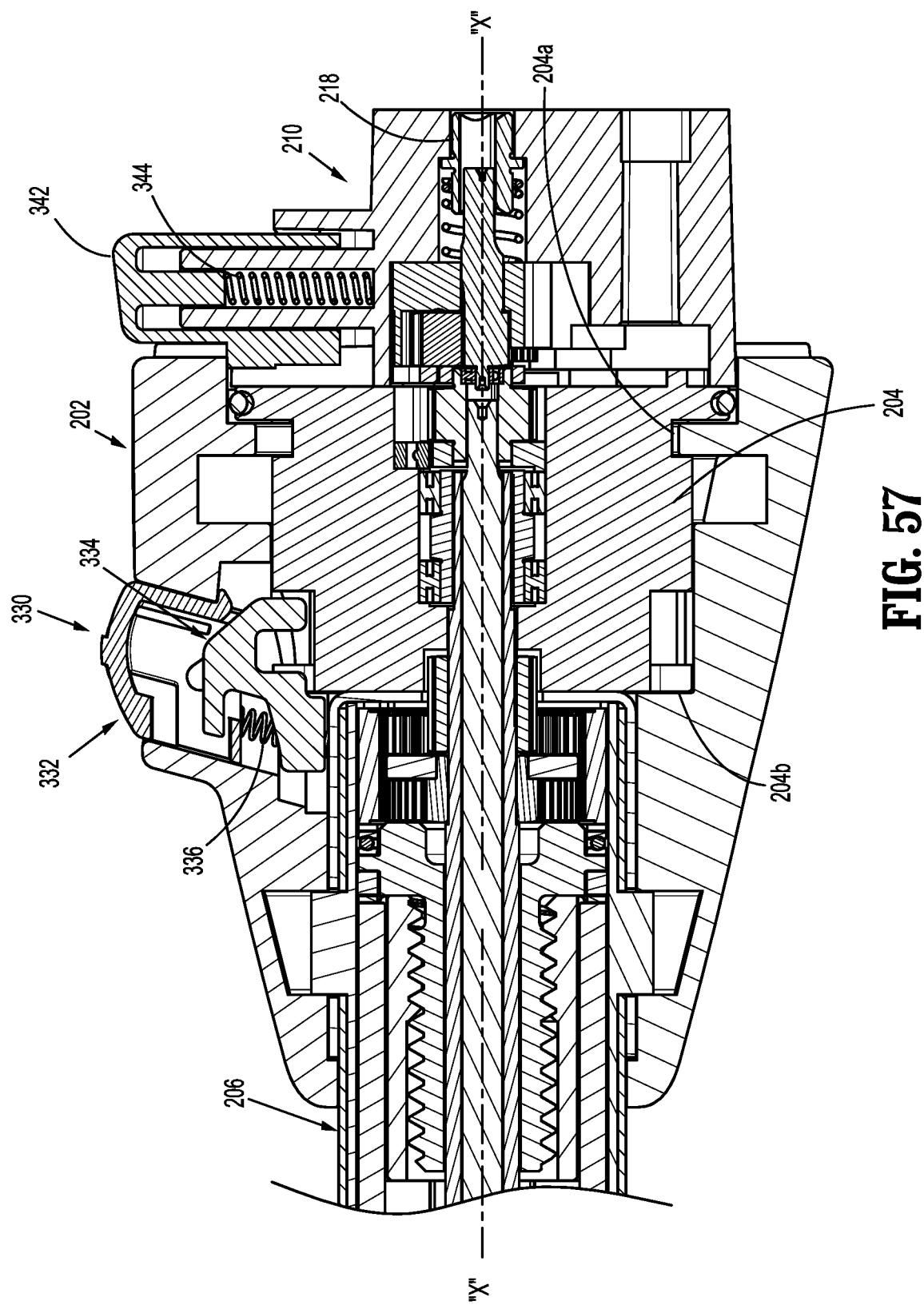
FIG. 57 is a longitudinal, cross-sectional view of a knob assembly of the adapter assembly of the present disclosure.
Figure 58:
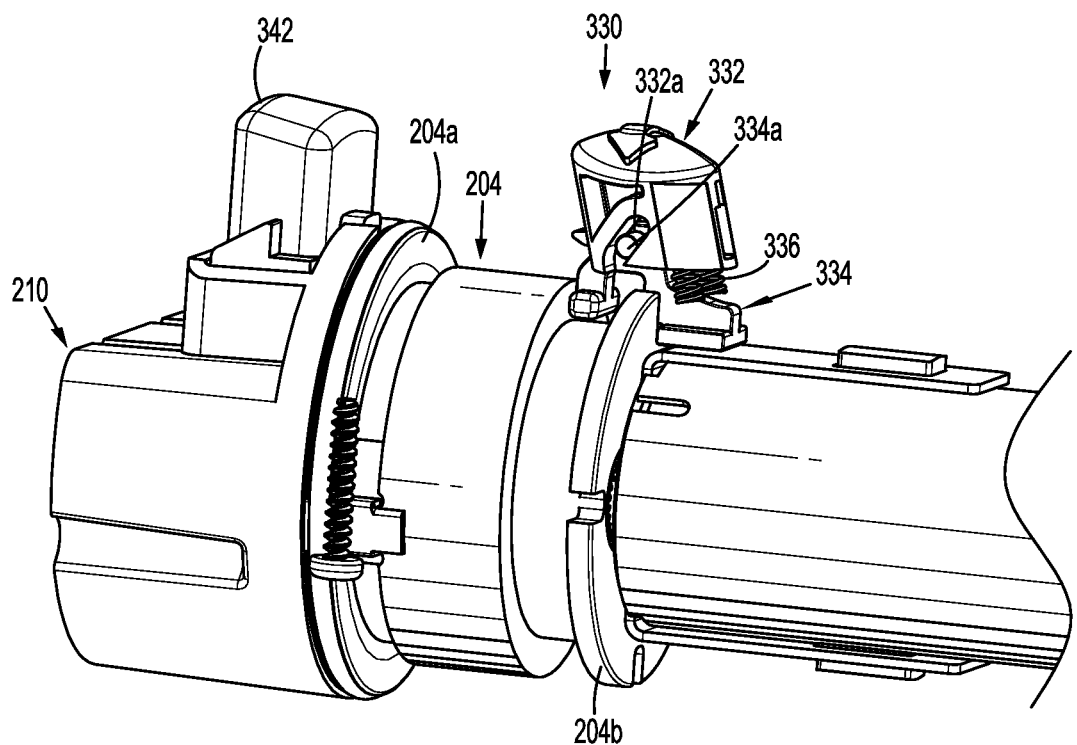
FIG. 58 is a perspective view of a rotation assembly of the knob assembly.
Figure 59:
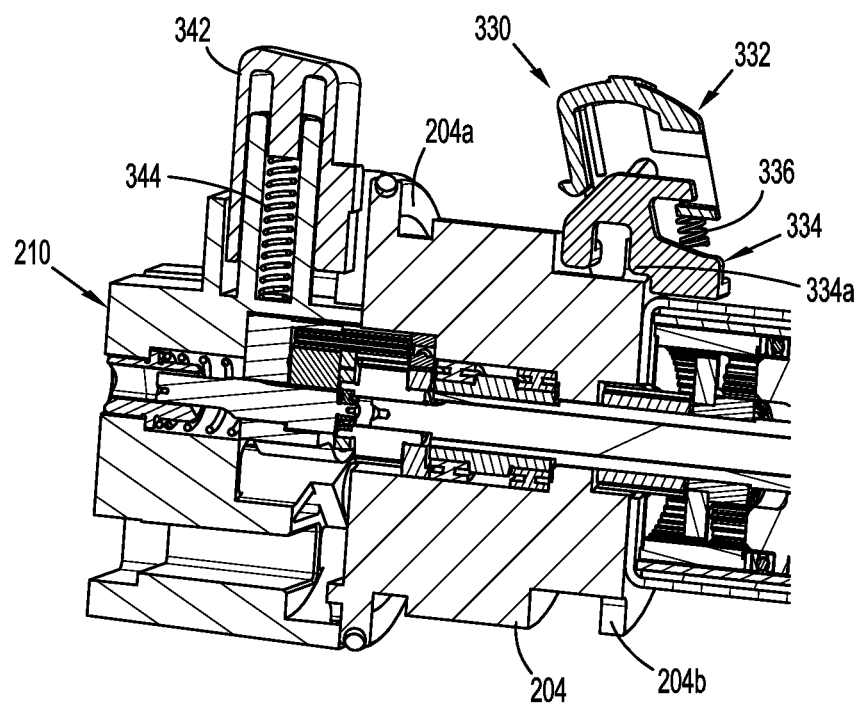
FIG. 59 is a longitudinal, cross-sectional view of the rotation assembly of FIG. 58.

Adapter assembly 200 further includes, as seen in FIGS. 57-59, an attachment/detachment button 342 supported thereon. Specifically, button 342 is supported on drive coupling assembly 210 of adapter assembly 200 and is biased by a biasing member 344 to an un-actuated condition. Button 342 includes a lip or ledge 342a formed therewith that is configured to snap behind a corresponding lip or ledge 20a (FIG. 18) defined along recess 20 of connecting portion 108 of handle housing 102 of handle assembly 100. In use, when adapter assembly 200 is connected to handle assembly 100, lip 342a of button 342 is disposed behind lip 108b of connecting portion 108 of handle housing 102 of handle assembly 100 to secure and retain adapter assembly 200 and handle assembly 100 with one another. In order to permit disconnection of adapter assembly 200 and handle assembly 100 from one another, button 342 is depressed or actuated, against the bias of biasing member 344, to disengage lip 342a of button 342 and lip 108b of connecting portion 108 of handle housing 102 of handle assembly 100.

As illustrated in FIGS. 1 and 66-80, reload 400 is configured for operable connection to adapter assembly 200 and is configured to fire and form an annular array of surgical staples, and to sever a ring of tissue.

Reload 400 includes a shipping cap assembly (not shown) that is selectively received on a distal end 402 of reload 400 and can function to facilitate insertion of reload 400 into a target surgical site and to maintain staples "S" (FIG. 67) within a staple cartridge 420 of reload 400. Shipping cap assembly 401 also functions to prevent premature advancement of a staple driver assembly 430 (FIG. 66) of reload 400 and of a knife assembly 440 (FIG. 66) of reload 400 prior to and during attachment of reload 400 to adapter assembly 200.

With reference now to FIGS. 66-72, reload 400 includes a housing 410 having a proximal end portion 410a and a distal end portion 410b, a staple cartridge 420 fixedly secured to distal end portion 410b of housing 410, a staple driver assembly 430 operably received within housing 410, a knife assembly 440 operably received within housing 410, a bushing member 450 received within proximal end 410a of housing 410, and a chip assembly 460 mounted about bushing member 450.

Housing 410 of reload 400 includes an outer cylindrical portion 412 and an inner cylindrical portion 414. A plurality of ribs (not shown) interconnects outer and inner cylindrical portions 412, 414. Outer cylindrical portion 412 and inner cylindrical portion 414 of reload 400 are coaxial and define a recess 412a (FIG. 67) therebetween configured to operably receive staple driver assembly 430 and knife assembly 440. Inner cylindrical portion 412 of reload 400 includes a plurality of longitudinally extending ridges 416 (FIG. 67) projecting from an inner surface thereof and configured for radially aligning (e.g., clocking) anvil assembly 510 with reload 400 during a stapling procedure. As will be described in further detail below, proximal ends 416a of longitudinal ridges 416 are configured to facilitate selective securement of shipping cap assembly 401 with reload 400. An annular ridge 418 (FIG. 67) is formed on an outer surface of inner cylindrical portion 412 and is configured to assist in maintaining knife assembly 440 in a retracted position.

Staple cartridge 420 of reload 400 is fixedly secured on distal end 410b of housing 410 and includes a plurality of staple pockets 421 formed therein which are configured to selectively retain staples "S".

With continued reference to FIGS. 66-72, staple driver assembly 430 of reload 400 includes a driver adapter 432 and a driver 434. A proximal end 432a of driver adapter 432 is configured for selective contact and abutment with support base 255d of outer flexible band assembly 255 of second force/rotation transmitting/converting assembly 250 of adapter assembly 200. In operation, during distal advancement of outer flexible band assembly 255, as described above, support base 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples "S". Accordingly, advancement of driver 434 relative to staple cartridge 420 causes ejection of the staples "S" from staple cartridge 420.

Still referring to FIGS. 66-72, knife assembly 440 of reload 400 includes a knife carrier 442 and a circular knife 444 secured about a distal end 442b of knife carrier 442. A proximal end 442a of knife carrier 442 is configured for operable connection with support base 265d of inner flexible band assembly 265 of third force/rotation transmitting/converting assembly 260 of adapter assembly 200. In operation, during distal advancement of inner flexible band assembly 265, as described above, support base 265d of inner flexible band assembly 265 connects with proximal end 442a of knife carrier 442 to advance knife carrier 442 and circular knife 444 from a first or proximal position to a second or advanced position to cause the cutting of tissue disposed between staple cartridge 420 and anvil assembly 510.

Distal end 452b of bushing member 450 is secured within a proximal end 414a of inner cylindrical portion 414 of housing 410 by a plurality of ridges 452c formed on distal end 452b of bushing member 450.

Chip assembly 460 of reload 400 includes a housing 461 from which annular flange 462 extends. Annular flange 462 extends perpendicular to a longitudinal axis of housing 461. Annular flange 462 is configured to be received about a distal end 452b of bushing member 450.

Chip assembly 460 of reload 400 includes a circuit board assembly 464 secured within a cavity 461a of housing 461. Circuit board assembly 464 includes a circuit board 464a, a pair of contact members 464b and a chip 464c (e.g., storage device 405). A first end of circuit board 464a supports chip 464c, and a second end of circuit board 464a supports first and second contact members 464b. Chip 464c is a writable/erasable memory chip. Chip 464c includes the following stored information: lot number, staple size, knife diameter, lumen size, fire count, manufacturing stroke offsets, excessive force index, shipping cap assembly presence, and demonstration modes. Chip 464c includes write capabilities which allow power handle 101 to encode to chip 464c that reload 400 has been used to prevent reuse of an empty, spent or fired reload.

In addition to the foregoing, it is contemplated that chip 464c (e.g., storage device 405) of chip assembly 460 of reload 400 is configured to be written to before, during and/or after a surgical procedure with certain performance data related to the currently performed surgical procedure, or to previously performed surgical procedures. Such performance data may be written to chip 464c upon completion of a successful firing, or upon an unsuccessful firing of the surgical device, e.g., where the power handle 101 enters a recovery state, as described herein.

Such performance data includes and is not limited to clamping force for the surgical procedure, stapling force for the surgical procedure, and/or cutting force for the surgical procedure (e.g., maximum clamping force, stapling force, and/or cutting force). This performance data is also written to the event log of the memory 141 of the main controller 147 of power handle 101, and is recorded in raw data files.

In this manner, in instances where the reload 400 is separated from the adapter 200 and/or power handle 101, and returned to a reprocessing facility, to the manufacturer or some other facility for disposal, repair, recycling, refurbishing, reprocessing, diagnostic testing or the like. Accordingly, with the performance data and other aforementioned information stored in chip 464c of reload 400, when the reload 400 is returned to a facility as part of a field return or the like, the performance data and other aforementioned information may be downloaded or accessed off of chip 464c to provide technicians with information about the firing conducted with that reload 400 by power handle 101. The reprocessing facility may include, and is not limited to, a location in the operating room that is inside the sterile field of the surgery (e.g., in the field of use); and/or a location in the operating room that is outside of the sterile field of the surgery, a dedicated area/location within the hospital or venue performing the surgery, and/or at a dedicated location outside of the hospital or venue performing the surgery (e.g., out of the field of use).

The data that is downloaded off of chip 464$c$ of reload 400 may be used to diagnose or troubleshoot root causes of performance issues that may have occurred in the operative field during use, either with the reload 400, the adapter assembly 200, and/or the power handle 101. For example, the data on chip 464$c$ of reload 400 may be use to assist in identifying the particular event log from which a firing in question took place, since the performance data contained on the reload 400 will match the performance data contained on the power handle 101. The performance data, and/or other aforementioned information, stored in chip 464$c$ of reload 400 may be used to provide information about how the firing of that reload 400 was executed by power handle 101, as well as potential information about the conditions of the underlying tissue being operated on and any other surgical conditions (e.g., environmental conditions, physical/operating conditions of reload 400, adapter assembly 200 and/or power handle 101, etc.).

Figure 82A:
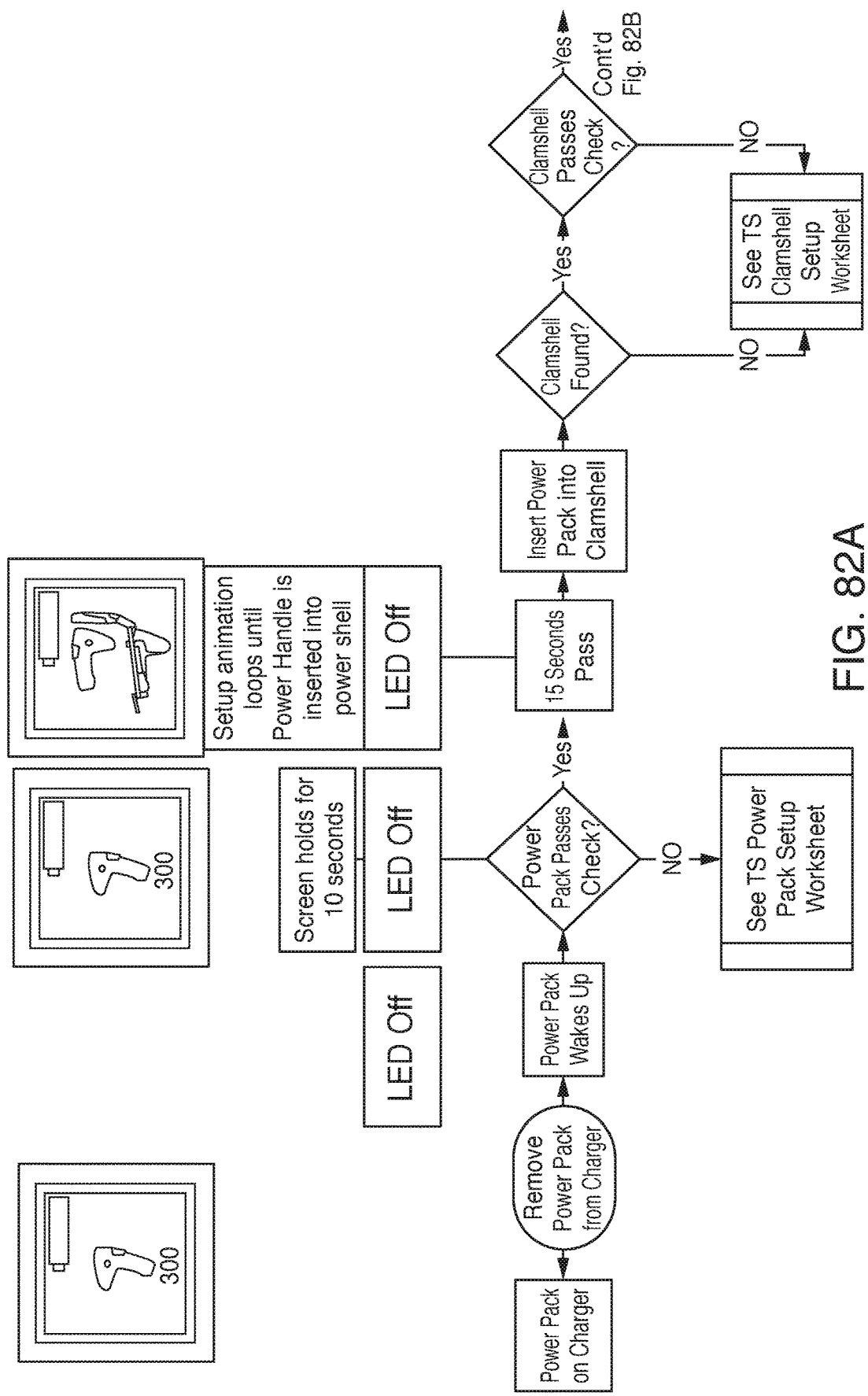
FIGS. 82A-G illustrate a flow chart of a method for operating the handheld surgical device of FIG. 1 according to an embodiment of the present disclosure.
Figure 82B:
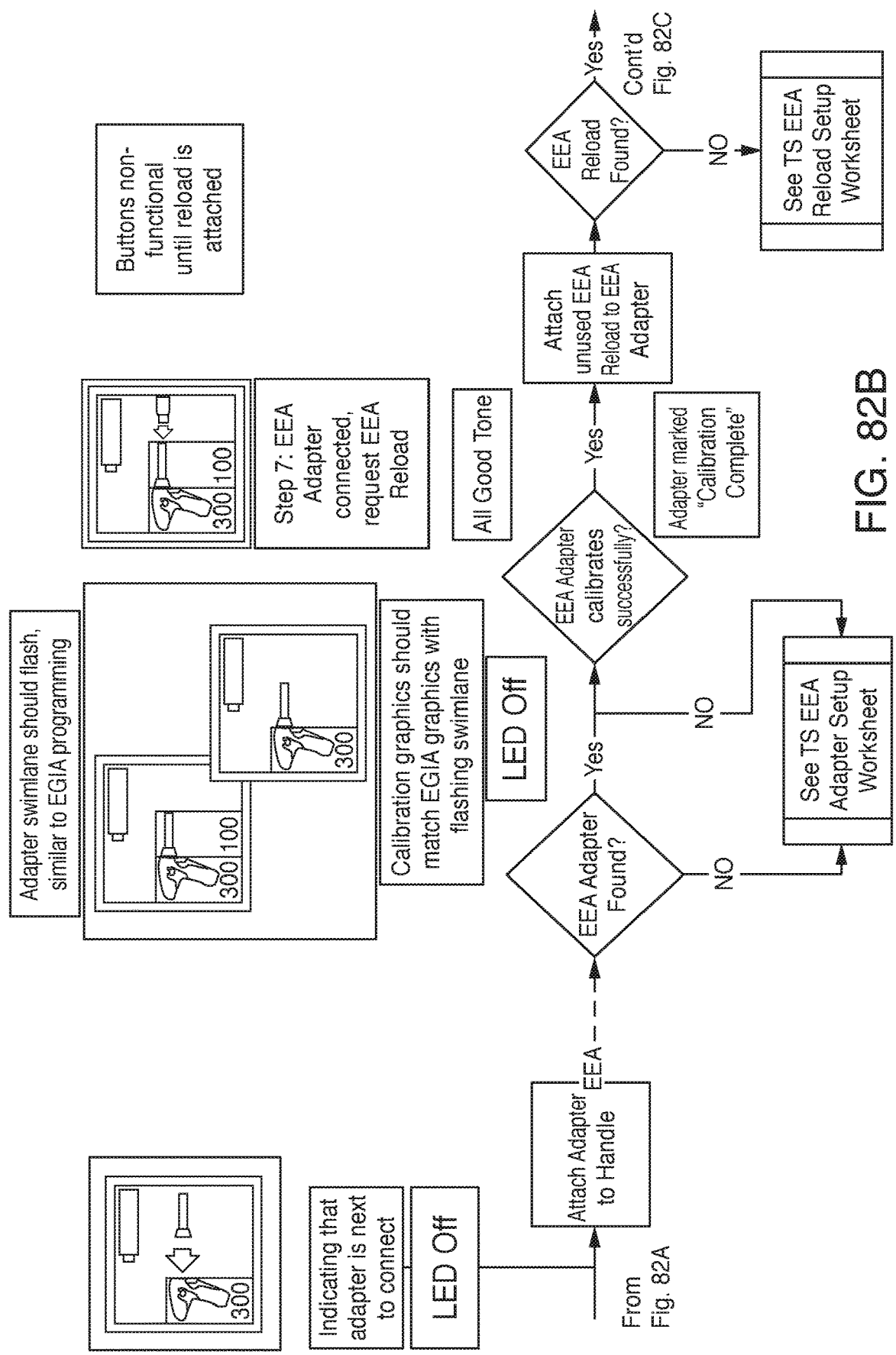
Figures 2, 82C:
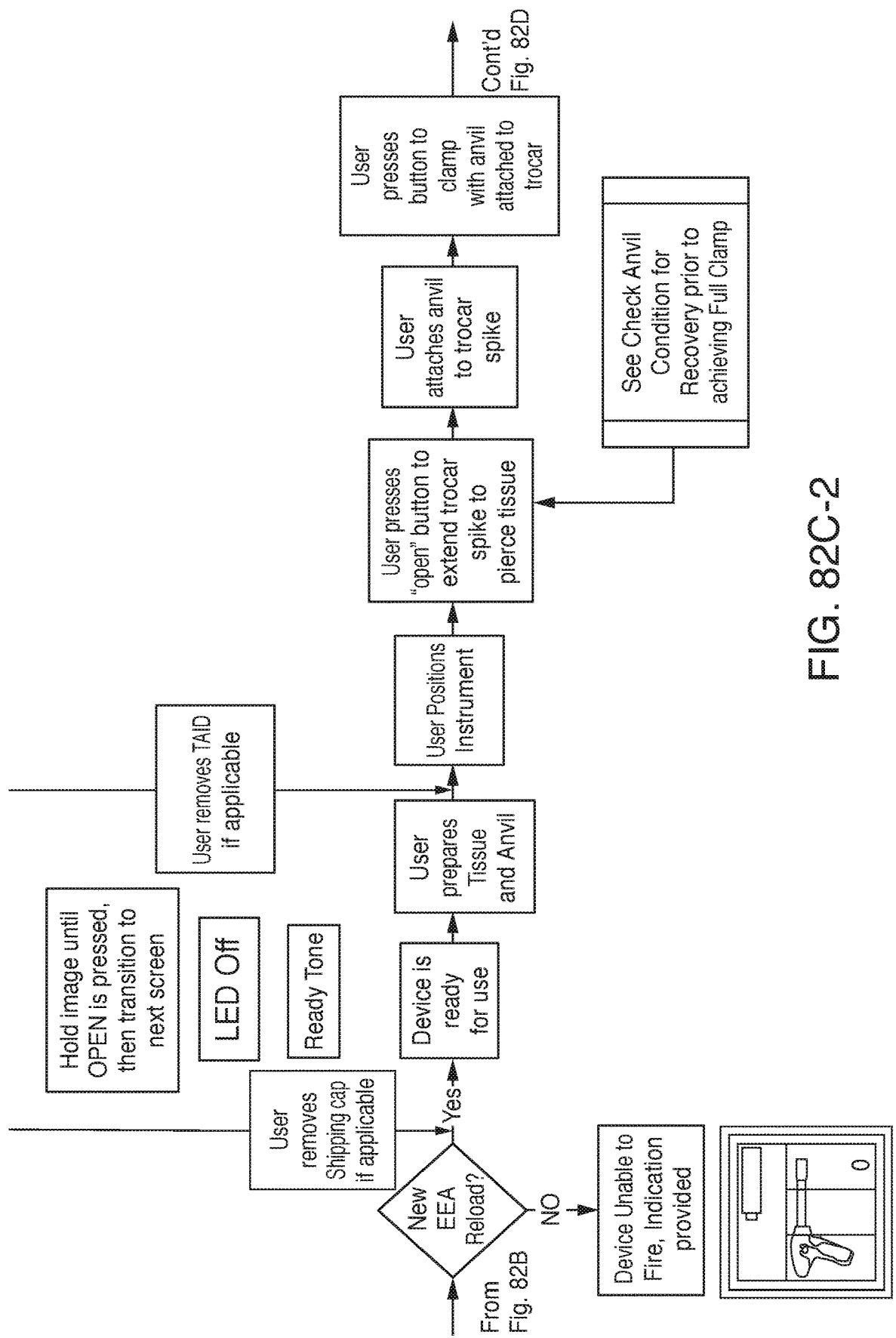
Figures 2, 82D:
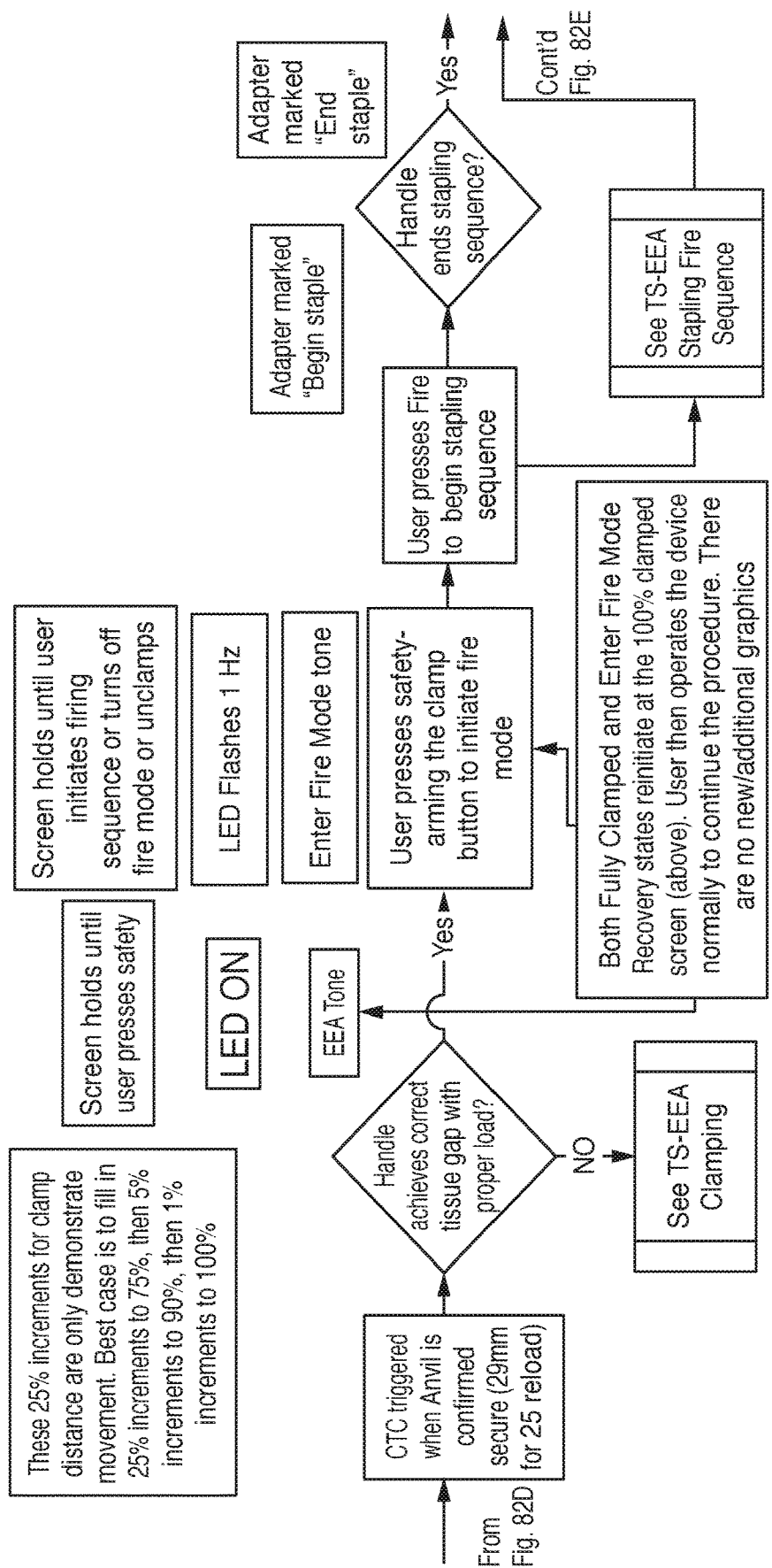

For example, with reference to FIG. 82G, and FIGS. 82A-82F (described in greater detail below), following a successful stapling sequence, as illustrated in FIG. 82D, the procedure enters into a cutting sequence. In accordance with this disclosure, upon a successful cutting sequence or upon an unsuccessful cutting sequence (where power handle 101 enters into a recovery state, as described above), the performance data is written to chip 464$c$ of reload 400. More specifically with regard to the writing of performance data to chip 464$c$, as illustrated in FIG. 82G, during the cutting sequence (to be described in greater detail below), the power handle 101 actuates reload 400 to fire an annular knife 444 of reload 400 (see FIG. 67) to cut tissue clamped between staple cartridge 420 of reload 400 and head assembly 512 of anvil assembly 510. When the cutting sequence is stopped, power handle 101 automatically writes the performance data to chip 464$c$ of reload 400, whether the cutting sequence is stop upon either a successful or unsuccessful cutting.

If the cutting was successful, and with the writing of the performance data to chip 464$c$ of reload 400 complete, the surgical procedure enters a cut complete state where the head assembly 512 of the anvil assembly 510 may be tilted (as described in detail below, and illustrated in FIG. 82F). If the cutting was unsuccessful, and with the writing of the performance data to chip 464$c$ of reload 400 complete, the surgical procedure enters a recover state (e.g., surgical site extraction state) where surgical intervention or the like may be required (as described in detail below, and illustrated in FIG. 82F).

As mentioned throughout, in accordance with the present disclosure, power handle 101 of handle assembly 100 is configured to and capable of actuating/firing reloads 400 of various sizes (e.g., having staples of different length depending on a thickness of tissue to be stapled, and/or having knives of different diameter depending on the diameter of tissue to be anastomosed). In order to be able to fire various reloads 400 each potentially loaded with staples of different lengths, the main controller 147 of power handle 101 is configured and programmed to monitor and record the axial position of outer flexible band assembly 255 and inner flexible band assembly 265 of adapter assembly 200, such that certain lengths of actuation of reloads 400 can be achieved and monitored to ensure proper formation and firing of the particularly sized staples loaded therein, and ensure proper advancement of annular knife 444 to completely cut the tissue drawn within the reload 400 and complete the anastomosis.

In accordance with the present disclosure, since the main controller 147 of power handle 101 monitors the axial position of outer flexible band assembly 255 and inner flexible band assembly 265, a minimum and a maximum length of actuation for each particular reload 400 connected to power handle 101 can be set based on information stored on chip 464$c$ of reload 400 (e.g., staple size, knife diameter, lumen size, minimum cut stroke length, maximum cut stroke length, etc.). For example, the minimum and maximum length of actuation of inner flexible band assembly 265 for a reload 400 having relatively shorter staples will be different than the minimum and maximum length of actuation of inner flexible band assembly 265 for a reload 400 having relatively longer staples. In this manner, the minimum and maximum cut stroke for the annular knife 444 can be set for the particular reload 400 attached. For example, for reloads 400 having relatively shorter staples, the minimum and maximum cut stroke for the respective annular knife 444 can be different than the minimum and maximum cut stroke for the respective annular knife 444 of reloads 400 having relatively longer staples.

Further, in accordance with the present disclosure, by monitoring a maximum cut stroke for the inner band assembly 265 (associated with a particular reload 400), excessive cut band actuation and/or tissue compression may be avoided. Specifically, a maximum cut stroke for the inner band assembly 265 may be set by the main controller 147 of power handle 101 depending on the particular reload 400 connected to the power handle 101 (via adapter assembly 200). Thereafter, the main controller 147 monitors and records the axial position of the inner band assembly 265 to confirm that the maximum cut stroke (previously set) is not exceeded.

As mentioned above, and in accordance with the present disclosure, a value for the minimum and the maximum cut stroke can be specific to each particular reload 400 (e.g., based on staple size, knife diameter, etc.), and the value for the minimum and the maximum cut stroke can be changed for each firing of power handle 101 based on information stored on chip 464$c$ of reload 400 and/or based on information stored in or communicated to the power handle 101.

Turning back to FIGS. 66-72, proximal end 410$a$ of housing 410 is configured for selective connection to connector sleeve 290 of adapter assembly 200. Specifically, outer cylindrical portion 412 of housing 410 terminates in a proximal cylindrical flange 412$a$ having an inner diameter which is larger than a diameter of a distal end portion 290$a$ of connector sleeve 290 of adapter assembly 200. Further, proximal end 432$a$ of driver adapter 432 has an outer diameter which is smaller than the diameter of distal end portion 290$a$ of connector sleeve 290.

Reload 400 includes a compressible release ring 413 supported on flange 412$a$ of outer cylindrical portion 412 of housing 410. Release ring 413 has a substantially ovoid profile including a relative long axis and a relative short axis. In operation, when radially inward directed forces act along the long axis of release ring 413 (as indicated by arrows "A1" of FIG. 70), release ring 413 flexes radially outwardly along the short axis thereof (as indicated by arrows "A2" of FIG. 70).

Release ring 413 includes a ramp feature 413$a$ projecting radially inwardly and located substantially along the short axis of release ring 413. Ramp feature 413a of release ring 413 extends through a window 412b defined in flange 412a of outer cylindrical portion 412 of housing 410. Ramp feature 413a of release ring 413 projects sufficiently radially inwardly so as to be selectively received in a window 290b defined in distal end portion 290a of connector sleeve 290.

Reload 400 includes a retaining ring 415 connected to outer cylindrical portion 412 of housing 410 and configured to help retain release ring 413 on outer cylindrical portion 412 of housing 410.

For radial alignment and clocking of reload 400 with adapter assembly 200, reload 400 includes a longitudinally extending rib 412c projecting radially inwardly from outer cylindrical portion 412 of housing 410 which is configured for slidable receipt in a longitudinally extending slot 290c defined in distal end portion 290a of connector sleeve 290.

To connect reload 400 with adapter assembly 200, rib 412c of reload 400 is radially aligned with longitudinally extending slot 290c of connector sleeve 290 of adapter assembly 200, reload 400 and adapter assembly 200 are then axially approximated towards one another until distal end portion 290a of connector sleeve 290 is received within flange 412a of outer cylindrical portion 412 of housing 410 and until ramp feature 413a of release ring 413 is received in window 290b of connector sleeve 290, reload 400 and adapter assembly 200 are thus locked together.

When reload 400 is connected with adapter assembly 200, distal electrical connector 322 of adapter assembly 200 is mechanically and electrically connected to chip assembly 460 of reload 400.

To disconnect reload 400 and adapter assembly 200 from one another, release ring 413 is squeezed along the long axis thereof (in the direction of arrows "A1") to thereby remove ramp feature 413a of release ring 413 from within window 290b of connector sleeve 290, and thus allowing reload 400 and adapter assembly 200 to be axially separated from one another.

Referring now to FIGS. 71-75, an anvil assembly 510 is provided and is configured for selective connection to trocar member 274 of adapter assembly 200 and for cooperation with reload 400.

Anvil assembly 510 includes a head assembly 512 and a center rod assembly 514. Head assembly 512 includes a post 516, a housing 518, a cutting ring 522, a cutting ring cover 523, an anvil plate 524, a spacer or washer 525, a cam latch member 526, and a retainer member 527. Post 516 is centrally positioned within housing 518.

With reference still to FIGS. 73-75, anvil plate 524 is supported in an outer annular recess 528 of housing 518 and includes a plurality of staple pockets 530 formed therein and configured to receive and form staples.

Cutting ring 522 includes a central opening which is positioned about post 516 within an inner annular recess of housing 518 between post 516 and outer annular recess 528. Cutting ring 522 is formed from polyethylene. Cutting ring cover 523 is secured to an outwardly facing or proximal surface of cutting ring 522.

Retainer member 527 is positioned in the inner annular recess between cutting ring 522 and a back wall of housing 518. Retainer member 527 is annular and includes a plurality of deformable tabs which engage a rear surface of cutting ring 522. Retainer member 527 prevents cutting ring 522 from moving or being pushed into the inner annular recess of housing 518 until a predetermined force sufficient to deform the tabs has been applied to cutting ring 522. When the predetermined force is reached, e.g., during cutting of tissue, cutting ring 522 is urged into the inner annular recess 536 and compresses the retainer members.

Turning back to FIG. 75, anvil center rod assembly 514 includes a center rod 552, a plunger 554 and a plunger spring 556. A first end of center rod 552 includes a pair of arms 159 which define a cavity 159a. A pivot member 562 is provided to pivotally secure post 516 to center rod 552 such that anvil head assembly 512 is pivotally mounted to anvil center rod assembly 514.

Cam latch member 526 is pivotally mounted within a transverse slot of post 516 of housing 518 and about pivot member 562. Cam latch member 526 has an outer cam profile which permits plunger 554 to move forward as cam latch member 526 rotates in a clockwise direction, and permits plunger 554 to be retracted as cam latch member rotates in a counter-clockwise direction.

Plunger 554 is slidably positioned in a bore formed in the first end of center rod 552. Plunger 554 includes an engagement finger which is offset from the pivot axis of anvil head assembly 512 and biased into engagement with an edge of cam latch 526. Engagement of the finger of plunger 554 with the edge of cam latch 526 presses a leading portion of the edge of cam latch 526 against an inner periphery of cutting ring 522 to urge anvil head assembly 512 to an operative or non-tilted position on center rod 552.

Anvil head assembly 512 may be tilted relative to anvil center rod assembly 514 in a pre-fired tilted position. Tilting of anvil head assembly 512 relative to anvil center rod assembly 514 causes the body portion of cam latch member 526 to engage a finger 166 of plunger 554. As cam latch member 526 rotates with the tilting of anvil head assembly 512, plunger 554 is retracted with the bore of anvil center rod assembly 514, thereby compressing spring 556. In this manner, finger 566 of plunger 554 is distally biased against the body portion of cam latch member 526.

With reference to FIGS. 74-75, a second end of center rod 552 includes a bore 580 defined by a plurality of flexible arms 582. The proximal end of each of the flexible arms 582 includes an internal shoulder dimensioned to releasably engage a shoulder of trocar 274 of trocar assembly 270 of adapter assembly 200 to secure anvil assembly 510 to adapter assembly 200. A plurality of splines 586 are formed about center rod 552. Splines 586 function to align and/or clock anvil assembly 510 with staple cartridge 420 of reload 400.

With reference now to FIGS. 76-81, reload 400 is configured to selective optional connection with an external irrigation source via an irrigation tube 590. Irrigation tube 590 is configured to deliver air or saline to the anastomosis site for the purpose of leak testing, for improved insertion or for insufflating the rectal stump.

Irrigation tube 590 terminates at a proximal end 590a thereof with a proximal luer fitting 591 configured to connect to a syringe (not shown), and at a distal end 590b with a distal fitting 592 configured to selectively snap-fit connect to a port 410c of housing 410 of reload 400. Distal fitting 592 includes a pair of resilient fingers 592a configured to engage respective shoulders 410d defined in port 410c of housing 410.

Figure 89:
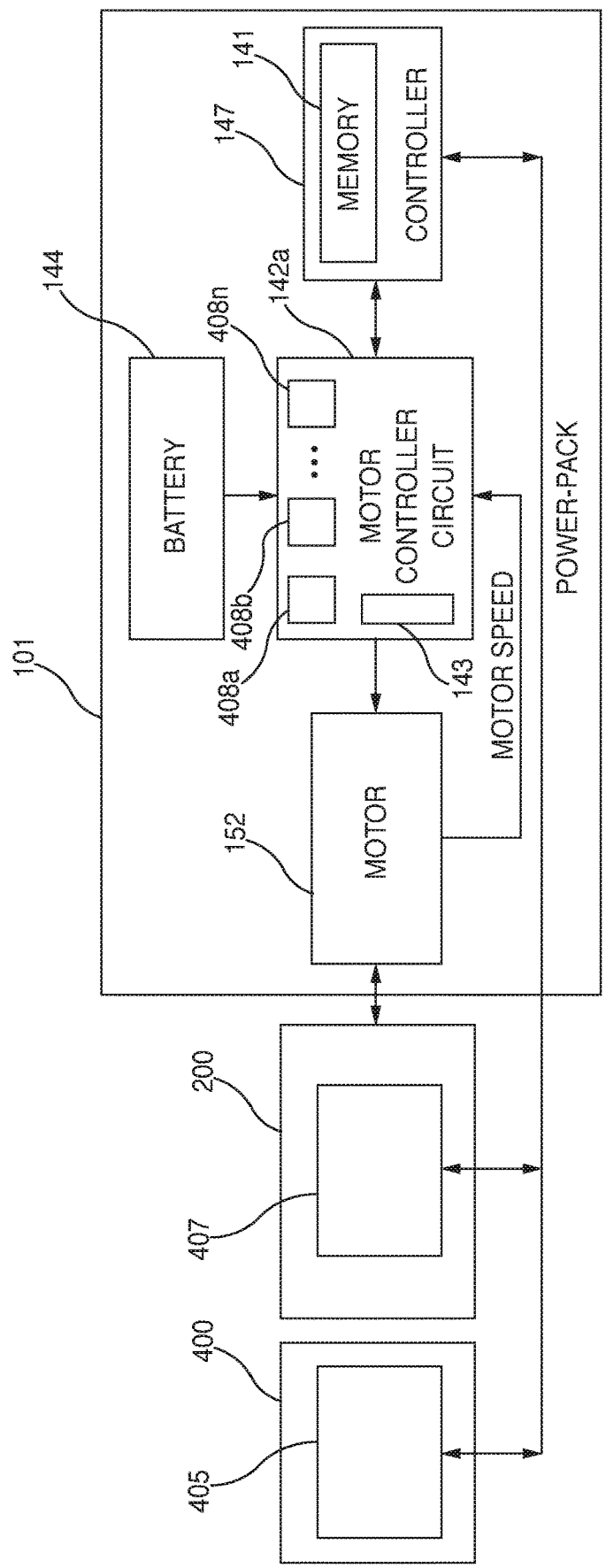
FIG. 89 is a schematic diagram of the handheld surgical device, the adapter assembly, and the reload according to an embodiment of the present disclosure.

With reference to FIG. 89, a schematic diagram of the power handle 101, the circular adapter assembly 200, and the reload 400, is shown. For brevity, only one of the motors 152, 154, 156 is shown, namely, motor 152. The motor 152 is coupled to the battery 144. In embodiments, the motor 152 may be coupled to any suitable power source configured to provide electrical energy to the motor 152, such as an AC/DC transformer.

The battery 144 and the motor 152 are coupled to the motor controller circuit board 142a having a motor controller 143 which controls the operation of the motor 152 including the flow of electrical energy from the battery 144 to the motor 152. The main controller circuit board 142b (FIGS. 12 and 13) includes a main controller 147, which controls the power handle 101. The motor controller 143 includes a plurality of sensors 408a, 408b, 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. Position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the circular adapter assembly 200 and/or the reload 400 by counting revolutions of the motors 152, 154, and 156.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions, which are discussed in more detail below. The main controller 147 is also configured to accept a plurality of user inputs from a user interface (e.g., switches, buttons, touch screen, etc. coupled to the main controller 147).

The main controller 147 is also coupled to a memory 141 that is disposed on the main controller circuit board 142b. The memory 141 may include volatile (e.g., RAM) and non-volatile storage configured to store data, including software instructions for operating the power handle 101. The main controller 147 is also coupled to the strain gauge 320 of the circular adapter assembly 200 using a wired or a wireless connection and is configured to receive strain measurements from the strain gauge 320 which are used during operation of the power handle 101.

The reload 400 includes a data/information storage device 405 (e.g., chip 464c). The circular adapter assembly 200 also includes a storage device 407. The storage devices 405 and 407 include non-volatile storage medium (e.g., EEPROM) that is configured to store any data pertaining to the reload 400 and the circular adapter assembly 200, respectively, including but not limited to, usage count, identification information, model number, serial number, staple size, knife diameter, stroke length, maximum actuation force, minimum actuation force, factory calibration data, and the like.

In embodiments, the data may be encrypted and is only decryptable by devices (e.g., main controller 147) that have appropriate keys. The data may also be used by the main controller 147 to authenticate the circular adapter assembly 200 and/or the reload 400. The storage devices 405 and 407 may be configured in read only or read/write modes, allowing the main controller 147 to read as well as write data onto the storage device 405 and 407.

Operation of the handle assembly 100, the circular adapter assembly 200, and the reload 400 is described below with reference to FIGS. 82A-F, which shows a flow chart of the operation process. With particular reference to FIG. 82A, the power handle 101 is removed from a charger (not shown) and is activated. The power handle 101 performs a self-check upon activation and if the self-check passes, the power handle 101 displays an animation on the display screen 146 illustrating how the power handle 101 should be inserted into shell housing 10.

After the power handle 101 is inserted into the shell housing 10, the power handle 101 verifies that it is properly inserted into the shell housing 10 by establishing communications with the electrical connector 66 of the shell housing 10, which has a chip (not shown) disposed therein. The chip within the electrical connector 66 stores a usage counter which the power handle 101 uses to confirm that the shell housing 10 has not been previously used. The data (e.g., usage count) stored on the chip is encrypted and is authenticated by the power handle 101 prior to determining whether the usage count stored on the chip exceeds the threshold (e.g., if the shell housing 10 has been previously used).

With reference to FIG. 82B, after the power handle 101 is enclosed within the shell housing 10 to form handle assembly 100, adapter assembly 200 is coupled to handle assembly 100. After attachment of circular adapter assembly 200, handle assembly 100 initially verifies that circular adapter assembly 200 is coupled thereto by establishing communications with the storage device 407 of the circular adapter assembly 200 and authenticates circular adapter assembly 200. The data (e.g., usage count) stored on the storage device 407 is encrypted and is authenticated by the power handle 101 prior to determining whether the usage count stored on the storage device 407 exceeds the threshold (e.g., if the adapter assembly 200 has been previously used). Power handle 101 then performs verification checks (e.g., end of life checks, trocar member 274 missing, etc.) and calibrates circular adapter assembly 200 after the handle assembly 100 confirms that the trocar member 274 is attached.

After circular adapter assembly 200 is calibrated, an unused reload 400, with the shipping cap assembly 401, is coupled to circular adapter assembly 200. The handle assembly 100 verifies that circular reload 400 is attached to circular adapter assembly 200 by establishing communications with the storage device 405 of circular reload 400. With reference to FIG. 82C, power handle 101 also authenticates the storage device 405 and confirms that circular reload 400 has not been previously fired by checking the usage count. The usage count is adjusted and encoded by handle assembly 100 after use of circular reload 400. If circular reload 400 has been previously used, handle assembly 100 displays an error indicating the same on the display screen 146.

The power handle 101 also performs calibration with the reload 400 attached to the circular adapter assembly 200 to determine a starting hard stop position. The main controller 147 calculates the distance travelled by the motors 152, 154, 156 to determine the hard stop. The main controller 147 also utilizes the traveled distance during calibration to confirm that the reload 400 is unused. Thus, if the traveled distance is determined to be above a predetermined hard stop threshold, then the main controller 147 confirms that the staples were previously ejected from the reload 400 and marks the reload 400 as used, if the reload 400 was not properly marked before. Once the anvil assembly 510 is attached, the main controller 147 performs another calibration.

With continued reference to FIG. 82C, upon attaching circular reload 400 and confirming that circular reload 400 is unused and has been authenticated, handle assembly 100 prompts the user to eject the shipping cap assembly 401 by prompting the user to press up on the toggle control button 30. The prompt is displayed as an animation on the display screen 146 with a flashing arrow pointing toward the toggle control button 30. The user depresses the upper portion of the toggle control button 30, which activates an automatic extension (and retraction) of trocar member 274 until the shipping cap assembly 401 is ejected, at which point the shipping cap ejection process is complete and the handle assembly 100 is now ready for use.

In embodiments, the circular adapter assembly 200 also operates with reloads 400 having disposable trans-anal/abdominal introducers. Once the reload 400 with the introducer is attached, handle assembly 100 shows a ready screen. This allows the user to insert circular adapter assembly 200 along with the reload 400 more easily through intra-abdominal incisions. Thus, when the toggle control button 30 is pressed, a prompt for ejecting the introducer is displayed, which is similar to the animation for ejecting the shipping cap assembly 401. The user depresses the upper portion of the toggle control button 30, which activates an automatic extension (and retraction) of the trocar member 274 until the introducer is ejected, at which point the introducer ejection process is complete.

With continued reference to FIG. 82C, after the shipping cap assembly 401 or the introducer is removed, the user commences a surgical procedure which includes preparing the target tissue area and positioning circular adapter assembly 200 within the colorectal or upper gastrointestinal region or until trocar member 274 extends sufficiently to permit piercing of tissue. The user presses the toggle control button 30 to extend the trocar member 274 until it pierces tissue. While the trocar member 274 is extending, an animation illustrating the extension process is displayed on the display screen 146. In addition, distance traveled by the trocar member 274 is shown as a scale and the direction of the movement of the trocar member 274 is shown via an arrow. The trocar member 274 is extended until it reaches the maximum extension distance which is indicated on the display screen 146.

Figure 86:
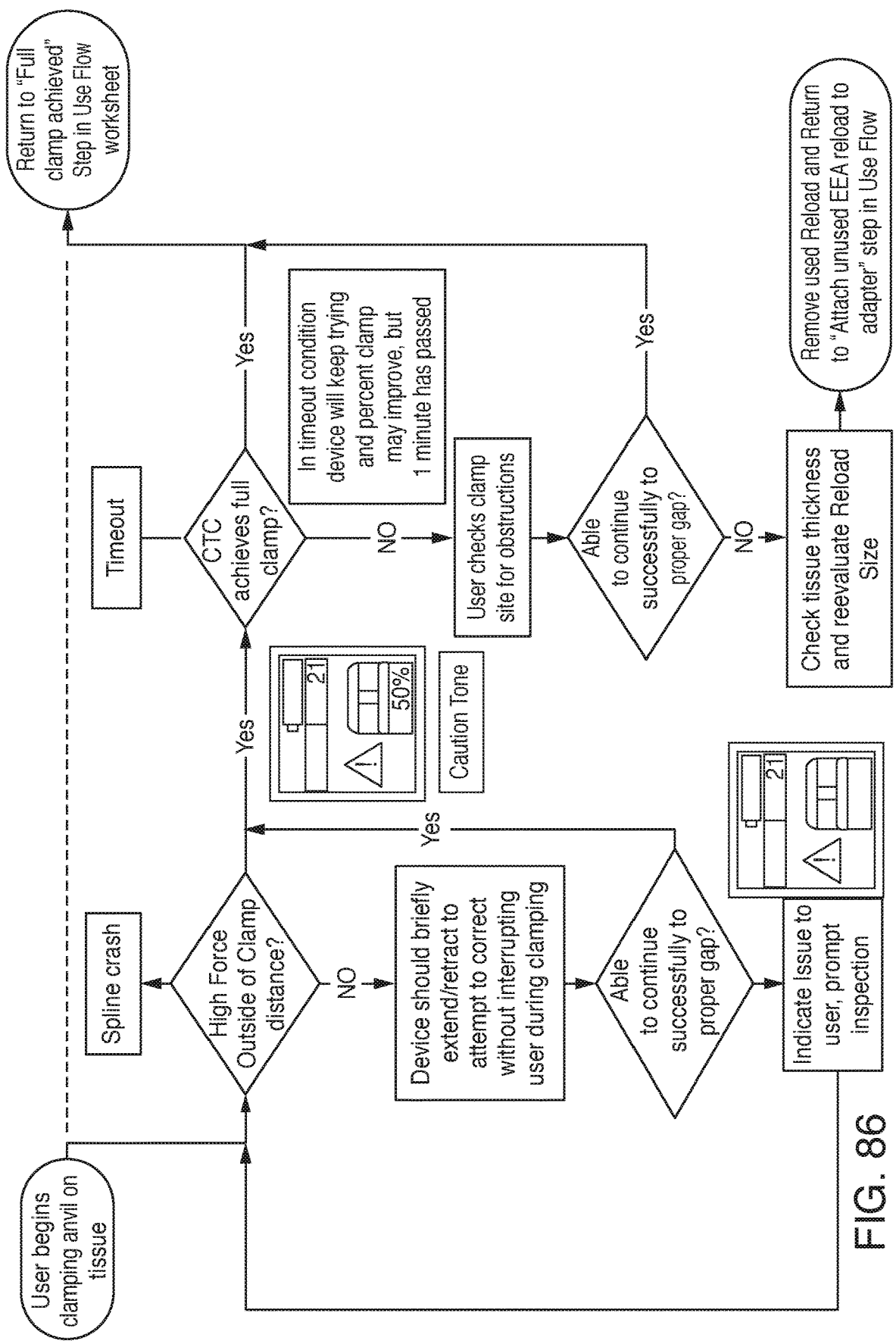
FIG. 86 illustrates a flow chart of a method for controlled tissue compression algorithm executed by the handheld surgical device of FIG. 1 according to an embodiment of the present disclosure.

With reference to FIGS. 82C-D and 86, which shows a flow chart of the clamping process, after extension of the trocar member 274, the anvil assembly 510 (already positioned by surgeon) is attached to the trocar member 274 and the user begins the clamping process on the tissue interposed between circular reload 400 and the anvil assembly 510 by pressing on the bottom of the toggle control button 30. The clamping process is also shown as an animation on the display screen 146, but as a reverse of the animation of the extension of the trocar member 274, e.g., an arrow is highlighted illustrating the retraction direction.

During clamping, the anvil assembly 510 is retracted toward the circular reload 400 until reaching a fully compressed position, namely position of the anvil assembly 510 at which the tissue is fully compressed between the anvil assembly 510 and the reload 400. Fully compressed distance varies for each of the different types of reloads (e.g., the distance is about 29 mm for 25 mm reloads). While clamping, the strain gauge assembly 320 continuously provides measurements to the main controller on the force imparted on the first rotation transmitting assembly 240 as it moves the anvil assembly 510.

With reference to FIG. 83, which schematically illustrates the travel distance and speed of the anvil assembly 510 as it is retracted by the first motor 152, the anvil assembly 510 is initially retracted from a full open position marker 600 at a first speed for a first segment from the full open position marker 600 to a first distance marker 602. Thereafter, the anvil assembly 510 traverses a second distance from the first distance marker 602 to a second distance marker 604 at the second speed, which is slower than the first speed. As the anvil assembly 510 is traversing the second segment, the main controller 147 continuously verifies whether the measured force is within predefined parameters to determine if the measured force exceeds a high force threshold limit prior to reaching a starting compression distance (FIGS. 83 and 86). This measurement is used to detect misalignment of the splines 586 of trocar member 274 with longitudinally extending ridges 416 of the reload 400. If the force is higher than the high force threshold, then the power handle 101 temporarily reverses the rotation transmitting assembly 240 to retract the anvil assembly in an attempt to correct the misalignment of the splines 586. The main controller 147 then reattempts to continue clamping until a third distance marker 604 is reached. If the third distance marker 604 is not reached within a predetermined period of time, the main controller 147 then issues an error, including an alarm on the display screen 146 prompting the user to inspect the anvil assembly 510. After inspection and clearance of any obstruction, the user may then restart the clamping process.

Once the anvil assembly 510 reaches the third distance marker 604 at the end of the second segment, the power handle 101 performs a rotation verification to check position of the anvil assembly 510. Then the main controller commences a controlled tissue compression ("CTC") algorithm which varies the clamping speed during tissue compression without exceeding a target compression force.

The CTC accounts for slow-changing and rapid-changing forces imparted on the tissue during compression with a second-order predictive force filter. As the predicted force approaches the target force, the clamping speed is slowed to prevent over-shoot. When the measured force reaches the target force and the clamp gap has not yet been achieved, clamping is stopped to allow for tissue relaxation. During tissue relaxation, after the measured force falls below the target clamping force, the CTC recommences. The force exerted on tissue is derived from the strain measurements by the main controller 147 from the strain gauge assembly 320.

During CTC, the user continues to press down on the toggle control button 30 to continue operation of handle assembly 100. The third distance marker 604, at which the controller commences the CTC, corresponds to the distance at which the anvil assembly 510 begins to compress the tissue against the staple guide of the circular reload 400 for the remainder of the clamping process. CTC controls the movement of the anvil assembly 510 during a third segment, from the third distance marker 604 to a fourth distance marker 606, which corresponds to the fully compressed position of the anvil assembly 510. CTC continues until the anvil assembly 510 reaches the fourth distance marker 606. During clamping, if no forces are detected, the handle assembly 100 identifies that the anvil assembly 510 is missing and the handle assembly 100 issues an error.

The CTC is run for a predetermined time period, namely, a first time period, and an optional second time period. During execution of the CTC, the main controller monitors force based on strain as measured by the strain gauge assembly 320 that is imparted on the first rotation transmitting assembly 240 as it moves the anvil assembly 510 until the measured force approaches the target clamping force.

During execution of the CTC, the main controller 147 determines whether the measured forces approaches the target clamping force by calculating a predicted clamping force using a second-order predictive filter. Target clamping force may be any suitable threshold from about 100 pounds to about 200 pounds, in embodiments, the target clamping force may be approximately 150 pounds. The CTC calculates a predicted clamping force and compares it to the target clamping force. The main controller samples a plurality of strain gauge values at predetermined frequency (e.g., every 1 millisecond) during a predetermined sampling time period. The main controller 147 then uses a first plurality of strain gauge samples obtained during the sampling time period to calculate a filtered strain gauge value. The main controller 147 stores a plurality of filtered strain gauge values and uses three strain gauge samples to predict the target clamping force. In particular, the main controller 147 initially calculates a first difference between the first two (e.g., first and second) filtered strain gauge values, which provides a first-order comparison. More specifically, the main controller 147 then calculates a second difference between subsequent two filtered strain gauge values (e.g., second and third values). In embodiments, the subsequent filtered strain gauge values may be any other subsequent values, rather than encompassing the second value used to calculate the first difference. The first difference is then divided by the second difference, to obtain a percentage of the difference. The main controller determines the target clamping force based on a predicted strain change, which is calculated by multiplying the first difference by the percentage of the difference and a value representing future periods of strain extrapolation. The predicted strain change is then added to the current filtered strain gauge value to determine a predicted strain value, which corresponds to the predicted clamping force.

If the predicted clamping force is above the target force, the PWM voltage driving the motor 152, which is driving the first rotation transmitting assembly 240 is set to zero. The force is continued to be monitored, and once the force drops below a target threshold, the speed of the motor 152 is set to an updated speed to continue the clamping process. This process repeats until the fourth distance marker 606 is reached.

The target speed is calculated by the main controller 147 based on a strain ratio. The strain ratio is calculated by subtracting the predicated strain value from the target clamping force and dividing the difference by the target clamping force. The strain ratio is then used to determine a speed offset by multiplying a difference between maximum and minimum speeds of the motor 152 by the strain ratio. The speed offset is then added to the minimum speed of the motor 152 to determine the target speed. The target speed is used to control the motor 152 in response to the motor deviating by a predetermined amount from currently set speed (e.g., if the motor 152 deviates by about 50 revolutions per minute). In addition, the motor 152 is set to a newly calculated target speed, if the current speed of the motor 152 is zero, e.g., following the predicted clamping force approaching the target force. This allows for varying the speed of the motor 152 while maintaining the desired force on the tissue during clamping.

The target clamping force is fixed for the first time period. When thick tissue is encountered, the clamp gap may not be attained within the first time period (e.g., reaching the fourth distance marker 606), clamping is stopped, and the operator is notified via the display screen. If the operator chooses to continue the clamping operation, CTC continues to operate for the second time period, during which the target clamping force is incremented until the maximum force is reached. During the second period, clamping movement distance is monitored to determine if the anvil assembly 510 is moved in response to incremental force increases. Thereafter, the clamp distance is periodically monitored for any minimal movement. If no minimal movement is detected, the target force is dynamically incremented by a proportional amount based on a difference between the current clamp position and the fourth distance marker 606. If a maximum force, which is higher than the target clamping force, is detected, all clamping is stopped. In addition, if clamping is not achieved within the second time period, then the CTC issues an alarm. This may include instructing the user on the display screen 146 to check the clamp site for obstructions. If none are found, the user may continue the clamping process. If the clamping is not complete, e.g., second time period expires and/or the maximum force limit is reached, another alarm is triggered, instructing the user to check tissue thickness and to use a larger reload 400 to restart the clamping process.

With reference to FIGS. 82C-D and 86, once CTC is commenced, the display screen 146 displays a CTC user interface after the main controller 147 confirms that the anvil assembly 510 is present based on detection of a minimum force. In particular, the distance scale on the display screen 146 is replaced with a gauge illustrating the force being imparted on the tissue, and the trocar is replaced with the anvil and tissue being compressed. Also displayed is the progress of the clamping until the fourth distance marker 606 is reached. Thus, as the anvil assembly 510 is being moved to compress the tissue under the CTC, the gauge, the anvil animation, and the distance traveled by the anvil assembly 510 are updated continuously to provide real time feedback regarding the CTC progress.

During CTC, the strain gauge assembly 320 continuously provides measurements to the main controller on the force imparted on the first rotation transmitting assembly 240 as it moves the anvil assembly 510. The force measured by the strain gauge assembly 320 is represented by the gauge on the display screen 146, which is separated into three zones, zone 1 shows the force from 0% to 50% of the target clamp force, zone 2 shows the force from 51% to 100%, and zone 3 shows the maximum force above the target clamp force. High force caution graphic is displayed on screen for zone 3, the user is required to perform a second activation of the toggle to confirm clamping despite zone 3 high forces.

The user can then press the toggle control button 30 to re-clamp, which would move the anvil assembly 510 until the force reaches the maximum force limit of zone 3. This allows for further compression of the tissue in certain circumstances where the user deems it necessary, e.g., based on tissue thickness. Once the CTC algorithm is complete and tissue is compressed, handle assembly 100 activates an LED and issues a tone indicating the same and the CTC screen indicating 100% compression is continuously displayed on the display screen 146 until the stapling sequence is started. A pre-fire calibration is performed prior to commencement of the stapling sequence.

Figure 87A:
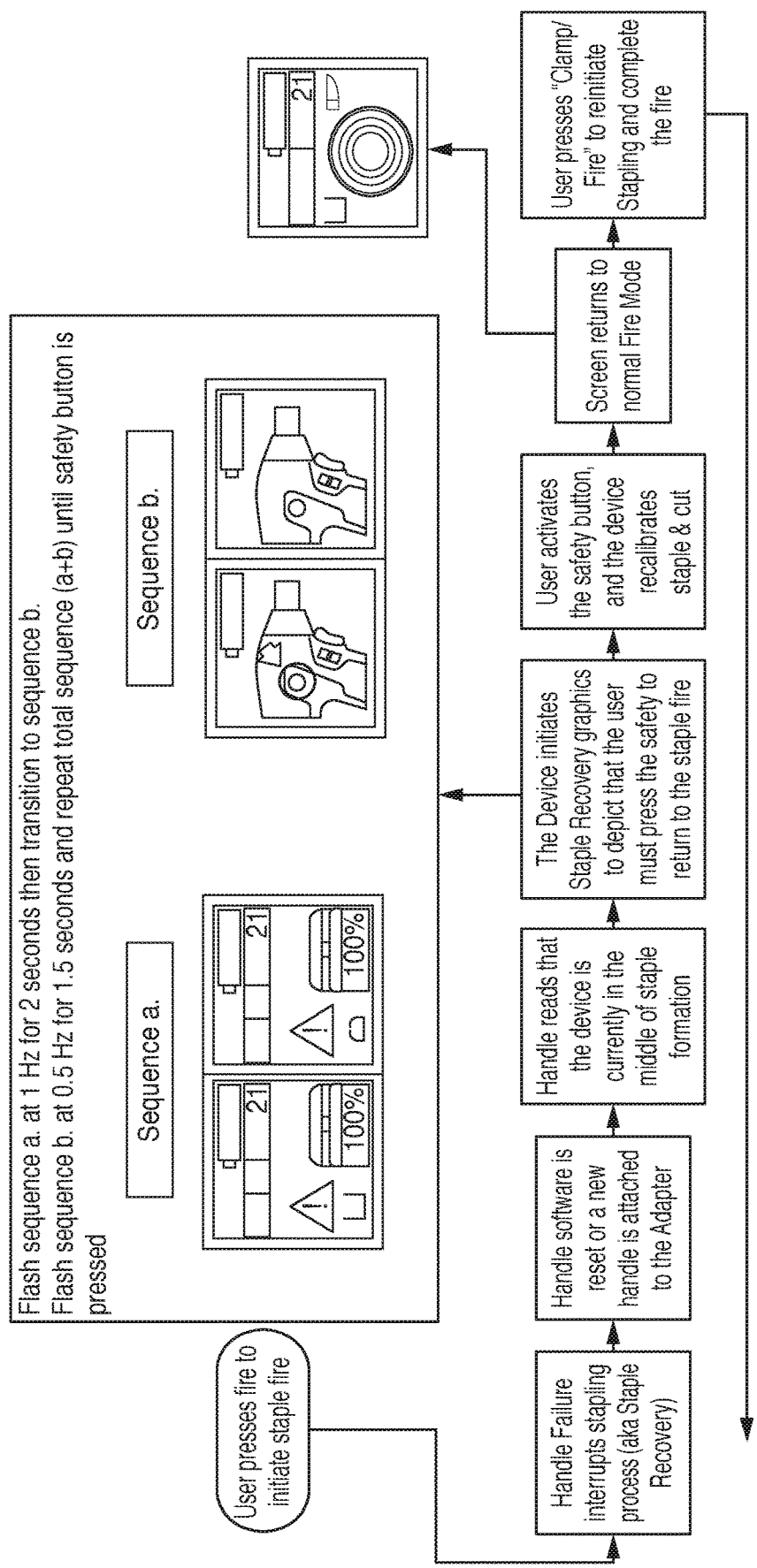
FIGS. 87A-B illustrate a flow chart of a method for a stapling algorithm executed by the handheld surgical device of FIG. 1 according to an embodiment of the present disclosure.
Figure 87B:
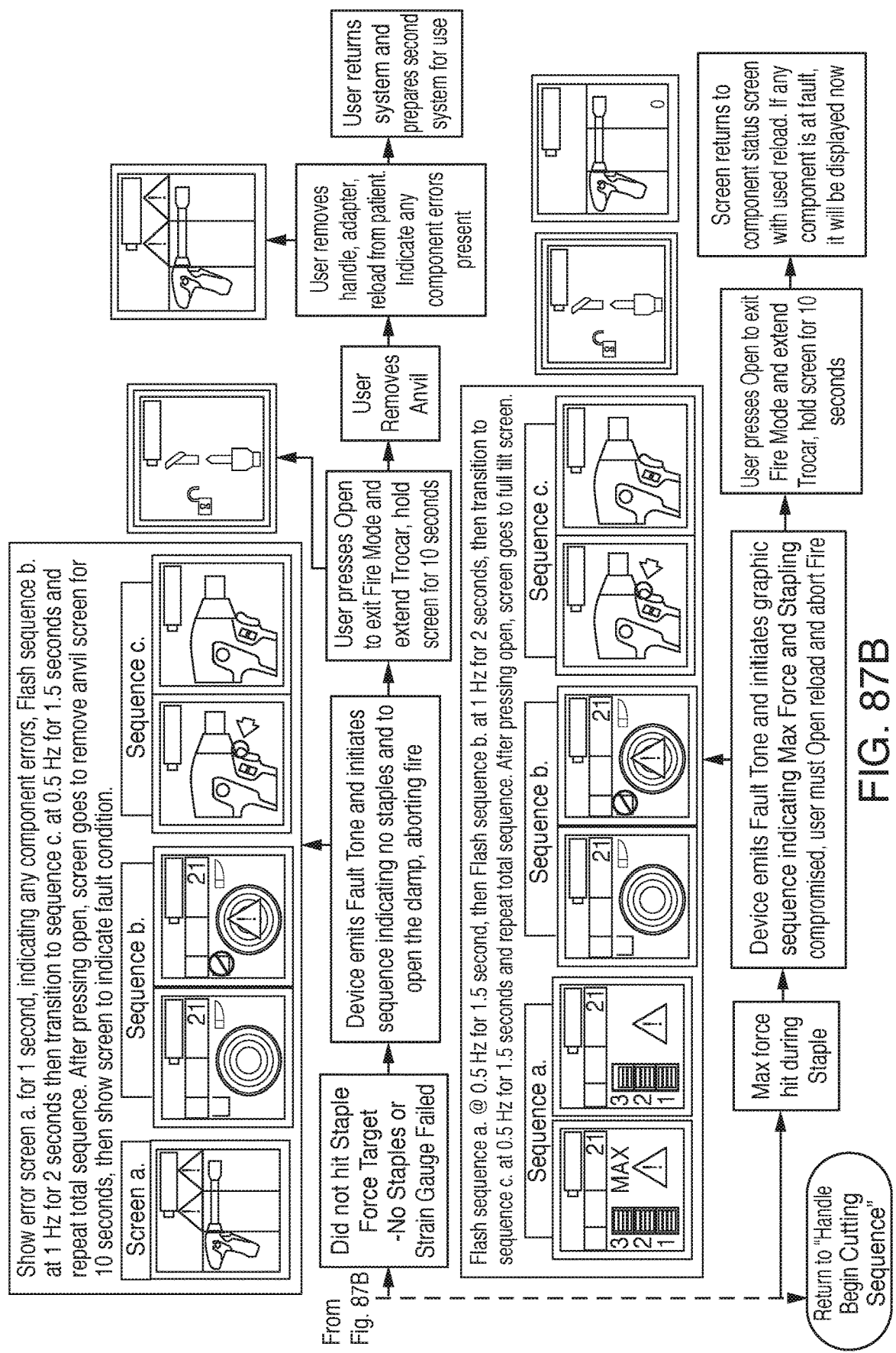

With reference to FIGS. 82D and 87A-B, to initiate stapling sequence, the user presses one of the safety buttons 36a or 36b of the power handle 101, which acts as a safety and arms the toggle control button 30, allowing it to commence stapling. Upon activation of the safety button 36a or 36b, a second rotation verification calibration check is performed. The display screen 146 transitions to the stapling sequence display, which includes a circle illustrating an animated view of a circular anastomosis, a progress bar, and a staple icon. The stapling sequence screen is displayed until user initiates the stapling sequence, exits the stapling sequence, or unclamps. At the start of the stapling sequence, the LED begins to flash and an audio tone is played. The LED continues to flash throughout the duration of the stapling and cutting sequences.

To commence the stapling sequence, the user presses down on the toggle control button 30, which moves the second rotation transmitting assembly 250 to convert rotation to linear motion and to eject and form staples from circular reload 400. In particular, during the firing sequence, the second motor 152 advances the driver 434 using the second rotation transmitting assembly 250. The force imparted on the second rotation transmitting assembly 250 is monitored by the strain gauge assembly 320. The process is deemed complete once the second rotation transmitting assembly 250 reaches a hard stop corresponding to a force threshold and detected by the strain gauge assembly 320. This indicates that the staples have been successfully ejected and deformed against the anvil assembly 510.

With reference to FIG. 84, which schematically illustrates the travel distance and speed of the second motor 154 as it advances the driver 434, driver 434 is initially advanced from a first position marker 608 (e.g., hardstop) at a first speed for a first segment from the first distance marker 608 to a second distance marker 610. From the second distance marker 610, the driver 434 is advanced at a second speed, slower than the first speed, until it reaches a third distance marker 612, to eject the staples.

During the first segment, the second motor 154 advances the driver 434 until the driver 434 contacts the staples to commence firing. The main controller 147 also writes to the storage devices 405 and 407 of the reload 400 and the circular adapter assembly 200. In particular, main controller 147 marks the reload 400 as "used" in the storage device 405 and increments the usage count in the storage device 407 of the circular adapter assembly 200.

After reaching the second distance marker 610, the second motor 154 is operated at the second, slower speed to eject the staples from the reload 400. With reference to FIG. 87B, during the second segment, as the staples are ejected from the reload 400 to staple tissue, the main controller 147 continually monitors the strain measured by the strain gauge assembly 320 and determines whether the force corresponding to the measured strain is between a minimum stapling force and a maximum stapling force. The stapling force range may be stored in the storage device 405 of the reload 400 and used by the main controller 147 during the stapling sequence. Determination whether the measured force is below the minimum stapling force is used to verify that the staples are present in the reload 400. In addition, a low force may be also indicative of a failure of the strain gauge 320. If the measured force is below the minimum stapling force, then the main controller 147 signals the second motor 154 to retract the driver 434 to the second distance marker 610. The main controller 147 also displays a sequence on the display 146 instructing the user the steps to exit stapling sequence and retract the anvil assembly 510. After removing the anvil assembly 510, the user may replace the circular adapter assembly 200 and the reload 400 and restart the stapling process.

If the measured force is above the maximum stapling force, which may be about 500 lbs., the main controller 147 stops the second motor 154 and displays a sequence on the display 146 instructing the user the steps to exit the stapling sequence. However, the user may still continue the stapling process without force limit detection by pressing on toggle control button 30.

The main controller 147 determines that the stapling process is completed successfully, if the second motor 154 reached a third distance marker 612 associated with stapled tissue and during this movement the measured strain was within the minimum and maximum stapling force limits. Thereafter, the second motor 154 retracts the driver 434 to a fourth distance marker 614 to release pressure on the tissue and subsequently to the second distance marker 610 prior to starting the cutting sequence.

The main controller 147 is also configured to account for band compression of outer flexible band assembly 255 during the stapling process which may result in a non-linear relationship between motor position as determined by the main controller 147 and position of components of the circular adapter assembly 200. The main controller 147 is configured to resolve the discrepancy between the calculated position of the motors 152, 154, 156 and the actual position of the components of the circular adapter assembly 200 using a second order mapping of force changes that result in the discrepancies. The force changes are based on the strain measurements from the strain gauge assembly 320. In particular, the main controller 147 maintains a count of lost turns by the motors 152, 154, 156, namely, turns that did not result in movement of the components of the circular adapter assembly 200, e.g., due to compression, based on the force imparted on the components of the circular adapter assembly 200. The main controller 147 accumulates the total lost turns each time the imparted force changes by a predetermined amount, e.g., about 5 lbs. The motor position is then adjusted by the total accumulated lost-turns value to determine whether the target position has been attained.

With reference to FIG. 82D, progress of staple firing is illustrated by an animation of the anastomosis, the firing progress bar, and staple formation. In particular, the animation illustrates staple legs penetrating tissue and then forming to create concentric staple lines. Once the stapling sequence is complete, the outer circumference is displayed in green. The staple icon also shows initially unformed staples, and then shows the legs of the staples being curled inward. The progress bar is separated into two segments, the first segment being indicative of the stapling process and the second segment being indicative of the cutting process. Thus, as the stapling sequence is ongoing the progress bar continues to fill until it reaches its midpoint.

Figure 82E:
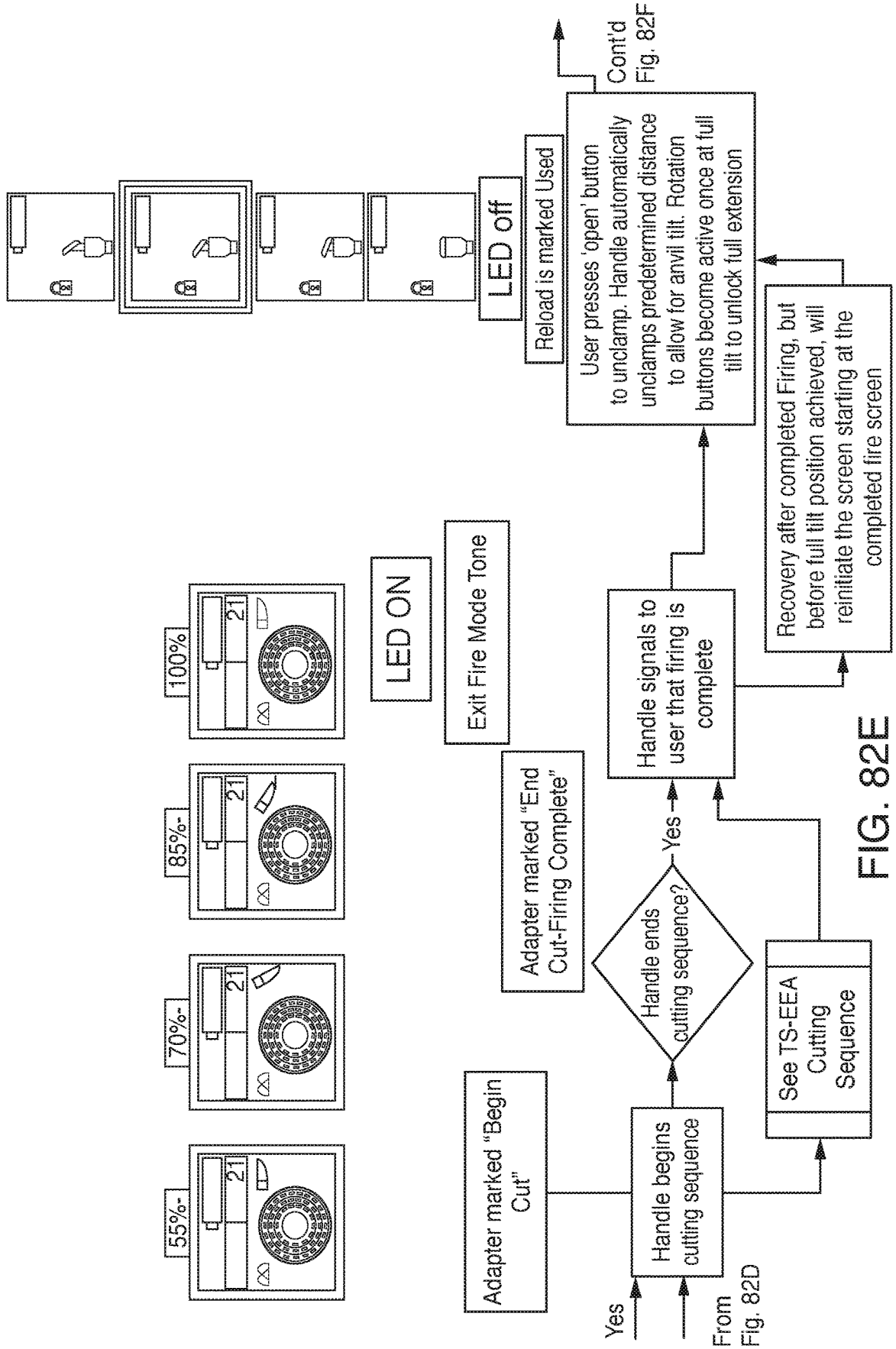
Figure 88A:
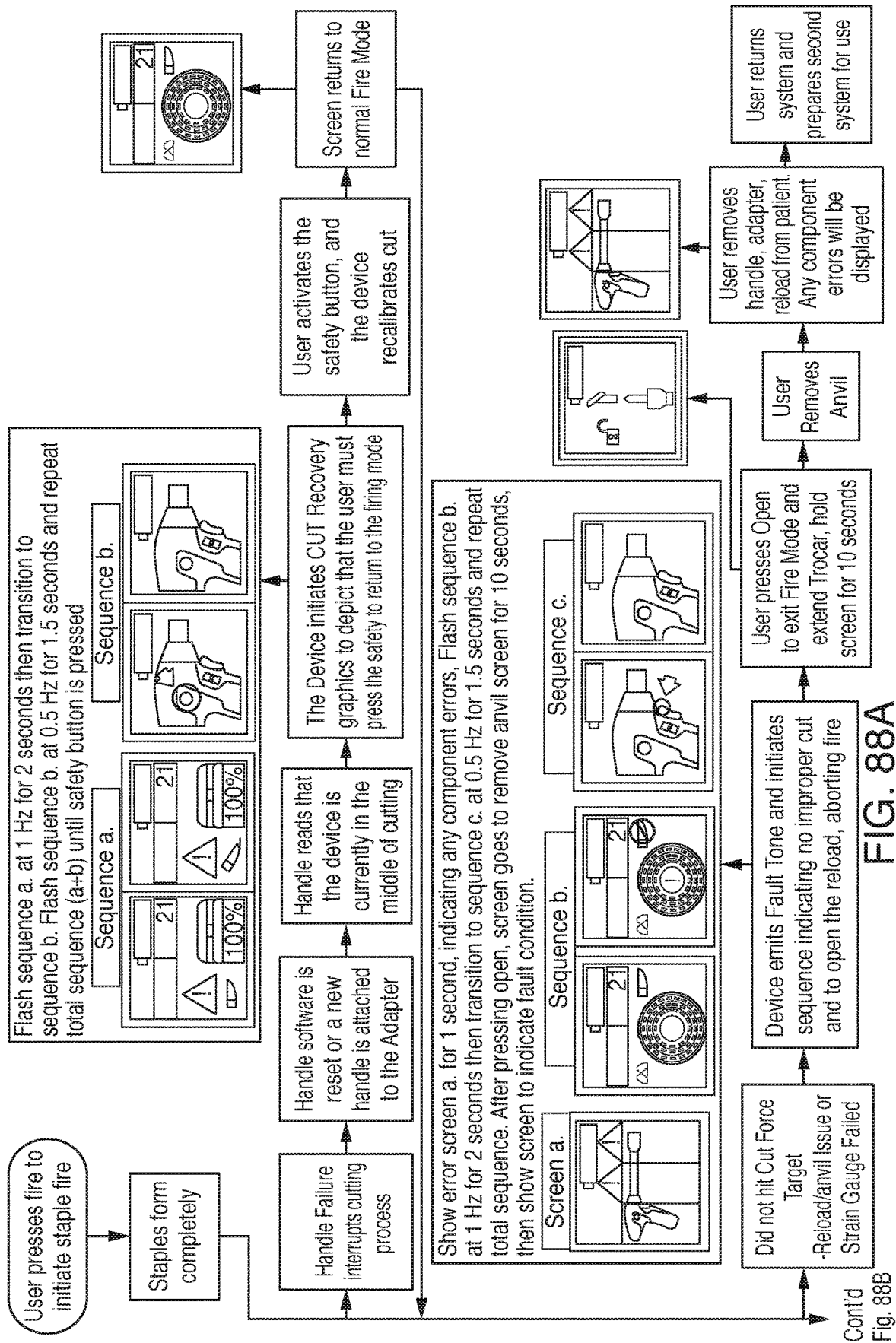
FIGS. 88A-B illustrate a flow chart of a method for a cutting algorithm executed by the handheld surgical device of FIG. 1 according to an embodiment of the present disclosure.
Figure 88B:
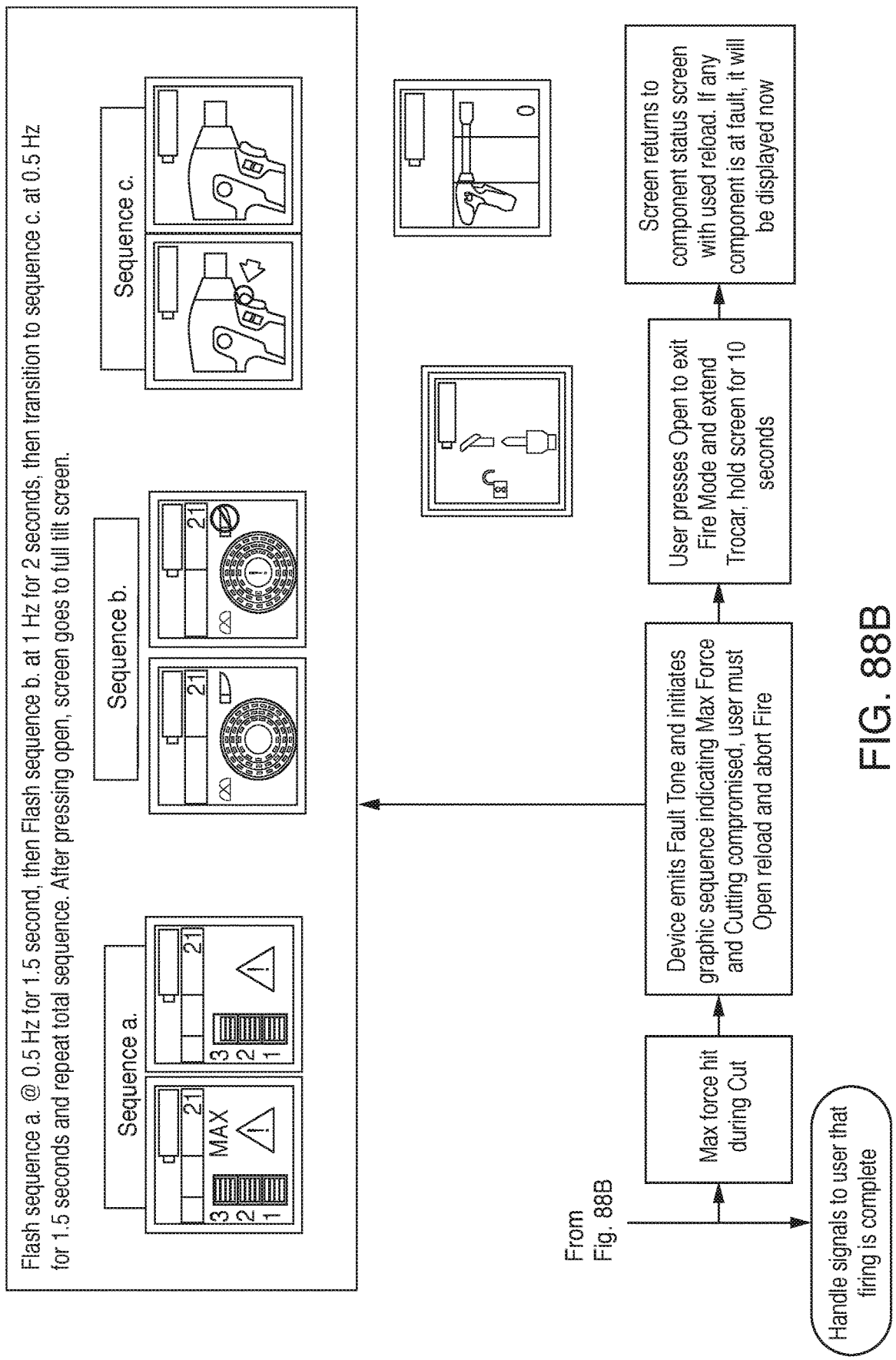

With reference to FIGS. 82E and 88A-B, after the stapling sequence is complete, the power handle 101 automatically commences the cutting sequence. During the cutting sequence, the third motor 154 advances the knife assembly 440 using the third rotation transmitting assembly 260. The force imparted on the third rotation transmitting assembly 260 is monitored by the strain gauge assembly 320. The process is deemed complete once the third rotation transmitting assembly 260 reaches a hard stop corresponding to a force threshold and detected by the strain gauge assembly 320 or a maximum position is reached. This indicates that the knife assembly 320 has cut through the stapled tissue.

With reference to FIG. 85, which schematically illustrates the travel distance and speed of the third motor 156 as it advances the knife assembly 440. The knife assembly 440 is initially advanced from a first position marker 616 at a first speed for a first segment from the first distance marker 616 until a second distance marker 618. From the second distance marker 618, the knife assembly 440 is advanced at a second speed, slower than the first speed, until it reaches a third distance marker 620, to cut the stapled tissue.

During the first segment, the third motor 156 advances the knife assembly 440 until the knife assembly 440 contacts the stapled tissue. After reaching the second distance marker 618, the third motor 154 is operated at the second, slower speed to cut the stapled tissue. With reference to FIGS. 88A-B, during the second segment, as the knife assembly 440 is advanced to cut tissue, the main controller 147 continually monitors the strain measured by the strain gauge assembly 320 and determines whether the force corresponding to the measured strain is between a target cutting force and a maximum cutting force. The target cutting force and the maximum cutting force may be stored in the storage device 405 of the reload 400 and used by the main controller 147 during cutting sequence. If the target cutting force is not reached during the cutting sequence, which is indicative of improper cutting, then the main controller 147 signals the third motor 156 retract the knife assembly 440 allowing the user to open the reload 400 and abort the cutting sequence. The main controller 147 also displays a sequence on the display 146 indicating to the user the steps to exit the cutting sequence and retract the anvil assembly 510. After removing the anvil assembly 510, the user may replace the circular adapter assembly 200 and the reload 400 and restart the stapling process. If the measured force is above the maximum cutting force, the main controller 147 stops the third motor 156 and displays a sequence on the display 146 instructing the user to exit the cutting sequence.

The main controller 147 determines that the stapling process is completed successfully, if the knife assembly 440 being moved by the third motor 156 reached a third distance marker 620 associated with cut tissue and during this movement the measured strain was within the target and maximum cutting force limits. Thereafter, the third motor 154 retracts the knife assembly 440 back to the first distance marker 616.

Each of the distance markers 600-620 are stored in the memory 141 and/or the storage device 405 and are used by the main controller 147 to control the operation of the power handle 101 to actuate various components of the circular adapter assembly 200 based thereon. As noted above the distance markers 600-620 may be different for different type of reloads accounting for variations in staple size, diameter of the reload, etc. In addition, the distance markers 600-620 are set from the hard stop as determined during the calibration process described above.

With reference to FIG. 82E, the cutting sequence is illustrated by the same user interface, except the staple icon is grayed out and a knife icon is highlighted. During the cutting sequence, the knife icon is animated with motion and the progress bar moves from its midpoint to the right. In addition, the inner circumference of the circle is displayed in green once the cutting sequence is complete. During the cutting sequence, the force imparted on the third rotation transmitting assembly 260 is monitored by the strain gauge assembly 320 to ensure that maximum force limit is not exceeded. The process is deemed complete once the third rotation transmitting assembly 260 reaches a hard stop or a force threshold as detected by the strain gauge assembly 320. This indicates that the knife has successfully dissected the tissue. Completion of the cutting sequence is indicated by another tone and the LED stops flashing and remains lit.

Figure 82F:
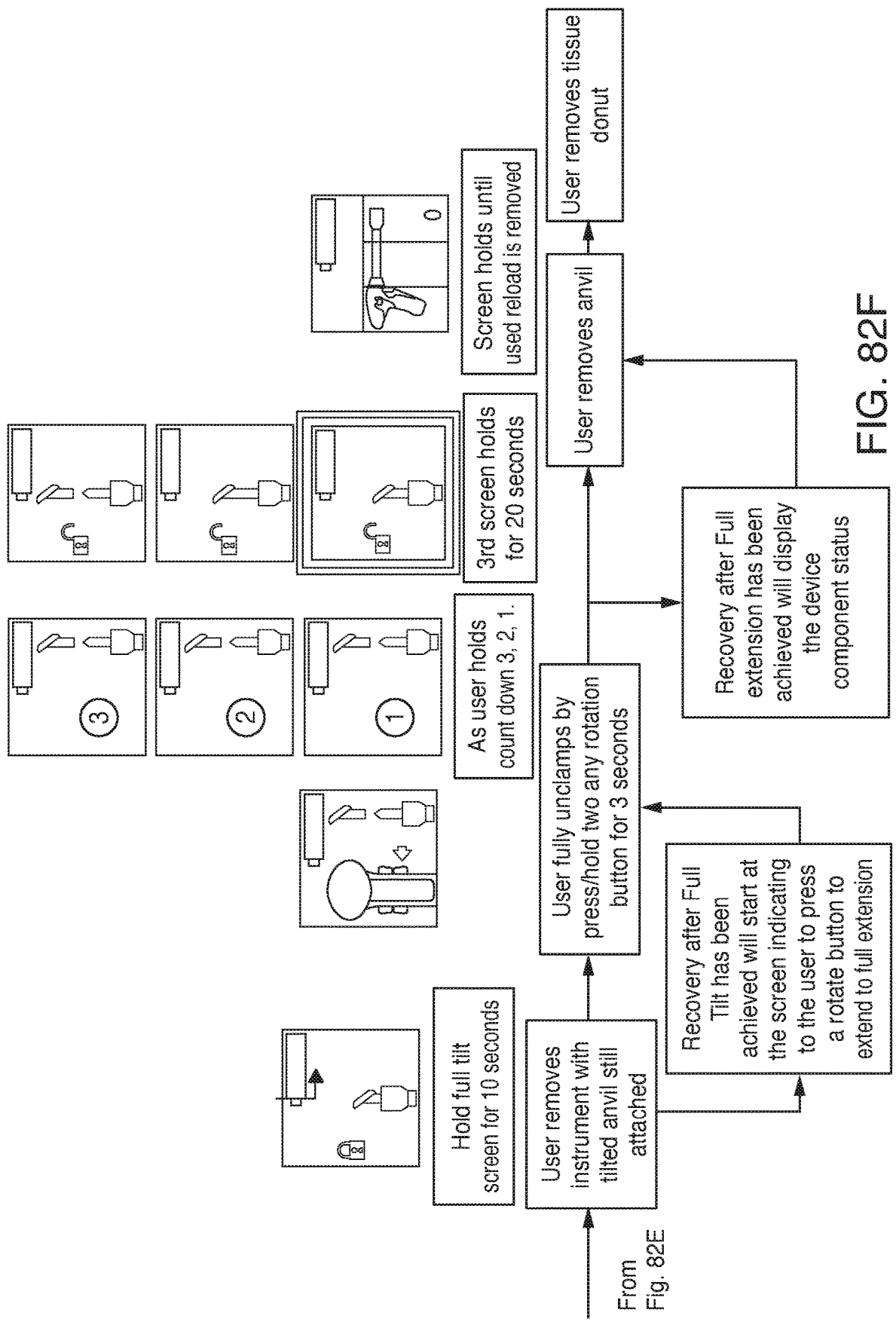
Figure 82G:
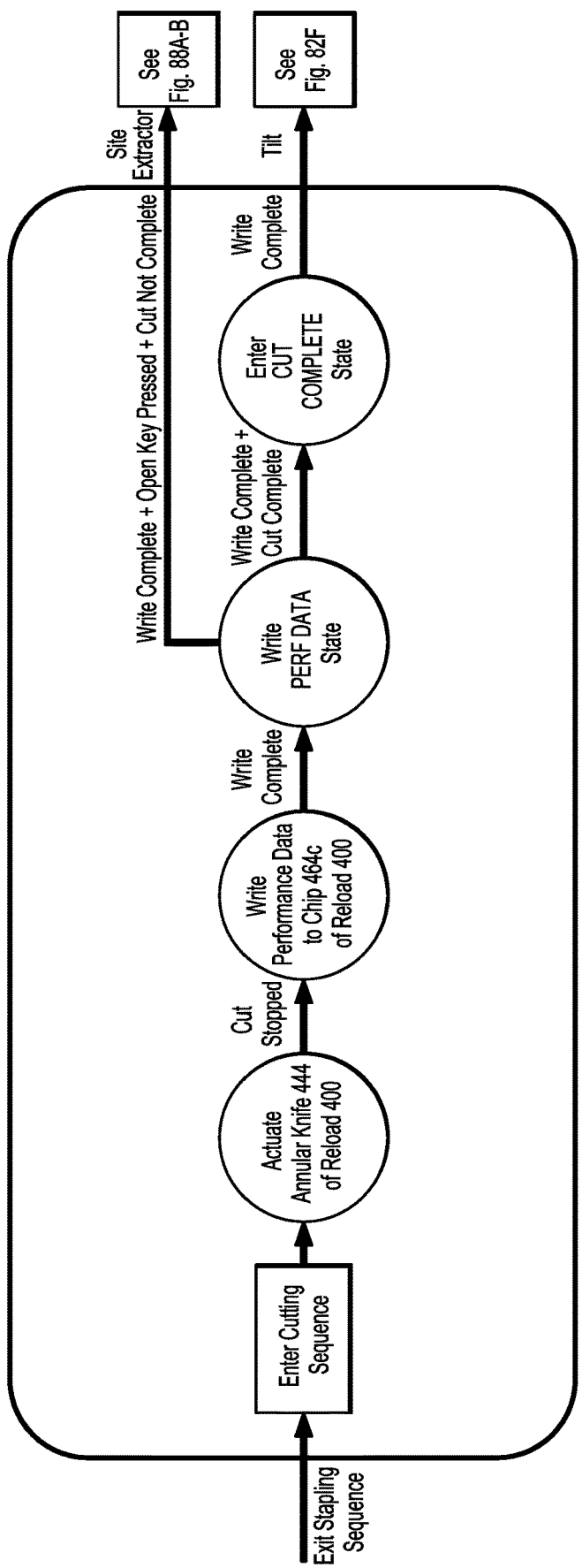

With reference to FIG. 82F, after the stapling and cutting sequences are complete, the user begins an unclamping sequence to release the anvil assembly 510 from the trocar member 274 by pressing on the top of the toggle control button 30. As the toggle control button 30 is pressed up, the trocar member 274 is automatically extended distally, thereby moving the anvil assembly 510 away from circular reload 400 and unclamping the tissue to the preset anvil tilt distance. The unclamping sequence is illustrated on the display screen 146. In particular, an unclamping animation shows the anvil assembly 510 moving distally and the head assembly 512 being tilted. In addition, the display screen 146 also shows a lock icon to show that the anvil assembly 510 is secured to the trocar member 274. Once the anvil assembly 510 is moved away from circular reload 400 to its tilt distance, the display screen 146 shows the anvil assembly 510 in the extended state with the head assembly 512 in the tilted state. This indicates that the user may remove the circular adapter assembly 200 from the patient. The LED then turns off. Once circular adapter assembly 200 is removed, the user then may unlock the anvil assembly 510 from the trocar member 274 by pressing one of the left-side or right-side control buttons 32a, 32b, 34a, 34b of the of the power handle 101 for a predetermined period of time (e.g., 3 seconds or more). The display screen 146 shows which button needs to be pressed on the power handle 101 to unlock the anvil assembly 510. As the user is pressing one of the control buttons 32a, 32b, 34a, 34b, the display screen 146 displays a countdown (e.g., 3, 2, 1) and the lock icon is shown to be in the unlocked state. At this point, the anvil assembly 510 is unlocked and may be removed. The user may then remove reload 400 as well as the severed tissue from the resection procedure. Circular adapter assembly 200 is also detached from handle assembly 100 and is cleaned and sterilized for later reuse. The shell housing 10 is opened and discarded, with the power handle 101 being removed therefrom for reuse.

Regarding cleaning and/or sterilizing of the adapter assembly 200 for later reuse, the inside of the adapter assembly 200 is sealed against any fluid or moisture ingress, or most fluid or moisture ingress. In the event that fluid or moisture should enter the inside of the adapter assembly 200, during the surgical procedure or during the cleaning/sterilizing process, a sterility of the adapter assembly 200 (for subsequent use) and electronic functionality (e.g., of the electrical assembly 310, see FIG. 53) may be affected. Any fluid or moisture entering the adapter assembly 200 can be reliably evacuated if an internal temperature of the adapter assembly 200 reaches a high enough temperature or a long enough period of time, during any sterilizing and/or autoclaving cycles. Accordingly, the adapter assembly 200 is provided with certain features to better ensure that full fluid or moisture evacuation is achieved by the end of the autoclave cycle, irrespective of variations in the settings of the autoclave equipment and/or an interior temperature of the adapter assembly 200 achieved during the autoclave cycle.

In accordance with the present disclosure, in order to address the above-noted occurrences of fluid or moisture ingress and egress from the adapter assembly 200, the adapter assembly 200 is provided with thermal data logging features. Specifically, turning momentarily back to FIG. 53, electronic assembly 310 of the adapter assembly 200, and more specifically, the circuit board 312b of proximal pin connector 312 thereof, may include an electronic temperature sensor 312c (e.g., a thermistor) that is incorporated on the circuit board 312b. The electronic temperature sensor 312c can be queried by an onboard microprocessor (not shown) of the circuit board 312b to log a temperature of the adapter assembly 200.

By achieving a certain temperature threshold and/or a certain duration/time threshold, it has been established that a correlation exists with complete moisture evacuation/egress from the adapter assembly 200, during a sterilizing or autoclaving cycle or the like. According to the present disclosure, upon connecting the adapter assembly 200 to the power handle 101, the user can be provided with information regarding the complete sterilizing/autoclaving of the adapter assembly 200 and/or the complete evacuation of fluid or moisture from within the adapter assembly 200. For example, this may be accomplished by providing a discrete indicator (not shown) on the adapter assembly 200 and/or by activating an image/signal on display screen 146 (see FIG. 12).

It is further contemplated that in addition to, or in lieu of the electronic temperature sensor 312c, the adapter assembly 200 may include a mechanical temperature logger (not shown). For example, the mechanical temperature logger may include a piece of wax having a known size, mass, melting point, etc., and which piece of wax would melt after a minimum temperature threshold is obtained during the sterilization/autoclaving cycles, thereby indicating that appropriate heat has been applied for an appropriate period of time to indicate that fluid or moisture has been fully evacuated.

In accordance with a method of the present disclosure, following a surgical procedure, being that the adapter assembly 200 is reusable, the adapter assembly 200 is subjected to a cleaning, sterilizing and/or autoclaving cycle where cleaning fluids are injected into the adapter assembly 200 (possible under pressure), where the cleaning fluids are drained from the adapter assembly 200 (possible under a negative pressure), and where the adapter assembly 200 is heated for a set period of time, and at a set temperature, to fully evacuate the cleaning fluid therefrom. During the sterilizing/autoclaving cycle, the electronic temperature sensor 312c of the adapter assembly 200 will monitor the temperature and the time, and then log a maximum temperature and/or log the duration of the sterilizing/autoclaving cycle. If an acceptable maximum temperature is attained, and if the duration of the sterilizing/autoclaving cycle has taken place for a minimum amount of time, then the electronic temperature sensor 312c may record and log the event as a successful sterilizing/autoclaving cycle; increment a counter thereof; update a log thereof to indicate that there are a certain number of remaining sterilizing/autoclaving cycle are available; log that no further sterilizing/autoclaving cycle are available; and/or log that the sterilizing/autoclaving cycle was unsuccessful or insufficient.

Thereafter, when the adapter assembly 200 is connected to the power handle 101, the main controller 147 of the power handle 101 interrogates the electronic temperature sensor 312c to access the event log thereof and activate a signal or the display screen 146 which is commensurate with the information contained in the event log of the electronic temperature sensor 312c. For example, the power handle 101 can activate a signal indicating that the adapter assembly 200 has been properly sterilized and is ready for use, that the adapter assembly 200 has not been properly sterilized, or that a life-cycle of the adapter assembly 200 is complete and may not be used further (e.g., disabling use of the power handle 101 and/or the adapter assembly 200).

Figure 23:
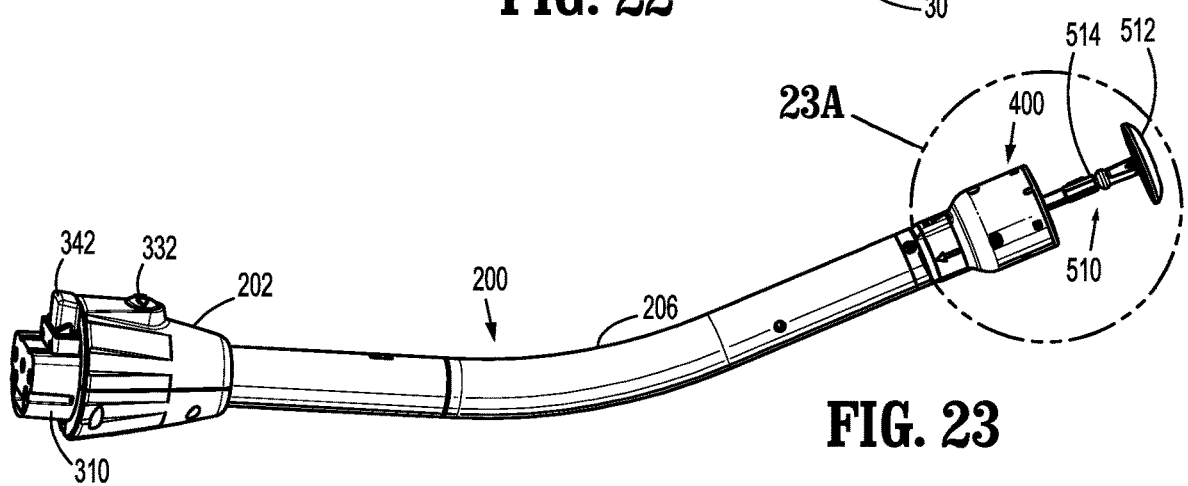
FIG. 23 is a perspective view of the adapter assembly, illustrating a reload secured to a distal end thereof.
Figure 23A:
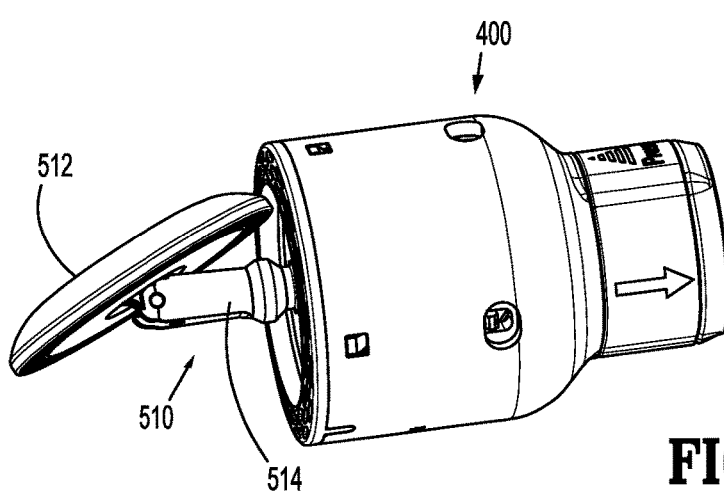
FIG. 23A is an enlarged perspective view of the indicated area of detail of FIG. 23, illustrating a head assembly of an anvil assembly in a tilted condition.
Figure 24:
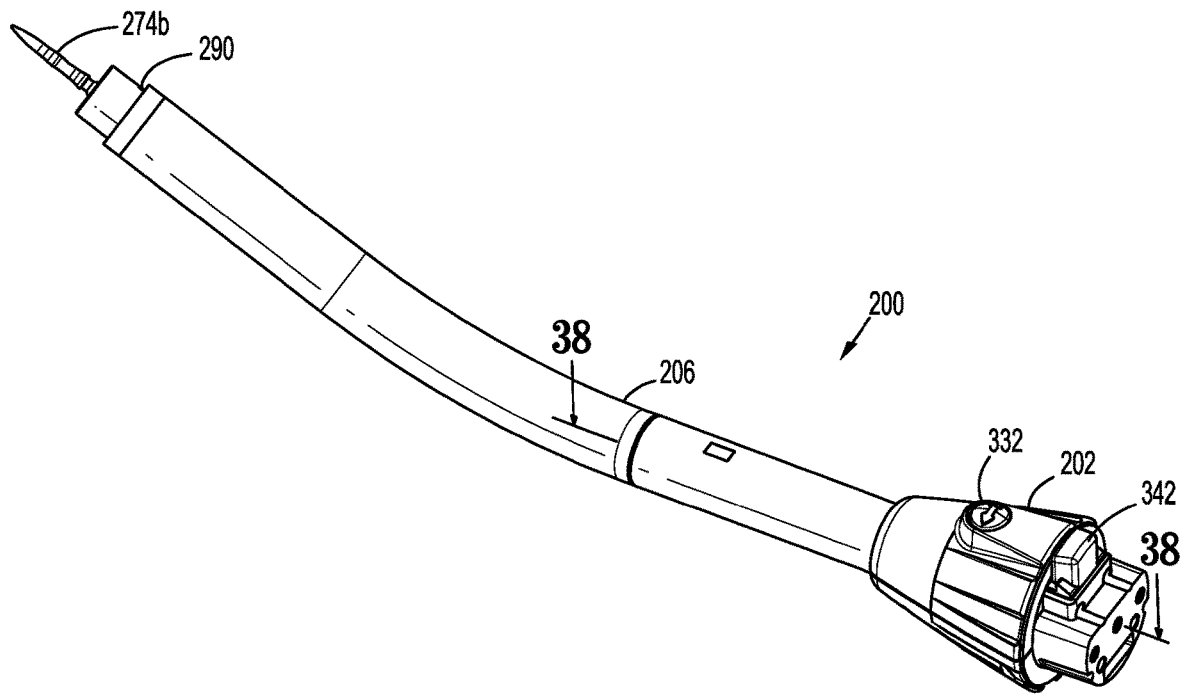
FIG. 24 is a perspective view of the adapter assembly without the reload secured to the distal end thereof.
Figure 25:
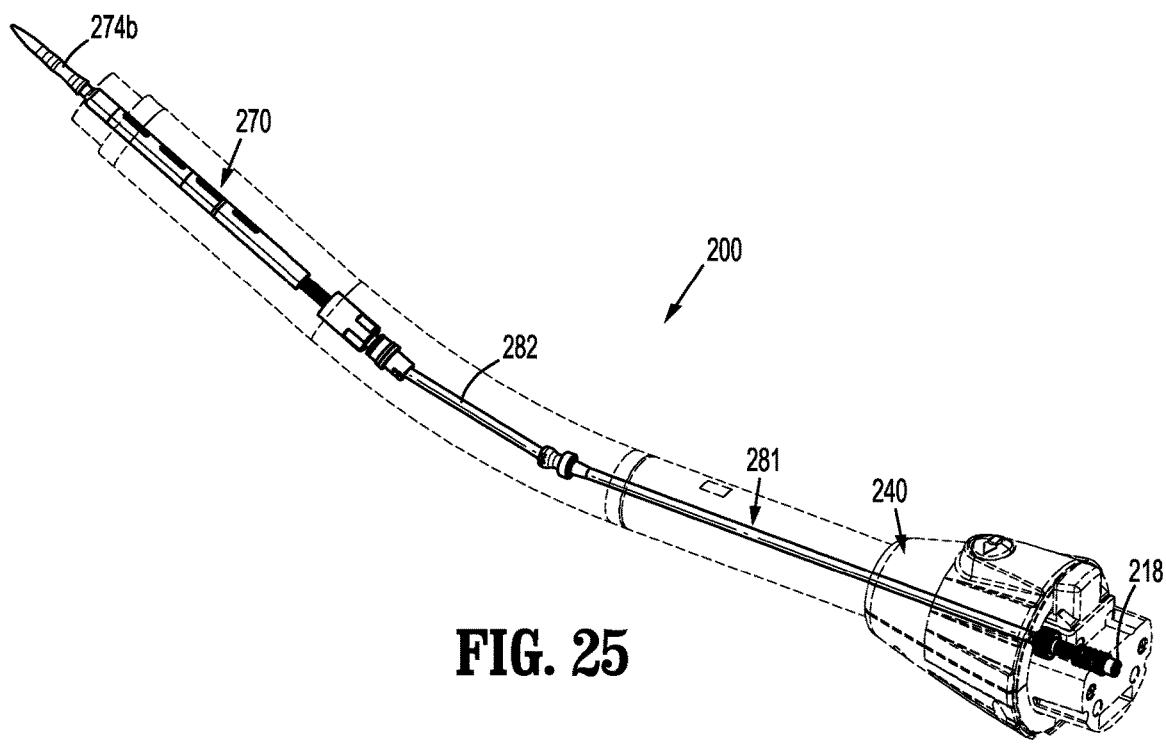
FIG. 25 is a perspective view of the adapter assembly, shown partially in phantom, illustrating a first force/rotation transmitting/converting assembly thereof.
Figure 26:
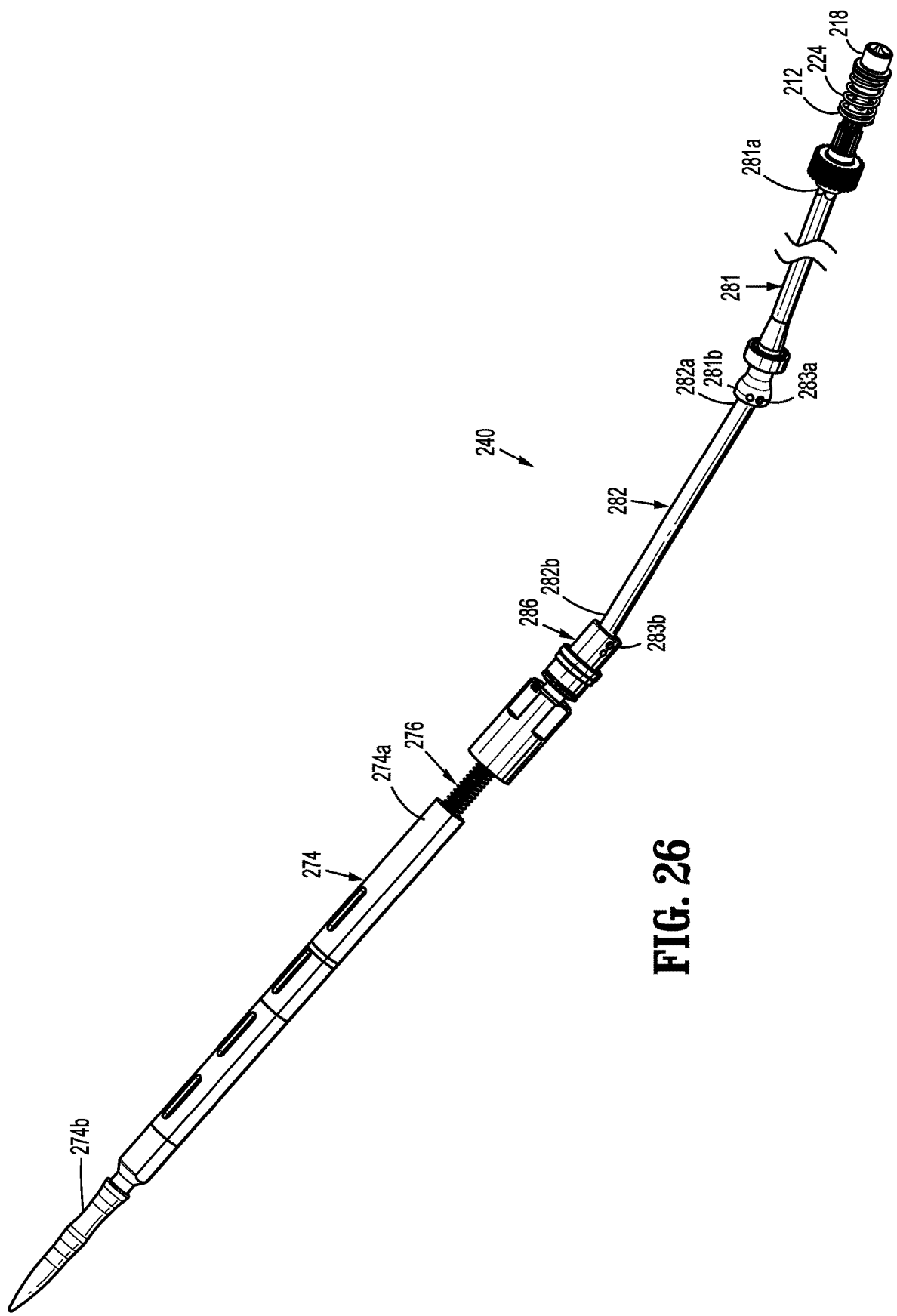
FIG. 26 is a perspective view of the first force/rotation transmitting/converting assembly of FIG. 25.
Figure 27:
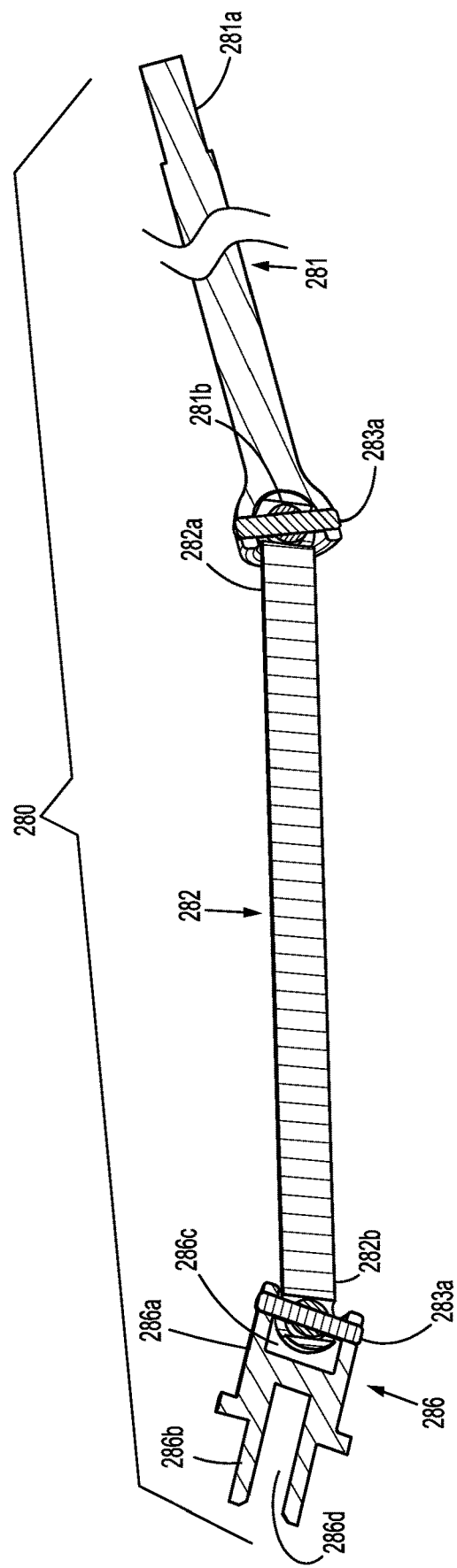
FIG. 27 is a longitudinal, cross-sectional view of a first rotatable proximal drive shaft, a first rotatable distal drive shaft and a coupling member of the first force/rotation transmitting/converting assembly of FIG. 25.
Figure 28:
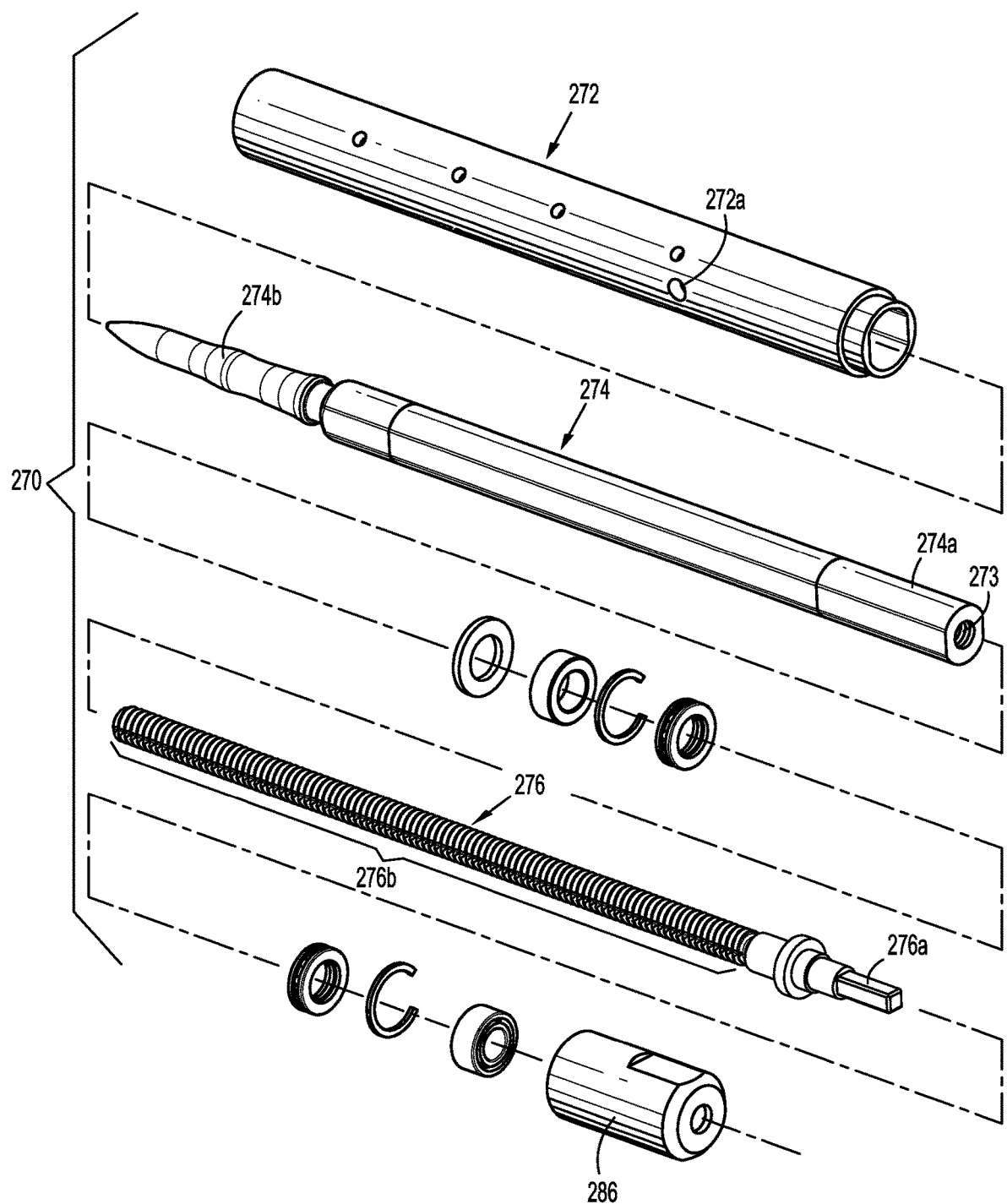
FIG. 28 is a perspective view, with parts separated, of a trocar assembly of the first force/rotation transmitting/converting assembly of FIG. 25.
Figure 33:
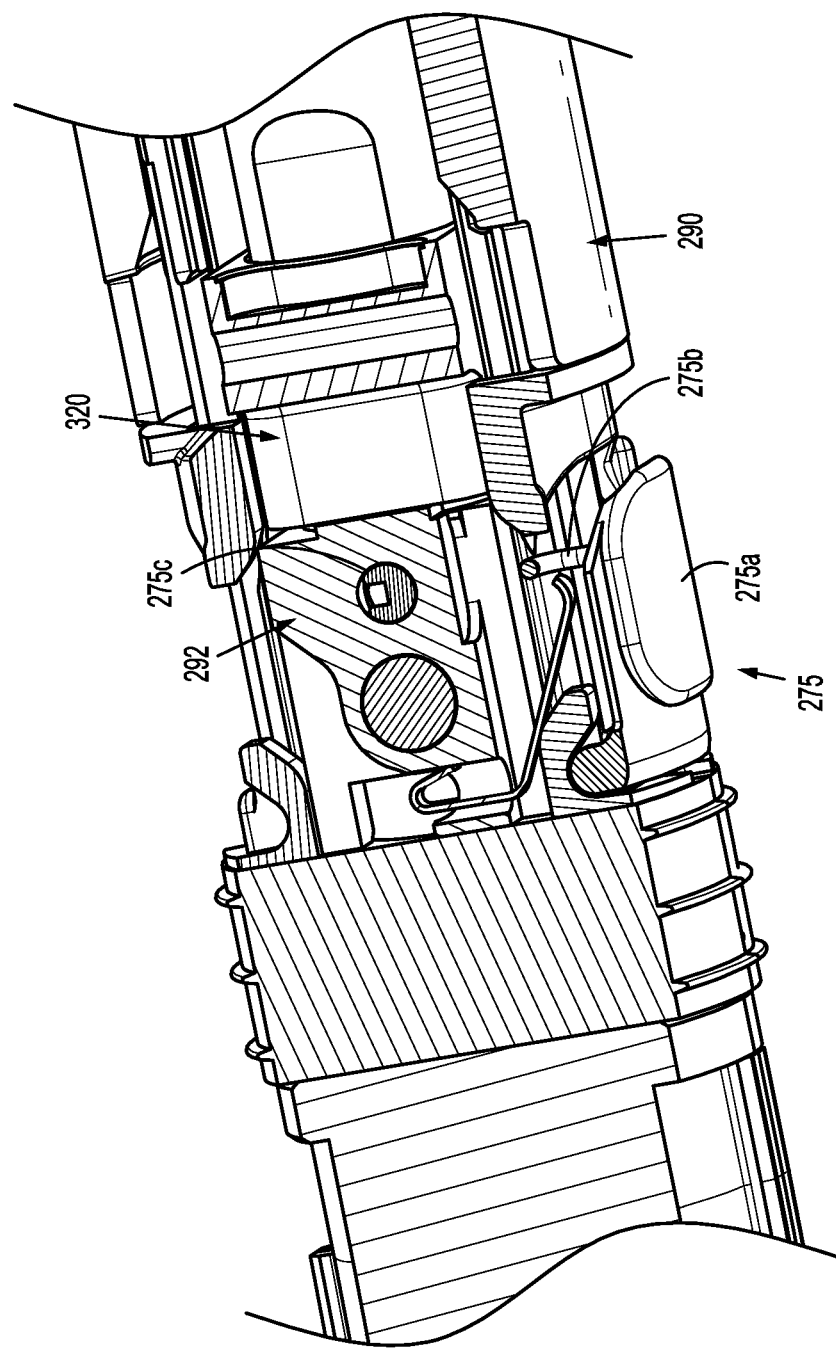
FIG. 33 is a cross-sectional view as taken through 33-33 of FIG. 32.
Figure 34:
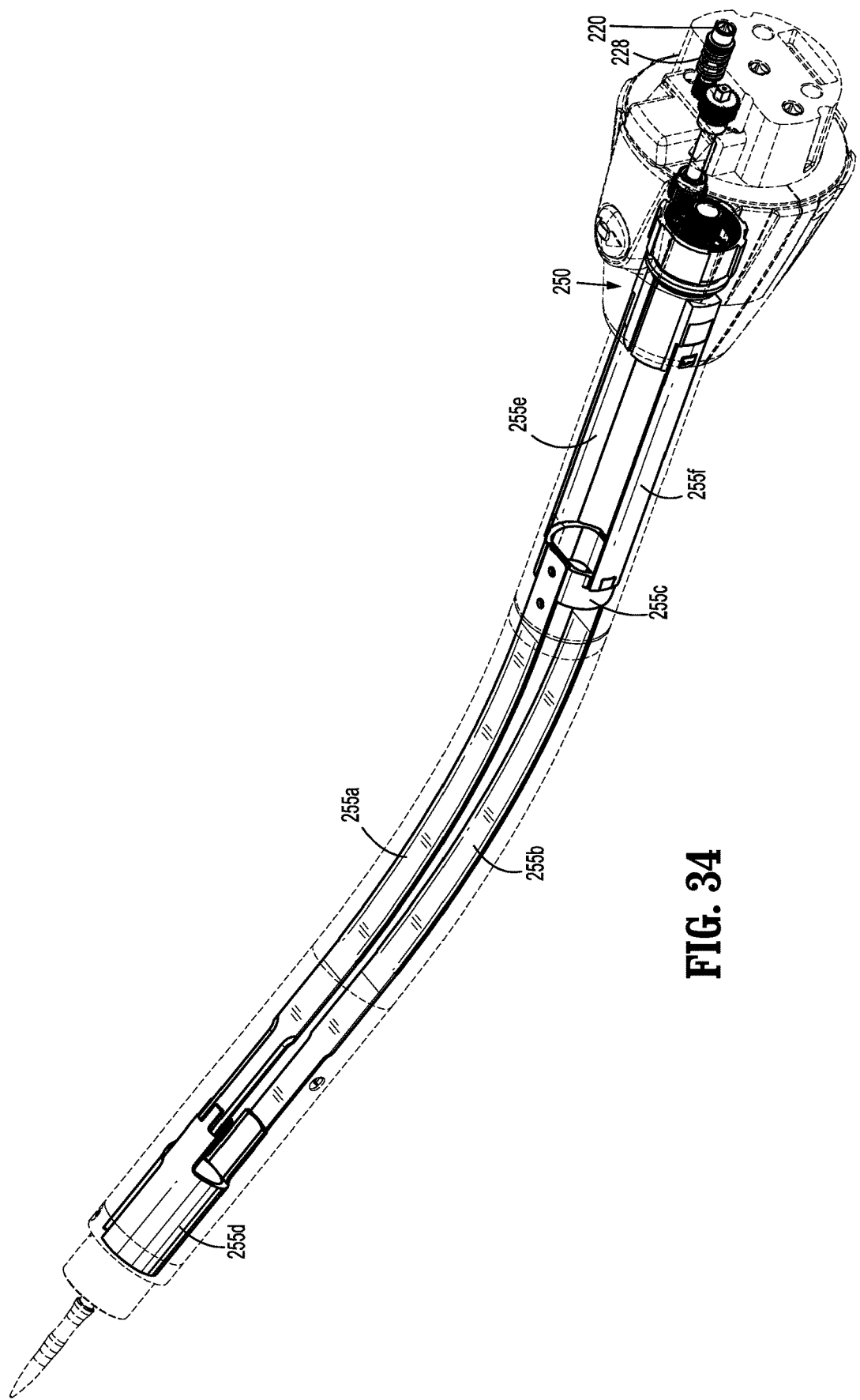
FIG. 34 is a perspective view of the adapter assembly, shown partially in phantom, illustrating a second force/rotation transmitting/converting assembly thereof.
Figure 37:
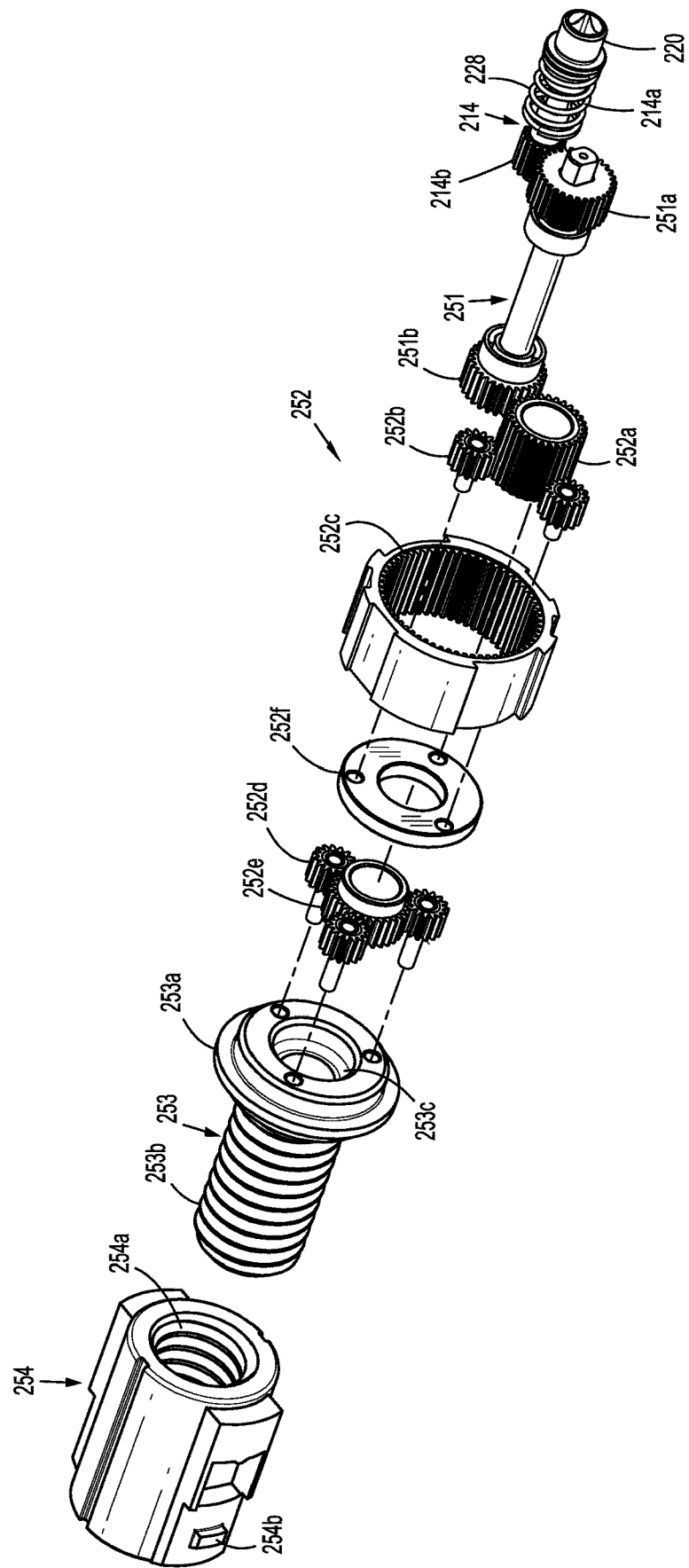
FIG. 37 is a perspective view, with parts separated, of a planetary gear set and staple driver, of the second force/rotation transmitting/converting assembly of FIG. 34.
Figure 38:
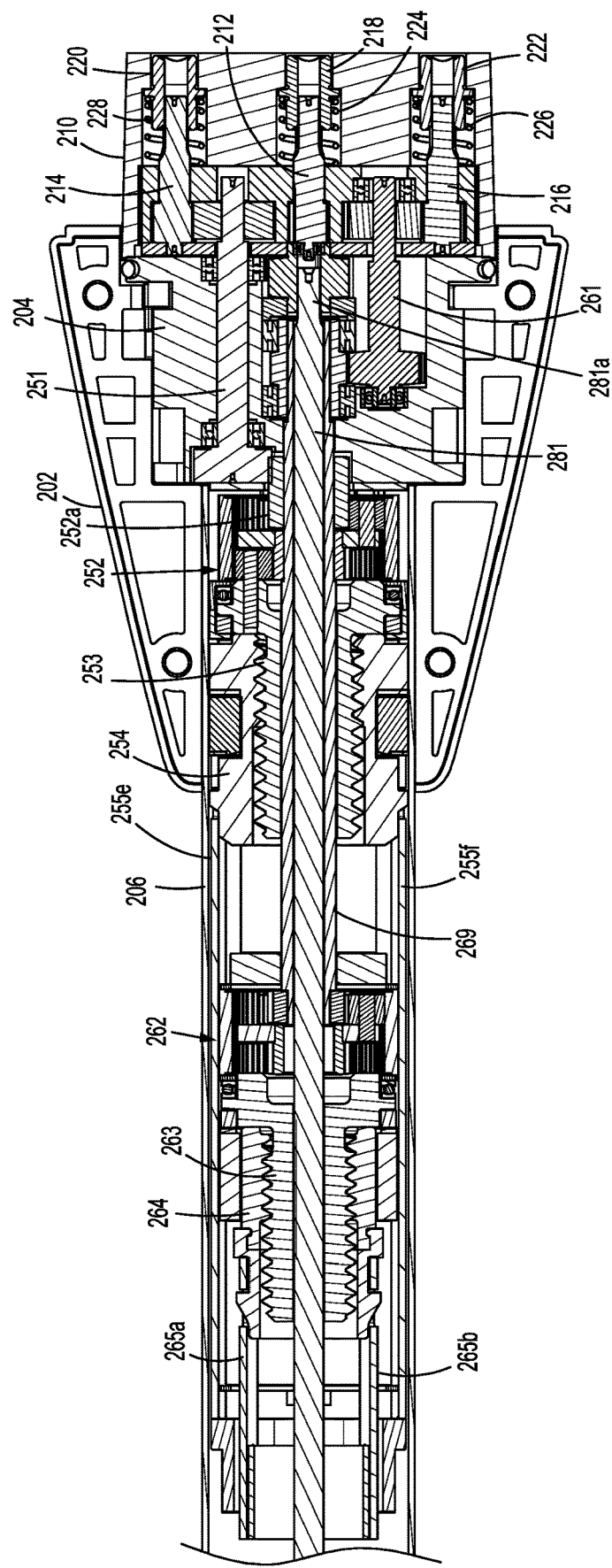
FIG. 38 is a cross-sectional view as taken through 38-38 of FIG. 24.
Figure 39:
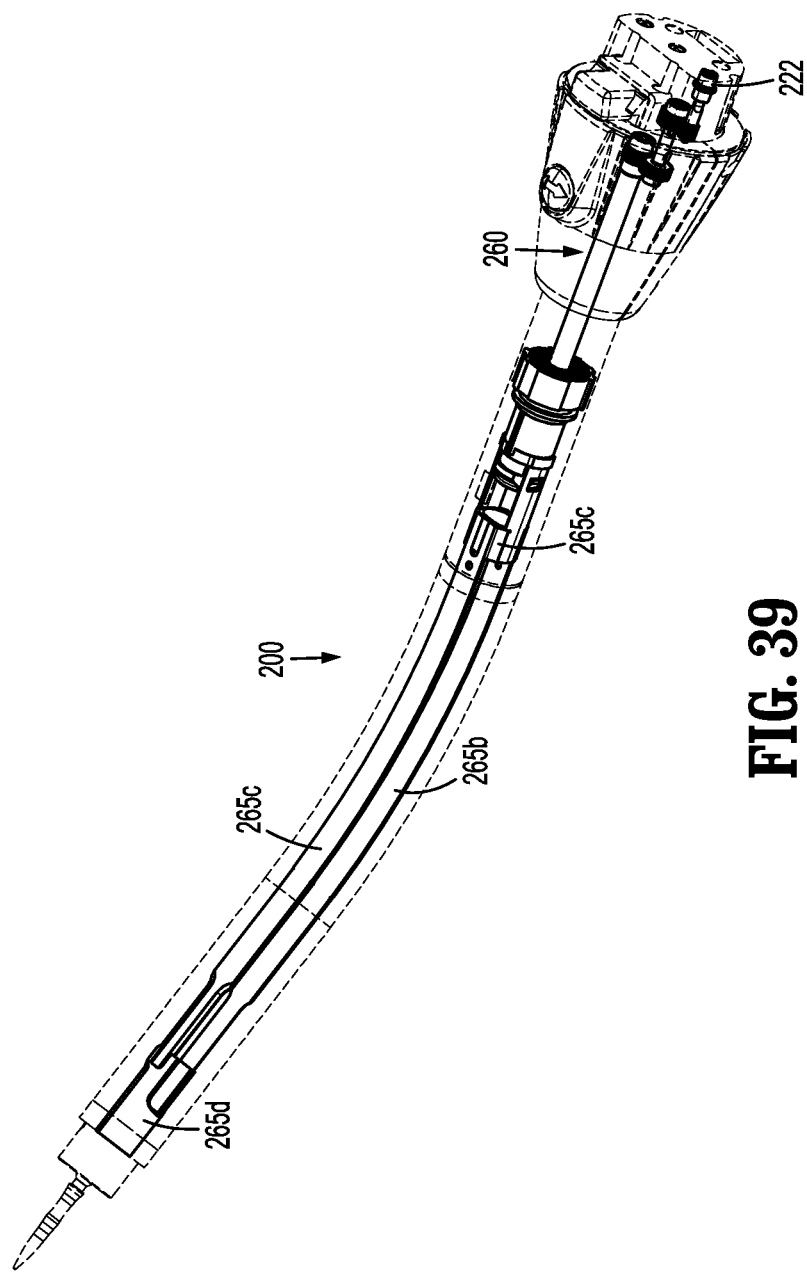
FIG. 39 is a perspective view of the adapter assembly, shown partially in phantom, illustrating a third force/rotation transmitting/converting assembly thereof.
Figure 42:
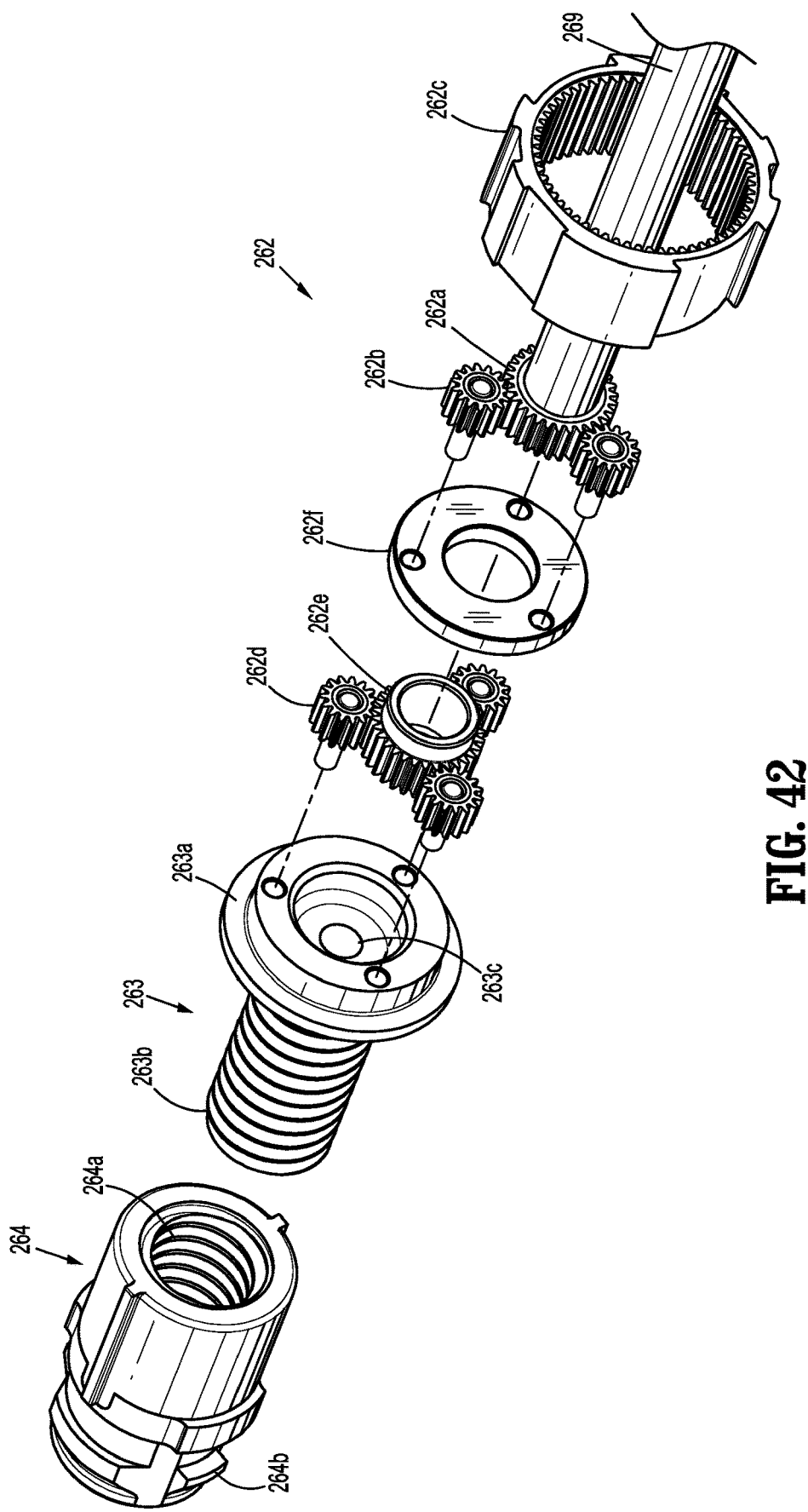
FIG. 42 is a perspective view, with parts separated, of a planetary gear set and knife driver, of the third force/rotation transmitting/converting assembly of FIG. 39.
Figure 43:
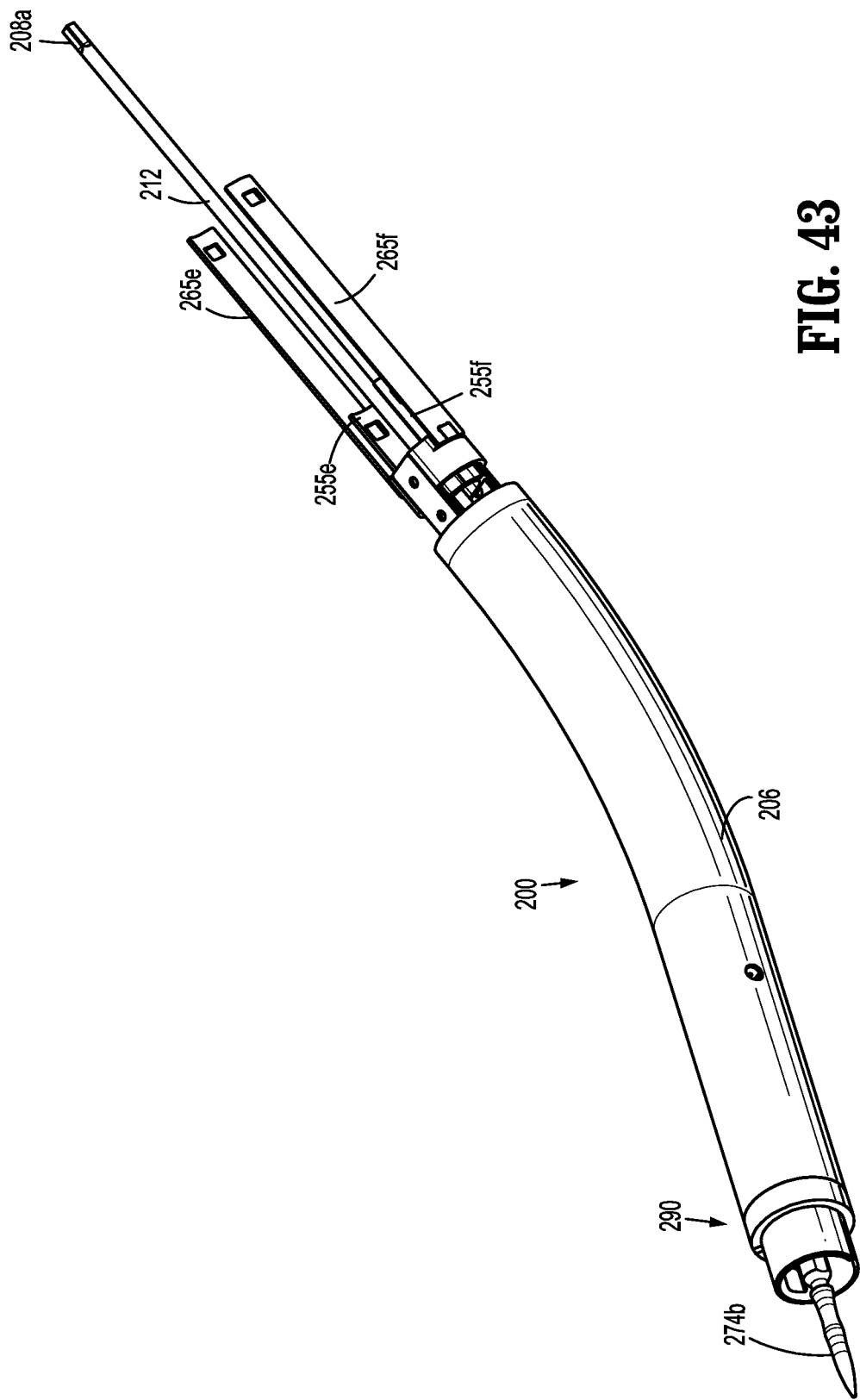
FIG. 43 is a perspective view of a distal portion of the adapter assembly.
Figure 44:
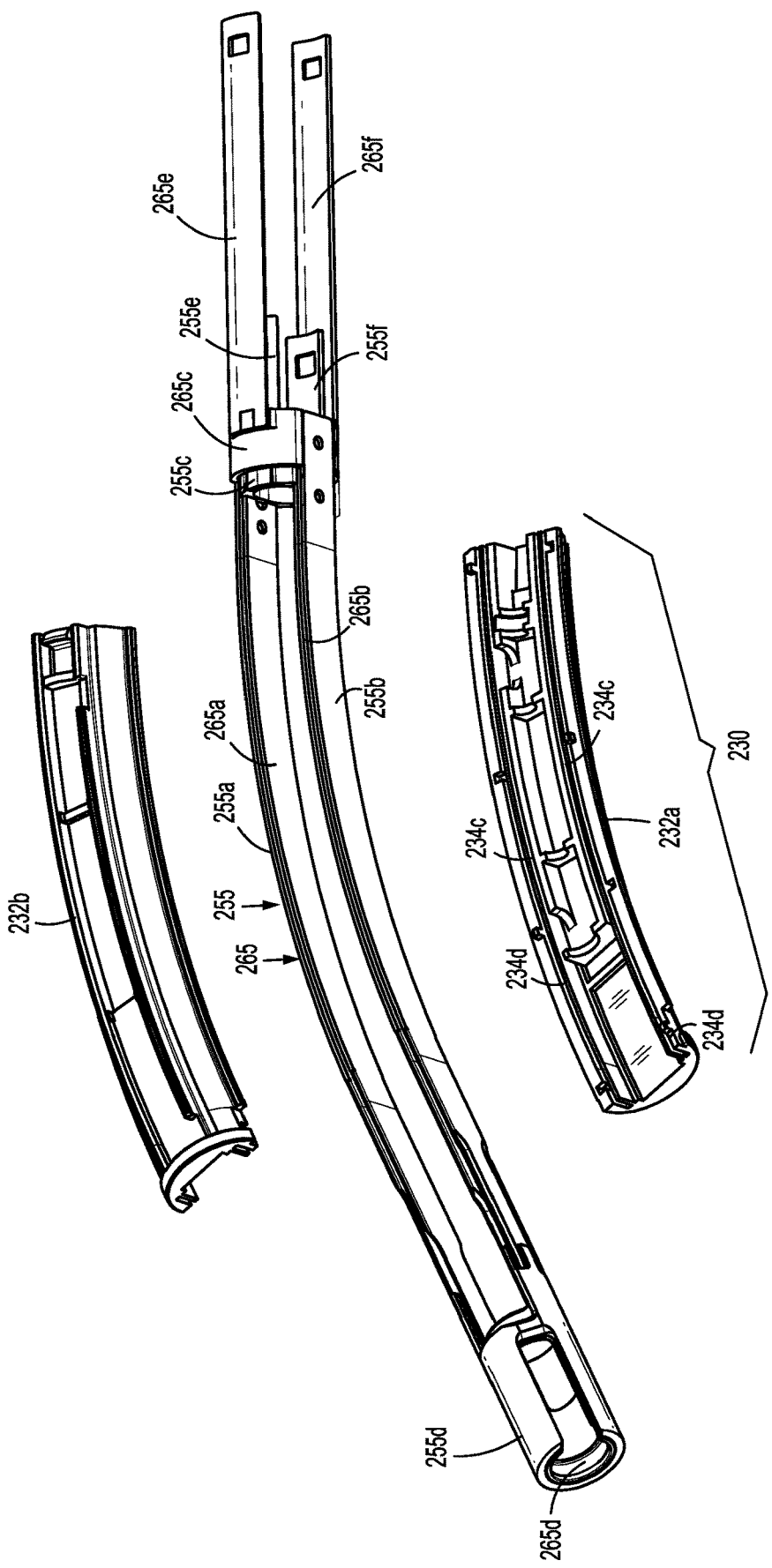
FIG. 44 is a further perspective view, with parts separated, of a distal portion of the adapter assembly.
Figure 45:
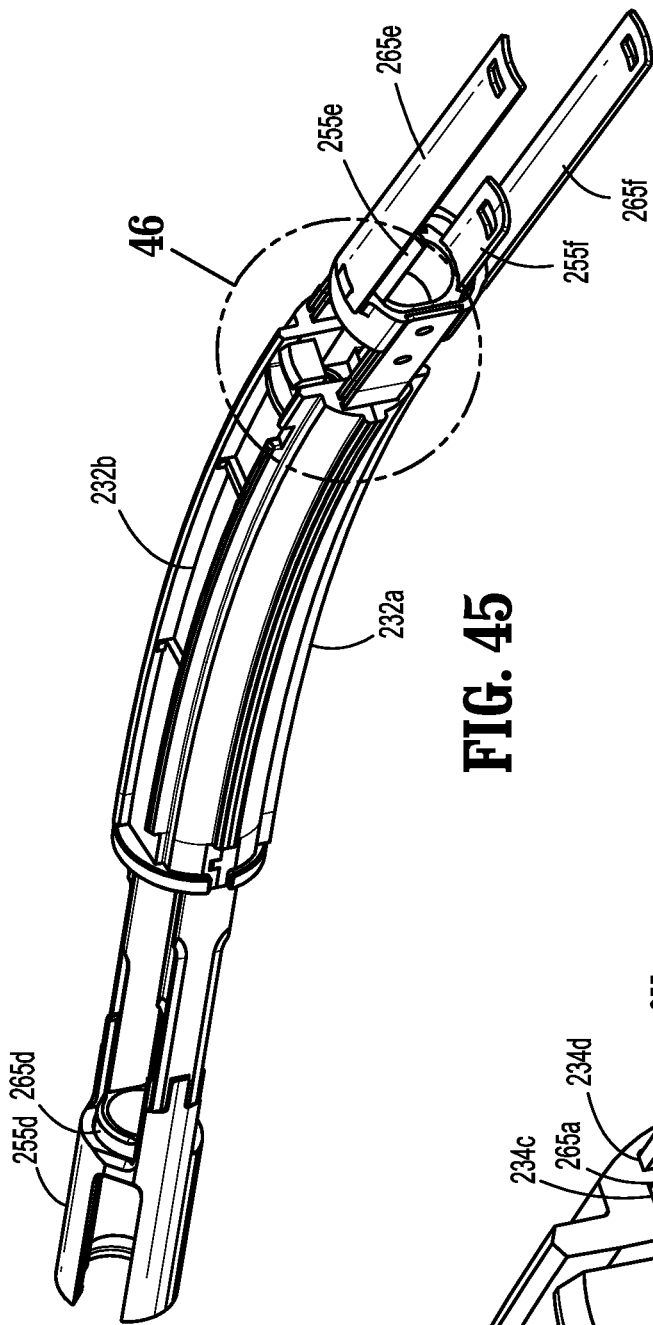
FIG. 45 is a rear, perspective view of the internal components of the distal end portion of the adapter assembly.
Figure 46:
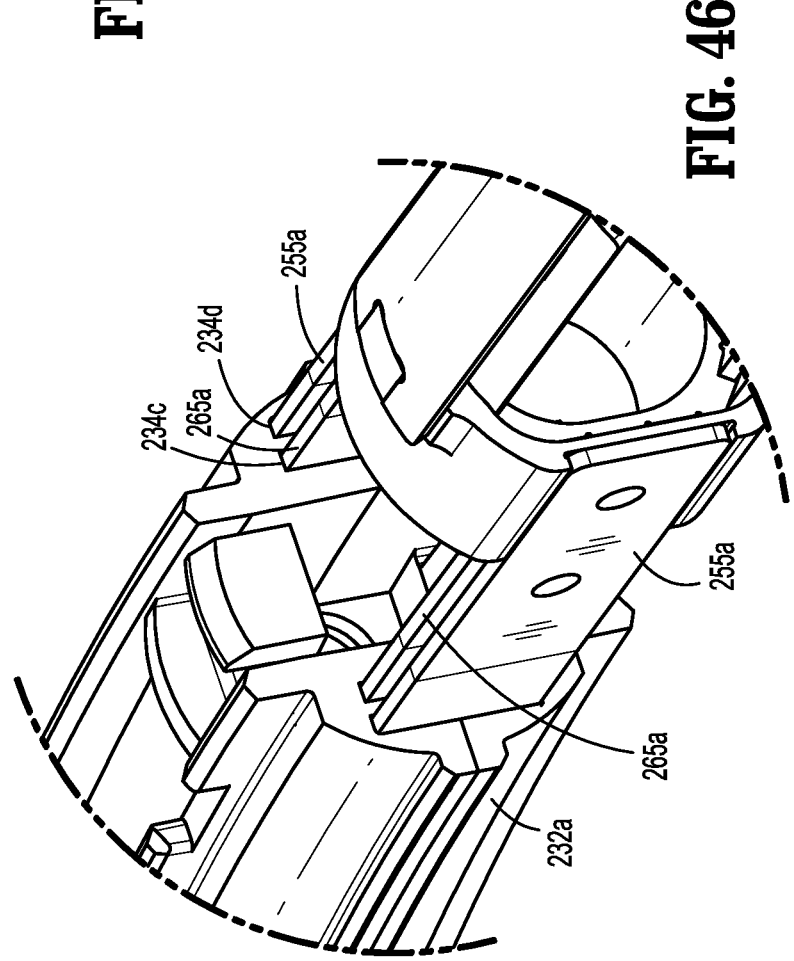
FIG. 46 is an enlarged view of the indicated area of detail of FIG. 45.
Figure 49:
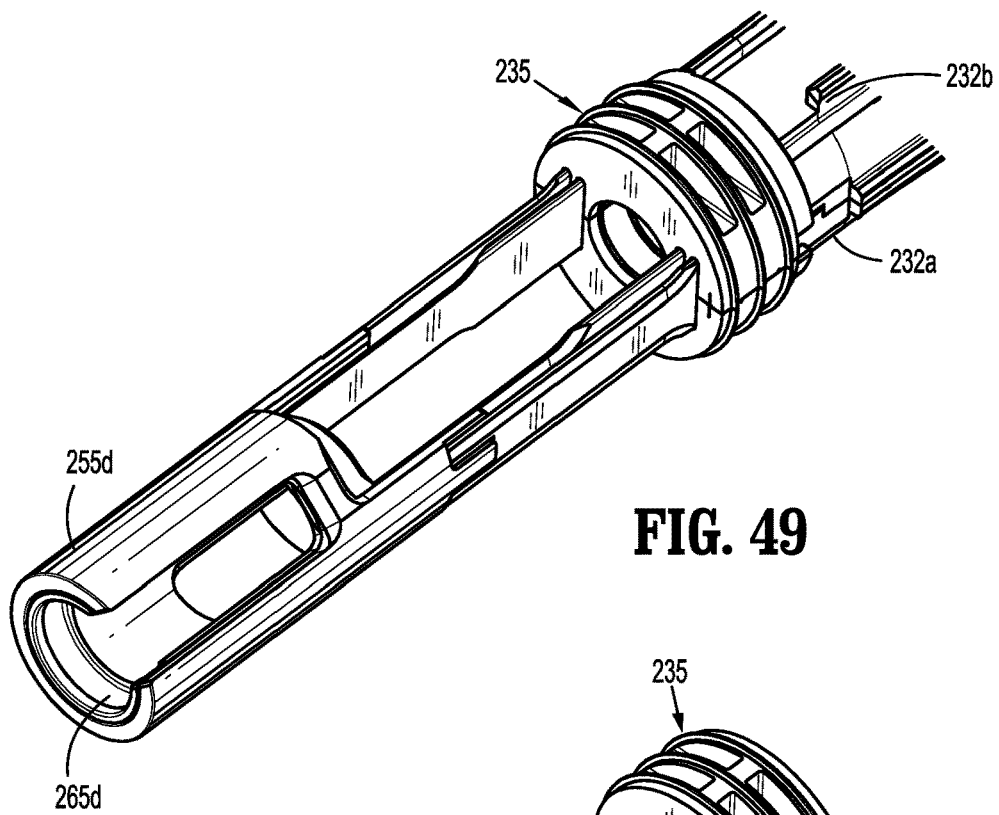
FIG. 49 is a front, perspective view of the internal components of a more distal end portion of the adapter assembly of FIGS. 45-48.
Figure 50:
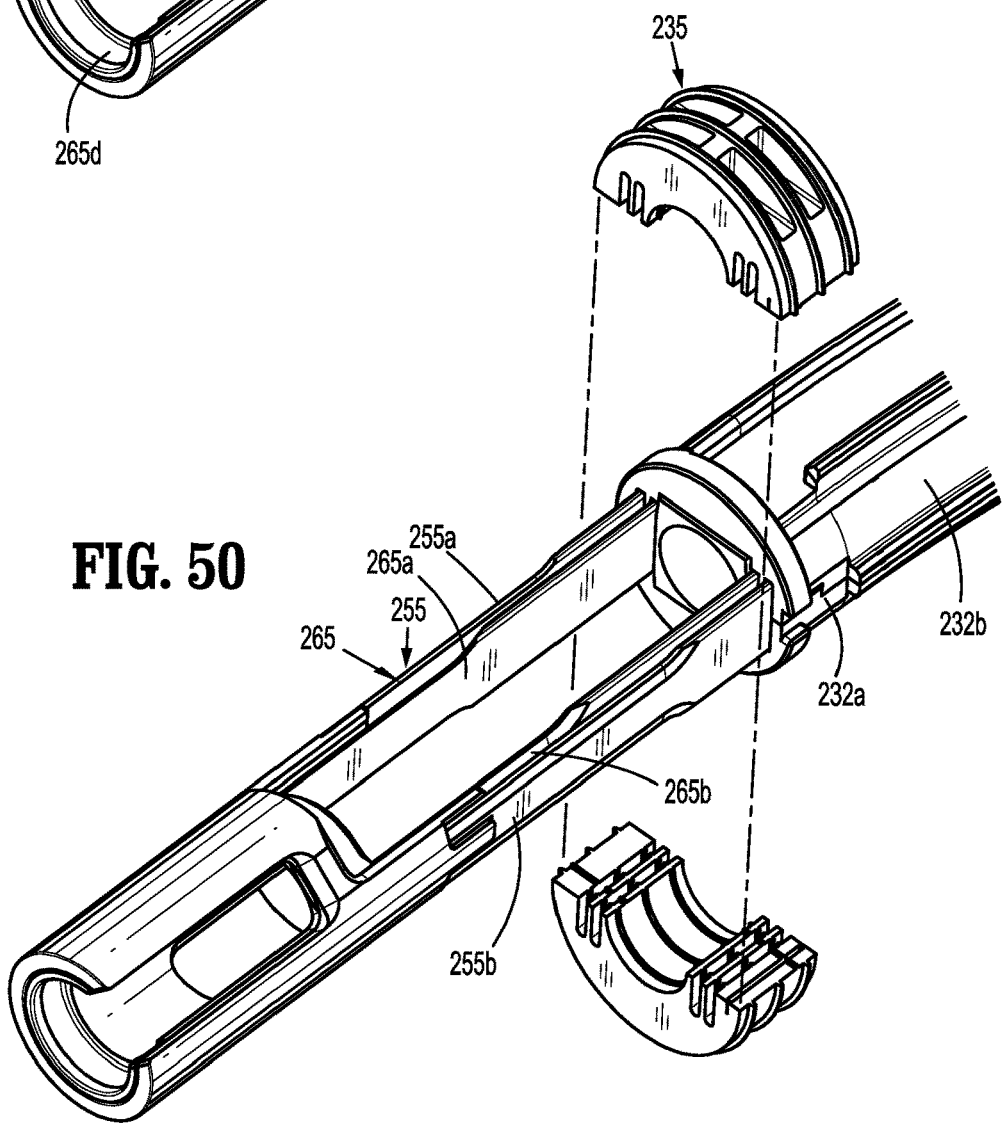
FIG. 50 is a front, perspective view, with parts separated, of the internal components of the more distal end portion of the adapter assembly of FIG. 49.
Figure 51:
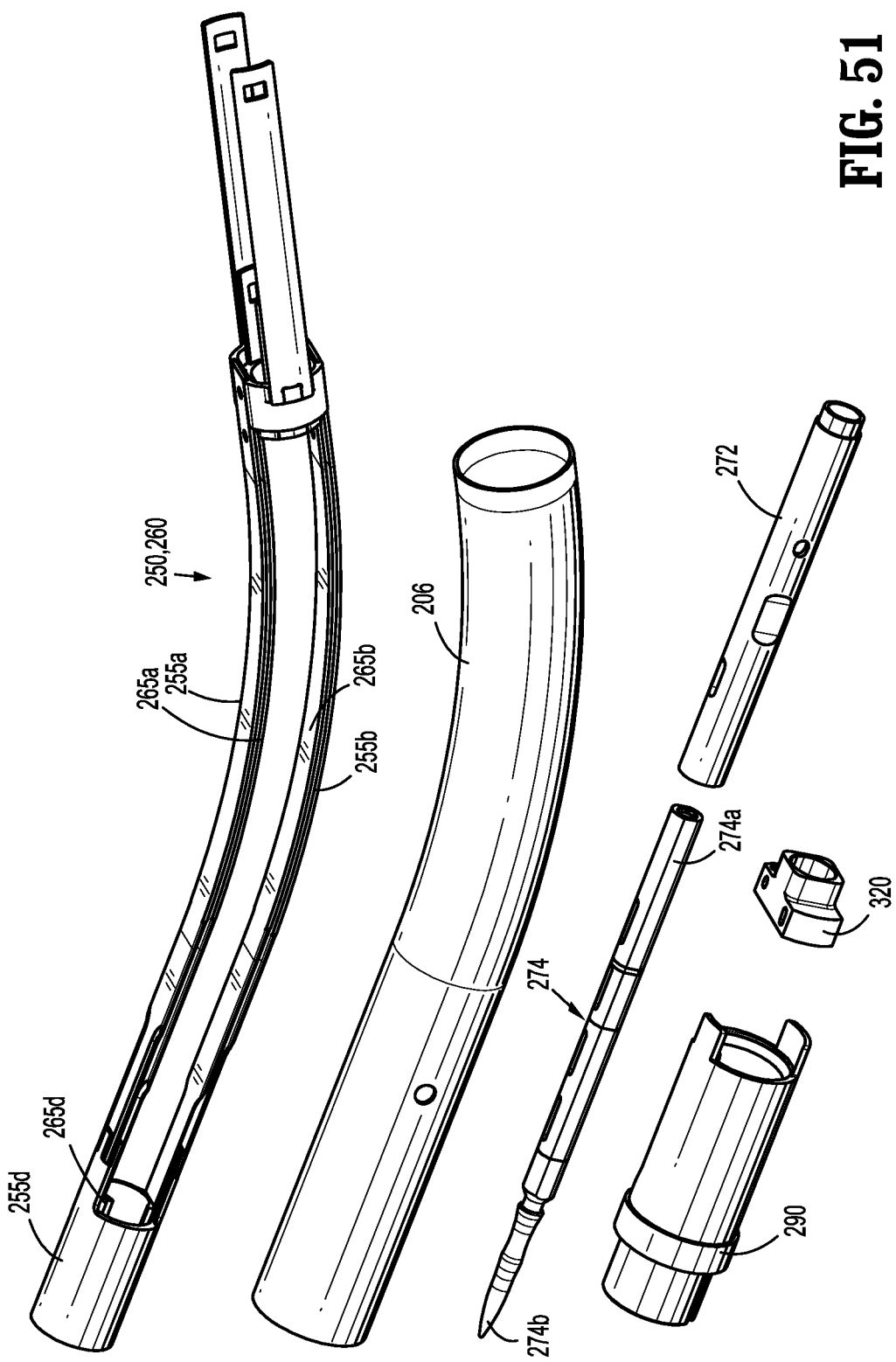
FIG. 51 is a perspective view, with parts separated, of the distal end portion of the adapter assembly of FIGS. 45-50.
Figure 52:
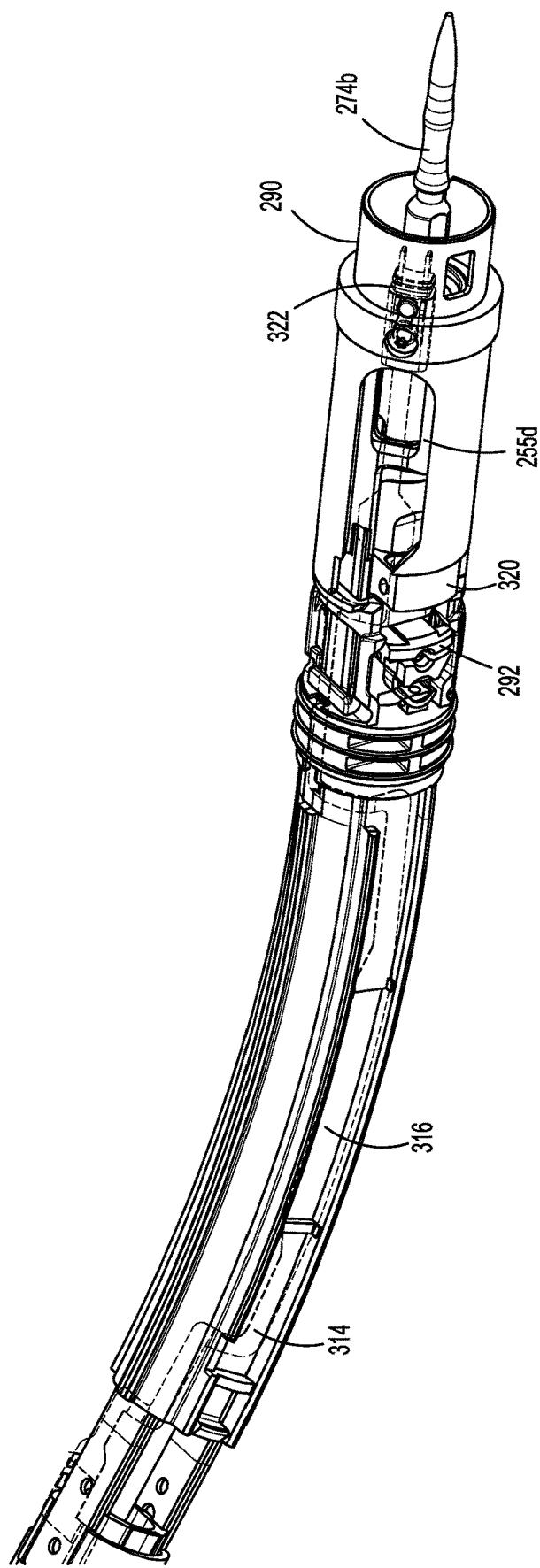
FIG. 52 is a perspective view of the distal end portion of the adapter assembly of FIGS. 45-51, illustrating an electrical assembly thereof.

In accordance with the present disclosure, with reference once again to FIG. 82E, after the stapling and cutting sequences are complete, to prevent the tilted anvil assembly 510 (e.g., the anvil assembly 510 with the head assembly 512 in the titled condition) from clamping against the circular reload 400, and potentially pinching and/or trapping anastomosed tissue between the head assembly 512 and the circular reload 400, the position of the trocar member 274 is monitored by the main controller 147 of the power handle 101. In this manner, when the power handle 101 is in this "surgical site extraction state" (that is, after the anastomosis is complete, and before the surgical device is removed from the surgical site), and when the trocar member 274 (of the trocar assembly 270 of the adapter assembly 200, see FIGS. 28 and 82E) is in a position such that the head assembly 512 of the anvil assembly 510 is close to the reload 400 (and may allow tissue to become trapped between the tilted head assembly 512 (see FIG. 23a) of the anvil assembly 510 and the reload 400), the force exerted on the strain gauge assembly 320 (see FIGS. 52-54) is monitored (by main controller 147) to detect if/when the tilted head assembly 512 of the anvil assembly 510 is drawn/re-drawn into the reload 400.

Accordingly, during the "surgical site extraction state" (e.g., the tilted head assembly 512 being drawn/re-drawn into the reload 400), if/when a predetermined threshold force, exerted on the strain gauge assembly 320, is exceeded (e.g., by the tilted head assembly 512 pinching or trapping tissue against a surface of the reload 400 or the like), the main controller 147 may disable or stop the power handle 101 from further moving the tilted head assembly 512 towards the reload 400, thereby stopping any undesired pinching or trapping of tissue between the head assembly 512 and the reload 400. Further, it is contemplated that the main controller 147 may activate an audible, visual, and/or tactile alert for the user. As can be appreciated, entry of the main controller 147 into a "re-clamp" monitoring state may be contingent upon the relative size and position of the trocar assembly 270, the center rod assembly 514 and/or head assembly 512, as well and the relative size (e.g., staple size, knife diameter, etc.) of the reload 400 that is attached to the adapter assembly 200.

The powered stapler according to the present disclosure is also configured to enter recovery states during the clamping, stapling, and cutting sequences if any of the components, e.g., the power handle 101, circular adapter assembly 200, circular reload 400, and/or the anvil assembly 510, encounter errors. The recovery states are software states executed by main controller 147 that guide the user through correcting and/or troubleshooting the errors and allow the user to resume any of the clamping, stapling, and cutting sequences once the error is corrected.

At the start of each operational sequence (e.g., clamping, stapling, firing, etc.), the main controller 147 writes to the storage device 407 of the circular adapter assembly 200 a recovery code associated with the operational sequence. Thus, at the start of the procedure the storage device 407 stores an initialization recovery code indicating that the circular adapter assembly 200 has not yet been used. However, as the circular adapter assembly 200 is used throughout the procedure, namely, progressing through the different sequences described above, corresponding recovery codes are written to the storage device 407. In addition, the main controller 147 writes corresponding recovery states to the memory 141. In either instance, this allows for replacement of either of the adapter assembly 200 and/or the power handle 101 depending on the error state as both of the components store the last recovery state locally, namely, in the storage device 407 or the memory 141, respectively.

With reference to FIG. 87A, which shows a recovery procedure during the stapling sequence and FIG. 88A, which shows a recovery procedure during the cutting sequence, during the procedure there may be instances that the power handle 101 identifies a flaw with one or more of the components of the power handle 101, the circular adapter assembly 200, and/or the reload 400. These recovery procedures are illustrative and similar procedures are also envisioned to be implemented in other operational sequences of the power handle 101, e.g., clamping sequence. The recovery procedures may include, but are not limited to, attaching a new power handle 101 to an adapter assembly 200 that is inserted into the patient, replacing the adapter assembly 200 and/or the reload 400.

When an adapter assembly 200 is attached to the power handle 101, the power handle 101 reads the recovery code from the storage device 407 to determine the state of the adapter assembly 200. The recovery code was written when the adapter assembly 200 was previously detached from the power handle 101. As noted above, at the start of the procedure, the recovery code indicates the initial state, which directs the power handle 101 to transition into start-up sequence, e.g., calibration. If the adapter assembly 200 was detached in the middle of the procedure, e.g., clamping, stapling, cutting, etc., the corresponding recovery code provides the entry point back into the mainline flow after performing a recovery procedure. This allows the operator to continue the surgical procedure at the point where the adapter assembly 200 was originally detached.

Similarly, in situations where the power handle 101 is being replaced, a new power handle 101 is configured to read the recovery state from the adapter assembly 200. This allows the new power handle 101 to resume operation of the previous power handle 101. Thus, during any of the operational sequences, e.g., clamping, stapling, and cutting, the adapter assembly 200 may be left in the corresponding configuration, e.g., clamped, stapled, etc., and after the new power handle 101 is attached, operation may be resumed.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A handheld electromechanical surgical device capable of effectuating a surgical procedure, the surgical device comprising:
    a handle assembly including:
        a power source;
        at least one motor coupled to the power source; and
        a controller configured to control the motor;
    an adapter assembly coupled to and extending from the handle assembly, the adapter assembly including:
        a force transmitting and rotation converting assembly for receiving and communicating a rotation from the at least one motor of the handle assembly to axially translating forces of a driven assembly thereof; and
        an electrical assembly having a proximal end in communication with the controller of the handle assembly, and a distal end; and
    a reload configured to selectively connect to a distal portion of the adapter assembly, the reload including:
        a reload housing;
        an annular array of staples disposed within the reload housing;
        an annular staple pusher disposed within the reload housing and being configured for ejecting the staples; and
        a chip assembly supported within the reload housing, the chip assembly including:
            a chip housing defining a cavity having an open end oriented in a proximal direction;
            a pair of contact members retained within the cavity of the chip housing at a location recessed within the cavity; and
        a data storage device retained in the cavity of the chip housing and being located between the pair of contact members, the data storage device being selectively connectable to the distal end of the electrical assembly of the adapter assembly, wherein the data storage device receives and stores performance data of the surgical device from the controller of the handle assembly.

2. The surgical device according to claim 1, wherein the data storage device of the reload includes information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

3. The surgical device according to claim 1, wherein the data storage device of the reload is configured to have performance data written thereto and stored thereon during or following any use thereof.

4. The surgical device according to claim 3, wherein the data storage device of the reload is configured to have performance data written thereto and stored thereon following a successful or unsuccessful firing of the surgical device.

5. The surgical device according to claim 4, wherein the performance data written and stored to the data storage device of the reload includes clamping forces for the surgical procedure, stapling forces for the surgical procedure, cutting forces for the surgical procedure, a maximum clamping force, a maximum stapling force or a maximum cutting force.

6. The surgical device according to claim 5, wherein the performance data is written and stored to the controller of the handle assembly.

7. The surgical device according to claim 1, wherein, during or following any use of the surgical device, performance data related to the use of the surgical device is written to and stored in the data storage device of the reload.

8. The surgical device according to claim 7, wherein, following a successful or unsuccessful firing of the surgical device, performance data related to the successful or unsuccessful firing is written to and stored in the data storage device of the reload.

9. The surgical device according to claim 8, wherein the performance data written and stored to the data storage device of the reload includes clamping forces for the surgical procedure, stapling forces for the surgical procedure, cutting forces for the surgical procedure, a maximum clamping force, a maximum stapling force or a maximum cutting force.

10. The surgical device according to claim 9, wherein the data storage device of the reload includes information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

11. The surgical device according to claim 10, wherein the performance data is written and stored to the controller of the handle assembly.

12. A surgical staple reload for use with a handheld electromechanical surgical device during a surgical procedure, the surgical staple reload comprising:
- a reload housing configured to selectively connect to a distal portion of the handheld electromechanical surgical device;
- an annular array of staples disposed within the reload housing;
- an annular staple pusher disposed within the reload housing and being configured for ejecting the staples; and
- a chip assembly supported within the reload housing, the chip assembly including:
  - a chip housing defining a cavity having an open end oriented in a proximal direction;
  - a pair of contact members retained within the cavity of the chip housing; and
  - a data storage device retained in the cavity of the chip housing and being located between the pair of contact members, the data storage device being selectively connectable to an electrical assembly of the handheld electromechanical surgical device, wherein the data storage device receives and stores performance data of the handheld electromechanical surgical device from a controller of the handheld electromechanical surgical device.

13. The surgical staple reload according to claim 12, wherein the data storage device includes information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

14. The surgical staple reload according to claim 12, wherein the data storage device is configured to have performance data written thereto and stored thereon during or following any use thereof.

15. The surgical staple reload according to claim 14, wherein the data storage device is configured to have performance data written thereto and stored thereon following a successful or unsuccessful firing of the handheld electromechanical surgical device.

16. The surgical staple reload according to claim 15, wherein the performance data written and stored to the data storage device includes clamping forces for the surgical procedure, stapling forces for the surgical procedure, cutting forces for the surgical procedure, a maximum clamping force, a maximum stapling force or a maximum cutting force.

17. The surgical staple reload according to claim 16, wherein the performance data is written and stored to the controller of the handheld electromechanical surgical device.

18. The surgical staple reload according to claim 12, wherein, during or following any use of the handheld electromechanical surgical device, performance data related to the use of the handheld electromechanical surgical device is written to and stored in the data storage device of the staple reload.

19. The surgical staple reload according to claim 18, wherein, following a successful or unsuccessful firing of the handheld electromechanical surgical device, performance data related to the successful or unsuccessful firing is written to and stored in the data storage device of the reload.

20. The surgical staple reload according to claim 19, wherein the performance data written and stored to the data storage device includes clamping forces for the surgical procedure, stapling forces for the surgical procedure, cutting forces for the surgical procedure, a maximum clamping force, a maximum stapling force or a maximum cutting force.

21. The surgical staple reload according to claim 20, wherein the data storage device includes information pre-stored thereon prior to any use thereof, the pre-stored information includes at least one of lot number, staple size, knife diameter, lumen size, fire count, manufacturing stroke offsets, excessive force index, shipping cap assembly presence, or demonstration modes.

22. The surgical staple reload according to claim 21, wherein the performance data is written and stored to the controller of the handheld electromechanical surgical device.

* * * * *